US005662896A

United States Patent [19]
Barber et al.

[11] Patent Number: 5,662,896
[45] Date of Patent: Sep. 2, 1997

[54] COMPOSITIONS AND METHODS FOR CANCER IMMUNOTHERAPY

[75] Inventors: Jack R. Barber, San Diego; Douglas J. Jolly, Leucadia; James G. Respess, San Diego, all of Calif.

[73] Assignee: Chiron Viagene, Inc., San Diego, Calif.

[21] Appl. No.: 32,846

[22] Filed: Mar. 17, 1993

Related U.S. Application Data

[63] Continuation-in-part of Ser. No. 965,084, Oct. 22, 1992, abandoned, which is a continuation of Ser. No. 586,603, Sep. 21, 1990, abandoned, which is a continuation-in-part of Ser. No. 565,606, Aug. 10, 1990, abandoned, which is a continuation-in-part of Ser. No. 395,932, Aug. 18, 1989, abandoned, which is a continuation-in-part of Ser. No. 170,515, Mar. 21, 1988, abandoned.

[51] Int. Cl.$^6$ .................... A61K 48/00; C12N 15/86; C12N 15/23; C12N 15/26
[52] U.S. Cl. .................... 424/93.2; 424/93.1; 435/320.1; 514/44
[58] Field of Search .................... 435/320.1, 240.2; 514/44; 424/93.1, 93.2

[56] References Cited

U.S. PATENT DOCUMENTS 5,223,408   6/1993   Goeddel et al. .................... 435/69.3

FOREIGN PATENT DOCUMENTS

| | | |
|---|---|---|
| 0158198A1 | 10/1985 | European Pat. Off. . |
| 206 920 A1 | 12/1986 | European Pat. Off. . |
| 334 301 A1 | 9/1989 | European Pat. Off. . |
| WO89/09271 | 10/1989 | WIPO . |
| WO90/07936 | 7/1990 | WIPO . |
| WO91/02805 | 3/1991 | WIPO . |
| WO91/06658 | 5/1991 | WIPO . |
| WO92/05266 | 4/1992 | WIPO . |
| WO93/06867 | 4/1993 | WIPO . |
| WO93/10219 | 5/1993 | WIPO . |
| WO93/10814 | 6/1993 | WIPO . |
| WO93/19191 | 9/1993 | WIPO . |
| WO93/21959 | 11/1993 | WIPO . |
| WO94/04196 | 3/1994 | WIPO . |
| WO94/13824 | 6/1994 | WIPO . |

OTHER PUBLICATIONS

Nishihara K., "A Novel Experimental Approach to Immunotherapy against Malignant Brain Tumor with the Mouse IFN–γ Gene Transfer," *Arch. Jpn. Chir.* 58(1):18–42 (1989). (English abstract).

Culver et al., "In Vivo Gene Transfer with Retroviral Vector–Producer Cells for Treatment of Experimental Brain Tumors," *Science* 256: 1550–1552, 1992.

Panis, Y. et al., "Traitement de tumeurs hepatiques experimentales par transfert de gene suicide in vivo chez le rat," *Comptes Rendus de L'Academie des Sciences: Serie III 315*: 541–544, 1992.

Takamiya et al., "Gene Therapy of Malignant Brain Tumors: A Rat Glioma Line Bearing the Herpes Simplex Virus Type 1–Thymidine Kinase Gene and Wild Type Retrovirus Kills Other Tumor Cells," *Journal of Neuroscience Research* 33(3):493–503, 1992.

Moolten and Wells, "Curability of Tumors Bearing Herpes Thymidine Kinase Genes Transferred by Retroviral Vectors," *Journal of the National Cancer Institute* 82(4): 297–300, 1990.

Moolten, F., "Tumor Chemosensitivity Conferred by Inserted Herpes Thymidine Kinase Genes: Paradigm for a Prospective Cancer Control Strategy," *Cancer Research* 46(10): 5276–5281, 1986.

Ram et al., "In Situ Retroviral–mediated Gene Transfer for the Treatment of Brain Tumors in Rats," *Cancer Research* 53(1): 83–88, 1993.

Georges et al., "Prevention of Orthotopic Human Lung Cancer Growth by Intratracheal Instillation of a Retroviral Antisense K–ras Construct," *Cancer Research* 53(8): 1743–1746, 1993.

Nabel et al., "Direct gene transfer with DNA–liposome complexes in melanoma: Expression, biologic activity, and lack of toxicity in humans," *Proc. Natl. Acad. Sci. USA* 90(23): 11307–11311, 1993.

Jaffe et al., "High Efficiency Gene Transfer into Primary Human Tumor Explants without Cell Selection," *Cancer Research* 53: 2221–2226, 1993.

Colombo and Forni, "Cytokine gene transfer in tumor inhibition and tumor therapy: where are we now?," *Immunology Today* 15(2): 48–51, 1994.

Hock et al., "Interleukin 7 Induces CD4$^+$ Cell–dependent Tumor Rejection," *Journal of Experimental Medicine* 174: 1291–1298, 1991.

Aoki et al., "Expression of murine interleukin 7 in a murine glioma cell line results in reduced tumorigenicity in vivo," *Proc. Natl. Acad. Sci. USA* 89: 3850–3854, 1992.

Stoppacciaro et al., "Regression of an Established Tumor Genetically Modified to Release Granulocyte Colony–stimulating Factor Requires Granulocyte–T Cell Cooperation and T Cell–produced Interferon γ," *Journal of Experimental Medicine* 178: 151–161, 1993.

(List continued on next page.)

*Primary Examiner*—Mindy Fleisher
*Assistant Examiner*—Johnny F. Railey, II
*Attorney, Agent, or Firm*—Seed & Berry; Norman J. Kruse; Robert P. Blackburn

[57] ABSTRACT

The present invention provides methods for inhibiting the growth of selected tumors utilizing recombinant viral vectors. Briefly, within one aspect of the present invention, a method for inhibiting the growth of a selected tumor is provided comprising the step of directly administering to a warm-blooded animal a vector construct which directs the expression of at least one anti-tumor agent, such that the growth of said tumor is inhibited. Representative examples of anti-tumor agents include immune activators and tumor proliferation inhibitors.

4 Claims, 22 Drawing Sheets

OTHER PUBLICATIONS

Dranoff et al., "Vaccination with irradiated tumor cells engineered to secrete murine granulocyte–macrophage colony–stimulating factor stimulates potent, specific, and long–lasting anti–tumor immunity," Proc. Natl. Acad. Sci. USA 90: 3539–3543, 1993.

Colombo et al. "Granulocyte Colony–stimulating Factor Gene Transfer Supresses Tumorigenicity of a Murine Adenocarcinoma In Vivo," Journal of Experimental Medicine 173: 889–897, 1991.

Nabel et al., "Immunotherapy of Malignancy by In Vivo Gene Transfer into Tumors," Human Gene Therapy 3: 339–410, 1992.

Caruso et al., "Regression of established macroscopic liver metastases after in situ transduction of a suicide gene," Proc. Natl. Acad. Sci. 90: 7024–7028, 1993.

Wallach et al., "Preferential effect of γ interferon on the synthesis of HLA antigens and their mRNAs in human cells," Nature 299: 833–836, 1982.

Carrel et al., "Recombinant interferon–γ can induce the expression of HLA–DR and –DC on DR–negative melanoma cells and enhance the expression of HLA–ABC and tumor–associated antigens," European Journal of Immunology 15: 118–123, 1985.

Stevenson, F., "Tumor vaccines," FASEB Journal 5: 2250–2257, 1991.

Tanaka et al., "Rejection of B16 Melanoma Induced by Expression of a Transfected Major Histocompatibility Complex Class I Gene," Mol. Cell. Biol. 8(4): 1857–1861, 1988.

Watanabe et al., "Exogenous expression of mouse interferon γ cDNA in mouse neuroblastoma C1300 cells results in reduced tumorigenicity by augmented anti–tumor immunity," Proc. Natl. Acad. Sci. 86: 9456–9460, 1989.

Nishihara et al., "Augmentation of Tumor Targeting in a Line of Glioma–specific Mouse Cytotoxic T–Lymphocytes by Retroviral Expression of Mouse γ–Interferon Complementary DNA," Cancer Research 48: 4730–4735, 1988.

Darrow et al., "The Role of HLA Class I Antigens In Recognition of Melanoma Cells By Tumor–Specific Cytotoxic T Lymphocytes: Evidence for Shared Tumor Antigens.," Journal of Immunology 142(9): 3329–3335, 1989.

Vose, B., "Quantitation Of Proliferative And Cytotoxic Precursor Cells Directed Against Human Tumours: Limiting Dilution Analysis In Peripheral Blood And At The Tumour Site," International Journal of Cancer 30: 135–142, 1982.

Ioannides et al., "Cytotoxic T Cell Clones Isolated From Ovarian Tumor–Infiltrating Lymphocytes Recognize Multiple Antigenic Epitopes On Autologous Tumor Cells," Journal of Immunology 146: 1700–1707, 1991.

Eglitis et al., "Expression Of Lymphokine Genes Using Retroviral Vectors," Journal of Cellular Biochemistry (Supp. 14A): 367, 1990.

Golumbek et al., "Treatment of Established Renal Cancer by Tumor Cells Engineered to Secrete Interleukin–4," Science 254: 713–716, 1991.

Esumi et al., "Reduced Tumorigenicity of Murine Tumor Cells Secreting γ–Interferon Is Due to Nonspecific Host Responses and Is Unrelated to Class I Major Histocompatibility Complex Expression," Cancer Research 51: 1185–1189, 1991.

Fearon et al., "Interleukin–2 Production by Tumor Cells Bypasses T Helper Function in the Generation of an Anti–tumor Response," Cell 60: 397–403, 1990.

Tepper et al., "Murine Interleukin–4 Displays Potent Anti–Tumor Activity in Vivo," Cell 57: 503–512, 1989.

Fellous et al., "Enhanced expression of HLA antigens and $\beta_2$–microglobulin on interferon–treated human lymphoid cells," European Journal Immunology 9: 446–449, 1979.

Fellous et al., "Interferon–dependent induction of mRNA for the major histocompatibility antigens in human fibroblasts and lymphoblastoid cells," Proc. Natl. Acad. Sci. 79: 3082–3086, 1982.

Alter et al., "Sporadic Non–A, Non–B Hepatitis: Frequency and Epidemiology in an Urban U.S. Population," Journal of Infect. Dis. 145: 886–893, 1982.

Natali et al., "Heterogeneity in the Expression of HLA and Tumor–associated Antigens by Surgically Removed and Cultured Breast Carcinoma Cells," Cancer Research 43: 660–668, 1983.

Collins et al., "Immune interferon activates multiple class II major histocompatibility complex genes and the associated invariant chain gene in human endothelial cells and dermal fibroblasts," Proc. Natl. Acad. Sci. 81:4917–4921, 1984.

Herlyn et al., "Efficient Selection of Human Tumor Growth–Inhibiting Monoclonal Antibodies," Journal of Immunological Methods 73: 157–167, 1984.

Giacomini et al., "A third polypeptide associated with heavy and light chain subunits of class I HLC antigens in immune interferon–treated human melanoma cells," European Journal of Immunology 15: 946–951, 1985.

Yamasaki et al., "Immunoregulatory role in gamma interferon production by a T cell growth factor–dependent experimental malignant glioma–specific cytotoxic T lymphocyte clone," Journal of Neurosurgery 63: 763–770, 1985.

Gerber and Thung, "Biology of Disease: Molecular and Cellular Pathology of Hepatitis B," Lab. Invest. 52: 572–590, 1985.

Norton and Coffin, "Bacterial β–Galactosidase as a Marker of Rous Sarcoma Virus Gene Expression and Replication," Molecular and Cellular Biology 5: 281–290, 1985.

Giacomini et al., "Recombinant Human INF–γ, But Not INF–α Or INF–β, Enhances MHC– and non–MHC–Encoded Glycoproteins By A Protein Synthesis–Dependent Mechanism," Journal of Immunology 140: 3073–3081, 1988.

Lapierre et al., "Three Distinct Classes Of Regulatory Cytokines Control Endothelial Cell MHC Antigen Expression: Interactions with Immune γ Interferon Differentiate the Effects of Tumor Necrosis Factor and Lymphotoxin from those of Leukocyte α and Fibroblast β Interferons," Journal of Experimental Medicine 167: 794–804, 1988.

Bystryn, J., "Vaccine Immunotherapy of Melanoma," 1989, pp. 513–530.

Imawari et al., "Establishment of a human T–cell clone cytotoxic for both autologous and allogeneic hepatocytes from chronic hepatitis patients with type non–A, non–B virus," Proc. Natl. Acad. Sci. 85: 2883–2887, 1989.

Sanchez and Holmgren, "Recombinant system for overexpression of cholera toxin B subunit in Vibrio cholerae as a basis for vaccine development," Proc. Natl. Acad. Sci. 86: 481–485, 1989.

Berd et al., "Treatment of Metastatic Melanoma With an Autologous Tumor–Cell Vaccine: Clinical and Immunologic Results in 64 Patients," Journal of Clin. Onc. 8: 1858–1867, 1990.

Gansbacher et al., "Interleukin 2 Gene Transfer into Cells Abrogates Tumorigenicity and Induces Protective Immunity," *Journal of Experimental Medicine* 172: 1217–1224, 1990.

Miyatake et al., "Efficient Tumor Suppression by Glioma-Specific Murine Cytotoxic T Lymphocytes Transfected With Interferon-γ Gene," *Journal of the National Cancer Institute* 82:217–220, 1990.

Takeuchi et al., "Nucleotide sequence of core and envelope genes of the heatitis C virus genome derived directly from human healthy carriers," *Nucleic Acids Research* 18: 4626, 1990.

Küster et al., "Characterization and Expression of the Gene for the Human Fc Receptor γ Subunit," *Journal of Biological Chemistry* 265: 6448–6452, 1990.

Partridge, T., "Muscle transfection made easy," *Nature* 352:757–758, 1991.

Farci et al., "A Long–Term Study Of Hepatitis C Virus Replication In Non–A, Non–B Hepatitis," *New England Journal of Medicine* 325: 98–104, 1991.

Fuchs et al., "Characterization of nucleotide sequences from European hepatitis C virus isolates," *Gene* 103: 163–169, 1991.

Kaklamani et al., "Hepatitis B and C Viruses and Their Interaction in the Origin of Hepatocellular Carcinoma," *JAMA* 265: 1974–1976, 1991.

Tanaka et al., "Hepatitis C and Hepatitis B in the Etiology of Hepatocellular Carcinoma in the Japanese Population," *Cancer Research* 51: 2842–2847, 1991.

Wood et al., "Preproabrin: genomic cloning, characterisation and the expression of the A–chain in *Escherichia coli*," *European Journal of Biochemistry* 198:723–732, 1991.

Lin et al., "Isolation and characterization of a cDNA clone encoding the anti–viral protein from *Phytolacca americana*," *Plant Molecular Biology* 17: 609–614, 1991.

Adam et al., "Internal Initiation of Translation in Retroviral Vectors Carrying Picornavirus 5' Nontranslated Regions," *Journal of Virology* 65: 4985–4990, 1991.

Giavedoni et al., "Vaccinia virus recombinants expressing chimeric proteins of human immunodeficiency virus and γ interferon are attenuated for nude mice," *Proc Natl. Acad. Sci.* 89: 3409–3413, 1992.

Bass et al., "Heterogeneous Mechanisms Of Human Cytotoxic T Lymphocyte Generation. I. Differential Helper Cell Requirements for the Generation of Cytotoxic Effector Cells from $CD8^+$ Precursor Subpopulations," *Journal of Immunology* 149:2489–2495, 1992.

Routes, J., "IFN Increases Class I MHC Antigen Expression On Adenovirus–Infected Human Cells Without Induing Resistance To Natural Killer Cell Killing," *Journal of Immunology* 149: 2372–2377, 1992.

Gazit et al., "Chemo–adoptive immunotherapy of nude mice implanted with human colorectal carcinoma and melanoma cell lines," *Cancer Immunology and Immunotherapy* 35: 135–144, 1992.

Hwu et al., "Functional and Molecular Characterization of Tumor–Infiltrating Lymphocytes Transduced with Tumor Necrosis Factor–α cDNA for the Gene Therapy of Cancer in Humans," *Journal of Immunology* 150(9):n4104–4115, 1993.

Gastl et al., "Retroviral Vector–mediated Lymphokine Gene Transfer into Human Renal Cancer Cells," *Cancer Research* 52(22): 6229–6236, 1992.

Walker, P.M.B. (Ed.), *Chambers Science and Technology Dictionary*, W & R Chambers Ltd. and Cambridge University Press, 1988, pp. 538, column 2, line 54–59.

A.L. Asher et al. (1991) J. Immunol. 146(9):3227–3234.

T. Blankenstein et al. (1991) J. Exp. Med. 173:1047–1052.

D. Cournoyer et al. (1993) Annv. Rev. Immunol. 11:297–329.

N.J. Crowley et al. (1990) Cancer Research 50:492–498.

T. Friedmann (1992) Cancer Supplement 70(6):1810–1817.

B. Gansbacher et al. (1990) Cancer Research 50:7820–7825.

A.A. Gutierrez et al. (1992) The Lancet 339:715–721.

A. Knuth et al. (1991) Current Opinion in Immunology 3:659–664.

F.D. Ledley (1991) Human Gene Therapy 2:77–83.

A. Porgador et al. (1992) Cancer Research 52:3679–3686.

Z. Ram et al. (1994) J. Neurosurg. 80:535–540.

N.P. Restifo et al. (1992) J. Exp. Med. 175:1423–1431.

S.J. Russell (1990) Immunology Today 11(6):196–200.

M.N. Teng et al. (1991) Proc. Natl. Acad. Sci. USA 88:3535–3539.

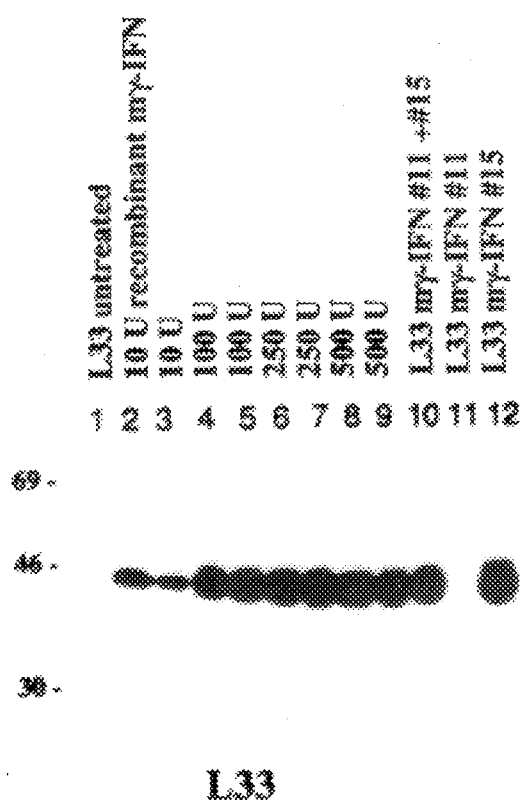
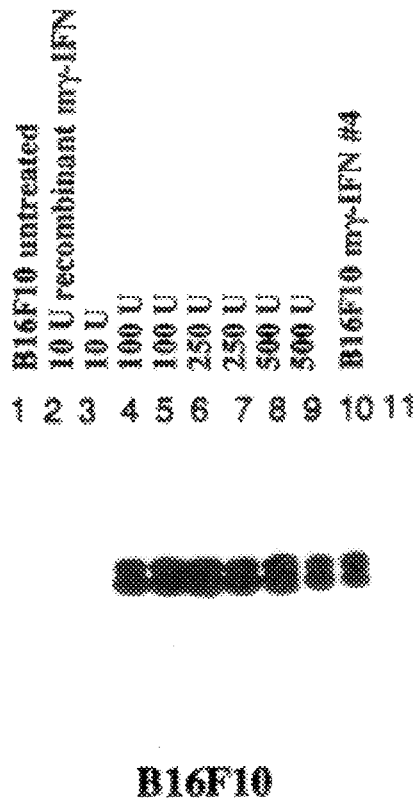
FIG. 3A
FIG. 3B

HUMAN MELANOMA TRANSDUCIBILITY - DM252
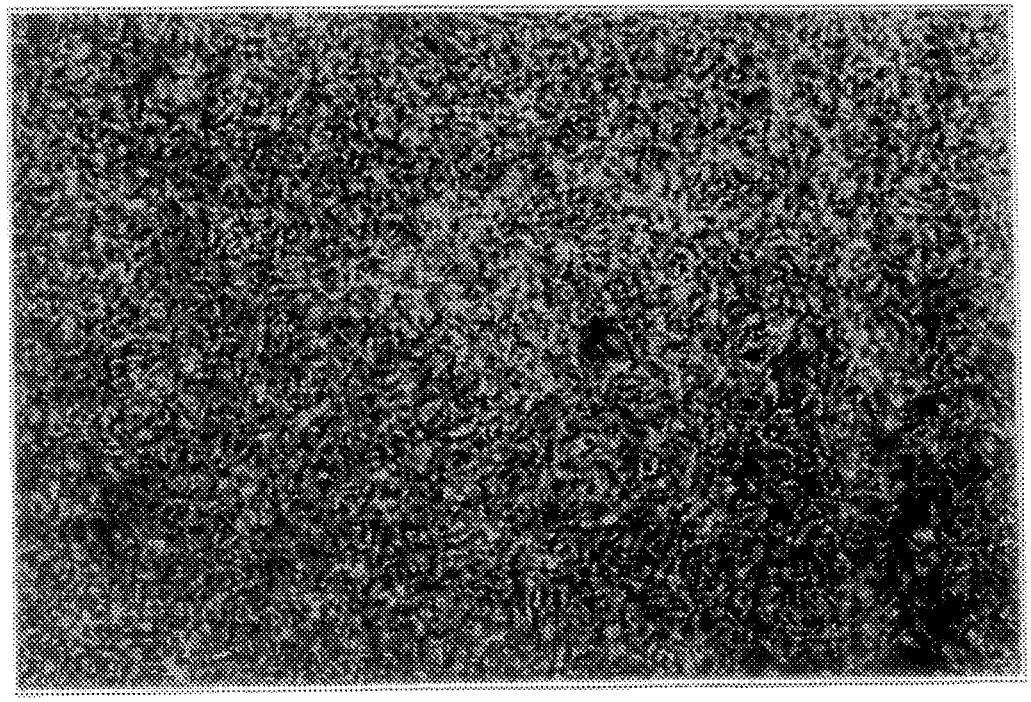
FIG. 25A  NON-TRANSDUCED
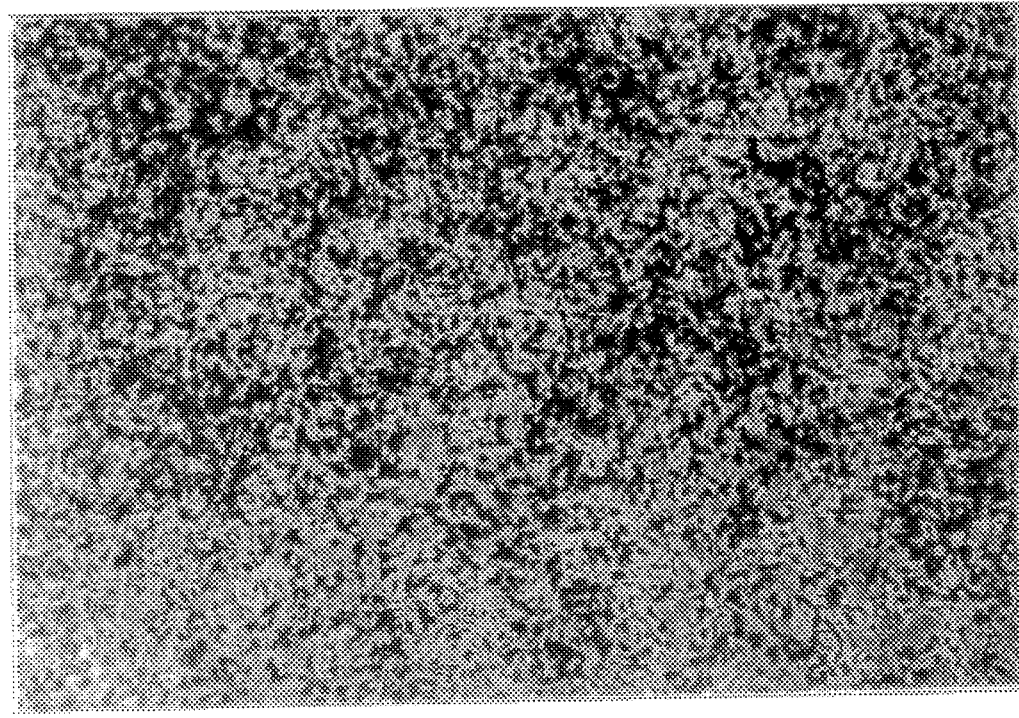
FIG. 25B  TRANSDUCED AT MOI OF 1

SEQUENCE LISTING ( 1 ) GENERAL INFORMATION:

( i i i ) NUMBER OF SEQUENCES: 36

( 2 ) INFORMATION FOR SEQ ID NO:1:

( i ) SEQUENCE CHARACTERISTICS:
　　　　　　　　( A ) LENGTH: 21 base pairs
　　　　　　　　( B ) TYPE: nucleic acid
　　　　　　　　( C ) STRANDEDNESS: single
　　　　　　　　( D ) TOPOLOGY: linear ( i i ) MOLECULE TYPE: cDNA ( i i i ) HYPOTHETICAL: NO ( v ) FRAGMENT TYPE: N-terminal ( x i ) SEQUENCE DESCRIPTION: SEQ ID NO:1:

TAATAAATAG ATTTAGATTT A　　　　　　　　　　　　　　　　　　　　　　　　　　21

( 2 ) INFORMATION FOR SEQ ID NO:2:

( i ) SEQUENCE CHARACTERISTICS:
　　　　　　　　( A ) LENGTH: 35 base pairs
　　　　　　　　( B ) TYPE: nucleic acid
　　　　　　　　( C ) STRANDEDNESS: single
　　　　　　　　( D ) TOPOLOGY: linear ( i i ) MOLECULE TYPE: cDNA ( i i i ) HYPOTHETICAL: NO ( v ) FRAGMENT TYPE: N-terminal ( x i ) SEQUENCE DESCRIPTION: SEQ ID NO:2:

GCCTCGAGAC GATGAAATAT ACAAGTTATA TCTTG　　　　　　　　　　　　　　　　35

( 2 ) INFORMATION FOR SEQ ID NO:3:

( i ) SEQUENCE CHARACTERISTICS:
　　　　　　　　( A ) LENGTH: 35 base pairs
　　　　　　　　( B ) TYPE: nucleic acid
　　　　　　　　( C ) STRANDEDNESS: single
　　　　　　　　( D ) TOPOLOGY: linear ( i i ) MOLECULE TYPE: cDNA ( i i i ) HYPOTHETICAL: NO ( v ) FRAGMENT TYPE: N-terminal ( x i ) SEQUENCE DESCRIPTION: SEQ ID NO:3:

GAATCGATCC ATTACTGGGA TGCTCTTCGA CCTGG　　　　　　　　　　　　　　　　35

( 2 ) INFORMATION FOR SEQ ID NO:4:

( i ) SEQUENCE CHARACTERISTICS:
　　　　　　　　( A ) LENGTH: 21 base pairs
　　　　　　　　( B ) TYPE: nucleic acid
　　　　　　　　( C ) STRANDEDNESS: single
　　　　　　　　( D ) TOPOLOGY: linear ( i i ) MOLECULE TYPE: cDNA ( i i i ) HYPOTHETICAL: NO ( v ) FRAGMENT TYPE: N-terminal ( x i ) SEQUENCE DESCRIPTION: SEQ ID NO:4:

ATAAATAGAA GGCCTGATAT G　　　　　　　　　　　　　　　　　　　　　　　　　21

( 2 ) INFORMATION FOR SEQ ID NO:5:

( i ) SEQUENCE CHARACTERISTICS:
    ( A ) LENGTH: 35 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( v ) FRAGMENT TYPE: N-terminal ( x i ) SEQUENCE DESCRIPTION: SEQ ID NO:5:

```
GCCTCGAGAC  AATGTACAGG  ATGCAACTCC  TGTCT                              35
```

( 2 ) INFORMATION FOR SEQ ID NO:6:

( i ) SEQUENCE CHARACTERISTICS:
    ( A ) LENGTH: 35 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( v ) FRAGMENT TYPE: N-terminal ( x i ) SEQUENCE DESCRIPTION: SEQ ID NO:6:

```
GAATCGATTT  ATCAAGTCAG  TGTTGAGATG  ATGCT                              35
```

( 2 ) INFORMATION FOR SEQ ID NO:7:

( i ) SEQUENCE CHARACTERISTICS:
    ( A ) LENGTH: 6 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( v ) FRAGMENT TYPE: N-terminal ( x i ) SEQUENCE DESCRIPTION: SEQ ID NO:7:

```
Gly  Arg  Arg  Ala  Ser  Gln
1                    5
```

( 2 ) INFORMATION FOR SEQ ID NO:8:

( i ) SEQUENCE CHARACTERISTICS:
    ( A ) LENGTH: 12 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( v ) FRAGMENT TYPE: N-terminal ( x i ) SEQUENCE DESCRIPTION: SEQ ID NO:8:

```
Leu  Gly  Glu  Pro  Gln  Leu  Cys  Tyr  Ile  Leu  Asp  Ala
1                    5                        10
```

( 2 ) INFORMATION FOR SEQ ID NO:9:

( i ) SEQUENCE CHARACTERISTICS:
    ( A ) LENGTH: 13 amino acids ( B ) TYPE: amino acid
( C ) STRANDEDNESS: single
( D ) TOPOLOGY: linear ( i i ) MOLECULE TYPE: peptide ( i i i ) HYPOTHETICAL: NO ( v ) FRAGMENT TYPE: N-terminal ( x i ) SEQUENCE DESCRIPTION: SEQ ID NO:9:

```
Gly Arg Arg Ala Ser Gln Leu Cys Tyr Ile Leu Asp Ala
1               5                   10
```

( 2 ) INFORMATION FOR SEQ ID NO:10:

( i ) SEQUENCE CHARACTERISTICS:
( A ) LENGTH: 9 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( v ) FRAGMENT TYPE: N-terminal ( x i ) SEQUENCE DESCRIPTION: SEQ ID NO:10:

```
Lys Ala Ala Ile Thr Ser Tyr Glu Lys
1               5
```

( 2 ) INFORMATION FOR SEQ ID NO:11:

( i ) SEQUENCE CHARACTERISTICS:
( A ) LENGTH: 9 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( v ) FRAGMENT TYPE: N-terminal ( x i ) SEQUENCE DESCRIPTION: SEQ ID NO:11:

```
Lys Ala Ala Ile Thr Glu Thr Leu Lys
1               5
```

( 2 ) INFORMATION FOR SEQ ID NO:12:

( i ) SEQUENCE CHARACTERISTICS:
( A ) LENGTH: 31 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( v ) FRAGMENT TYPE: N-terminal ( x i ) SEQUENCE DESCRIPTION: SEQ ID NO:12:

CAGGACCCAT ATGTAAAAGA AGCAGAAAAC C                                31

( 2 ) INFORMATION FOR SEQ ID NO:13:

( i ) SEQUENCE CHARACTERISTICS:
( A ) LENGTH: 27 base pairs
( B ) TYPE: nucleic acid ( C ) STRANDEDNESS: single
              ( D ) TOPOLOGY: linear ( i i ) MOLECULE TYPE: cDNA ( i i i ) HYPOTHETICAL: NO ( v ) FRAGMENT TYPE: N-terminal ( x i ) SEQUENCE DESCRIPTION: SEQ ID NO:13:

GCAGAGCTGG GATGCTCTTC GACCTCG                                                              2 7

( 2 ) INFORMATION FOR SEQ ID NO:14:

( i ) SEQUENCE CHARACTERISTICS:
              ( A ) LENGTH: 30 base pairs
              ( B ) TYPE: nucleic acid
              ( C ) STRANDEDNESS: single
              ( D ) TOPOLOGY: linear ( i i ) MOLECULE TYPE: cDNA ( i i i ) HYPOTHETICAL: NO ( v ) FRAGMENT TYPE: N-terminal ( x i ) SEQUENCE DESCRIPTION: SEQ ID NO:14:

GCATCCCAGC TCTGCTATAT CCTGGATGCC                                                           3 0

( 2 ) INFORMATION FOR SEQ ID NO:15:

( i ) SEQUENCE CHARACTERISTICS:
              ( A ) LENGTH: 27 base pairs
              ( B ) TYPE: nucleic acid
              ( C ) STRANDEDNESS: single
              ( D ) TOPOLOGY: linear ( i i ) MOLECULE TYPE: cDNA ( i i i ) HYPOTHETICAL: NO ( v ) FRAGMENT TYPE: N-terminal ( x i ) SEQUENCE DESCRIPTION: SEQ ID NO:15:

GGCATGCAGG CATATGTGAT GCCAACC                                                              2 7

( 2 ) INFORMATION FOR SEQ ID NO:16:

( i ) SEQUENCE CHARACTERISTICS:
              ( A ) LENGTH: 30 base pairs
              ( B ) TYPE: nucleic acid
              ( C ) STRANDEDNESS: single
              ( D ) TOPOLOGY: linear ( i i ) MOLECULE TYPE: cDNA ( i i i ) HYPOTHETICAL: NO ( v ) FRAGMENT TYPE: N-terminal ( x i ) SEQUENCE DESCRIPTION: SEQ ID NO:16:

CAGAGTCTCG GTTATAGCTG CCTTTCGCAC                                                           3 0

( 2 ) INFORMATION FOR SEQ ID NO:17:

( i ) SEQUENCE CHARACTERISTICS:
              ( A ) LENGTH: 27 base pairs
              ( B ) TYPE: nucleic acid
              ( C ) STRANDEDNESS: single
              ( D ) TOPOLOGY: linear ( i i ) MOLECULE TYPE: cDNA ( i i i ) HYPOTHETICAL: NO ( v ) FRAGMENT TYPE: N-terminal ( x i ) SEQUENCE DESCRIPTION: SEQ ID NO:17:

GCTATAACCG AGACTCTGAA GCATGAG 27

( 2 ) INFORMATION FOR SEQ ID NO:18:

( i ) SEQUENCE CHARACTERISTICS:
    ( A ) LENGTH: 6 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( v ) FRAGMENT TYPE: N-terminal ( x i ) SEQUENCE DESCRIPTION: SEQ ID NO:18:

Gly Arg Arg Ala Ser Gln
1               5

( 2 ) INFORMATION FOR SEQ ID NO:19:

( i ) SEQUENCE CHARACTERISTICS:
    ( A ) LENGTH: 11 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( v ) FRAGMENT TYPE: N-terminal ( x i ) SEQUENCE DESCRIPTION: SEQ ID NO:19:

Leu Val Thr Asn Ser Ala Pro Thr Ser Ser Ser
1               5                   10

( 2 ) INFORMATION FOR SEQ ID NO:20:

( i ) SEQUENCE CHARACTERISTICS:
    ( A ) LENGTH: 12 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( v ) FRAGMENT TYPE: N-terminal ( x i ) SEQUENCE DESCRIPTION: SEQ ID NO:20:

Gly Arg Arg Ala Ser Gln Ala Pro Thr Ser Ser Ser
1               5                   10

( 2 ) INFORMATION FOR SEQ ID NO:21:

( i ) SEQUENCE CHARACTERISTICS:
    ( A ) LENGTH: 6 amino acids
    ( B ) TYPE: amino acid
    ( C ) STRANDEDNESS: single
    ( D ) TOPOLOGY: linear ( i i ) MOLECULE TYPE: peptide (iii) HYPOTHETICAL: NO (v) FRAGMENT TYPE: N-terminal (xi) SEQUENCE DESCRIPTION: SEQ ID NO:21:

```
Ile Ile Ser Thr Leu Thr
1               5
```

(2) INFORMATION FOR SEQ ID NO:22:

(i) SEQUENCE CHARACTERISTICS:
(A) LENGTH: 11 amino acids
(B) TYPE: amino acid
(C) STRANDEDNESS: single
(D) TOPOLOGY: linear (ii) MOLECULE TYPE: peptide (iii) HYPOTHETICAL: NO (v) FRAGMENT TYPE: N-terminal (xi) SEQUENCE DESCRIPTION: SEQ ID NO:22:

```
Val Leu Gly Ser Leu Gly Cys Tyr Cys Gln Asp
1               5                   10
```

(2) INFORMATION FOR SEQ ID NO:23:

(i) SEQUENCE CHARACTERISTICS:
(A) LENGTH: 11 amino acids
(B) TYPE: amino acid
(C) STRANDEDNESS: single
(D) TOPOLOGY: linear (ii) MOLECULE TYPE: peptide (iii) HYPOTHETICAL: NO (v) FRAGMENT TYPE: N-terminal (xi) SEQUENCE DESCRIPTION: SEQ ID NO:23:

```
Ile Ile Ser Thr Leu Thr Cys Tyr Cys Gln Asp
1               5                   10
```

(2) INFORMATION FOR SEQ ID NO:24:

(i) SEQUENCE CHARACTERISTICS:
(A) LENGTH: 28 base pairs
(B) TYPE: nucleic acid
(C) STRANDEDNESS: single
(D) TOPOLOGY: linear (ii) MOLECULE TYPE: cDNA (iii) HYPOTHETICAL: NO (v) FRAGMENT TYPE: N-terminal (xi) SEQUENCE DESCRIPTION: SEQ ID NO:24:

```
CAGGACCCAT ATGTAAAAGA AGCAGAAG                                    28
```

(2) INFORMATION FOR SEQ ID NO:25:

(i) SEQUENCE CHARACTERISTICS:
(A) LENGTH: 29 base pairs
(B) TYPE: nucleic acid
(C) STRANDEDNESS: single
(D) TOPOLOGY: linear (ii) MOLECULE TYPE: cDNA (iii) HYPOTHETICAL: NO ( v ) FRAGMENT TYPE: N-terminal ( x i ) SEQUENCE DESCRIPTION: SEQ ID NO:25:

GGTGCACTCT GGGATGCTCT TCGACCTCG                                                29

( 2 ) INFORMATION FOR SEQ ID NO:26:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( v ) FRAGMENT TYPE: N-terminal ( x i ) SEQUENCE DESCRIPTION: SEQ ID NO:26:

CCCAGGCACC TACTTCAAGT TCTACAAAG                                                29

( 2 ) INFORMATION FOR SEQ ID NO:27:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( v ) FRAGMENT TYPE: N-terminal ( x i ) SEQUENCE DESCRIPTION: SEQ ID NO:27:

GGGTCTTAAG TGAAAGTTTT TGCTTTGAGC                                               30

( 2 ) INFORMATION FOR SEQ ID NO:28:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( v ) FRAGMENT TYPE: N-terminal ( x i ) SEQUENCE DESCRIPTION: SEQ ID NO:28:

CATCTTCAGT GTCTAGAAGA AGAACTC                                                  27

( 2 ) INFORMATION FOR SEQ ID NO:29:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( v ) FRAGMENT TYPE: N-terminal ( x i ) SEQUENCE DESCRIPTION: SEQ ID NO:29:

GGCAGTAACA AGTCAGTGTT GAGATGATGC                                               30

( 2 ) INFORMATION FOR SEQ ID NO:30:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( v ) FRAGMENT TYPE: N-terminal ( x i ) SEQUENCE DESCRIPTION: SEQ ID NO:30:

GTGACTGATG TTACTGCCAG GACCCATATG                                               30

( 2 ) INFORMATION FOR SEQ ID NO:31:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( v ) FRAGMENT TYPE: N-terminal ( x i ) SEQUENCE DESCRIPTION: SEQ ID NO:31:

CGAATAATTA GTCAGCTTTT CGAAGTC                                                  27

( 2 ) INFORMATION FOR SEQ ID NO:32:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( v ) FRAGMENT TYPE: N-terminal ( x i ) SEQUENCE DESCRIPTION: SEQ ID NO:32:

GCCTCGAGCT CGAGCGATGA AATATACAAG TTATATCTTG                                    40

( 2 ) INFORMATION FOR SEQ ID NO:33:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( v ) FRAGMENT TYPE: N-terminal ( x i ) SEQUENCE DESCRIPTION: SEQ ID NO:33:

GTCATCTCGT TTCTTTTTGT TGCTATT                                                  27

(2) INFORMATION FOR SEQ ID NO:34:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (v) FRAGMENT TYPE: N-terminal (xi) SEQUENCE DESCRIPTION: SEQ ID NO:34:

ATTAGCAACA AAAAGAAACG AGATGAC     27

(2) INFORMATION FOR SEQ ID NO:35:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (v) FRAGMENT TYPE: N-terminal (xi) SEQUENCE DESCRIPTION: SEQ ID NO:35:

GCATCGATAT CGATCATTAC TGGGATGCTC TTCGACCTCG     40

(2) INFORMATION FOR SEQ ID NO:36:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: N-terminal (xi) SEQUENCE DESCRIPTION: SEQ ID NO:36:

Gln Glu Thr Tyr Glu Thr Leu Lys
    1                 5

COMPOSITIONS AND METHODS FOR CANCER IMMUNOTHERAPY

CROSS REFERENCE TO RELATED APPLICATIONS

This application is a continuation-in-part of U.S. application Ser. No. 07/965,084, filed Oct. 22, 1992, (now abandoned) which is a continuation of U.S. application Ser. No. 07/586,603 filed Sep. 21, 1990 (now abandoned), which is a continuation-in-part of U.S. application Ser. No. 07/565,606, filed Aug. 10, 1990 (now abandoned), which is a continuation-in-part of U.S. application Ser. No. 07/395,932, filed Aug. 18, 1989, (now abandoned) which is a continuation-in-part of U.S. application Ser. No. 07/170,515, filed Mar. 21, 1988 (now abandoned).

TECHNICAL FIELD

The present invention relates generally to the field of cancer immunotherapeutics, and more specifically, to methods of inhibiting the growth of a selected tumor utilizing vector, constructs.

BACKGROUND OF THE INVENTION

Cancer accounts for one-fifth of the total mortality in the United States, and is the second leading cause of death. Cancer is typically characterized by the uncontrolled division of a population of cells. This uncontrolled division typically leads to the formation of a tumor, which may subsequently metastasize to other sites.

Primary solid tumors can generally be treated by surgical resection. However, the majority of patients which have solid tumors also possess micrometastases beyond the primary tumor site. If treated with surgery alone, approximately 70% of these patients will experience recurrence of the cancer. In addition to surgery, many cancers are now also treated with a combination of therapies involving cytotoxic chemotherapeutic drugs (e.g., Vincristine, vinblastine, cisplatin, methotrexate, 5-FU, etc.) and/or radiation therapy. One difficulty with this approach however, is that radiotherapeutic and chemotherapeutic agents are toxic to normal tissues, and often create life-threatening side effects. In addition, these approaches often have extremely high failure/remission rates (up to 90% depending upon the type of cancer).

In addition to chemo- and radiation therapies, many have attempted to bolster or augment an individual's own-immune system in order to eliminate the cancer cells. Several immunotherapies have utilized bacterial or viral components as adjuvants, in order to stimulate the immune system to destroy the tumor cells. Examples of such components include BCG, endotoxin, mixed bacterial vaccines, interferons ($\alpha$, $\beta$, and $\gamma$), interferon inducers (e.g., *Brucella abortus*, and various viruses), and thymic factors (e.g., thymosin fraction 5, and thymosin alpha-1) (see generally "Principles of Cancer Biotherapy," Oldham (ed.), Raven Press, New York, 1987). Such agents have generally been useful as adjuvants and as nonspecific stimulants in animal tumor models, but have not yet proved to be generally effective in humans.

Lymphokines have also been utilized in the treatment of cancer. Briefly, lymphokines are secreted by a variety of cells, and generally have an effect on specific cells in the generation of an immune response. Examples of lymphokines include Interleukins (IL)-1, -2, -3, and -4, as well as colony stimulating factors such as G-CSF, GM-CSF, and M-CSF. Recently, one group has utilized IL-2 to stimulate peripheral blood cells in order to expand and produce large quantities of cells which are cytotoxic to tumor cells (Rosenberg et al., *N. Engl. J. Med.* 313:1485–1492, 1985).

Others have suggested the use of antibody-mediated anti-cancer therapies. Briefly, antibodies may be developed which recognize certain cell surface antigens that are either unique, or more prevalent on cancer cells compared to normal cells. These antibodies, or "magic bullets," may be utilized either alone or conjugated with a toxin in order to specifically target and kill tumor cells (Dillman, "Antibody Therapy," *Principles of Cancer Biotherapy*, Oldham (ed.), Raven Press, Ltd., New York, 1987). For example, Ball et al. (Blood 62:1203–1210, 1983) treated several patients with acute myelogenous leukemia with one or more of several monoclonal antibodies specific for the leukemia, resulting in a marked decrease in circulating leukemia cells during treatment. Similarly, others have utilized toxin-conjugated antibodies therapeutically to treat a variety of tumors, including, for example, melanomas, colorectal carcinomas, prostate carcinomas, breast carcinomas, and lung carcinomas (see Dillman, supra). One difficulty however, is that most monoclonal antibodies are of murine origin, and thus hypersensitivity against the murine antibody may limit its efficacy, particularly after repeated therapies. Common side effects include fever, sweats and chills, skin rashes, arthritis, and nerve palsies.

Therefore, compositions and methods which augment natural host defenses against tumor induction or progression without the cytotoxic side effects of prior methods, may increase remission rates and enhance survival of patients with cancer. The present invention provides such compositions and methods, and further provides other related advantages.

SUMMARY OF THE INVENTION

Briefly stated, the present invention is directed towards methods for inhibiting the growth of a selected tumor. Within one aspect of the invention, a method is provided for inhibiting the growth of a selected tumor in a warm-blooded animal, comprising the step of directly administering to the tumor a vector construct which directs the expression of at least one anti-tumor agent, such that the growth of the tumor is inhibited. Within one embodiment of the invention, the vector construct is carried: by a recombinant viral vector. Within a preferred embodiment, the recombinant viral vector is a recombinant retroviral vector.

Within one embodiment of the invention, the anti-tumor agent is selected from the group consisting of immune activators and tumor proliferation inhibitors. Immune activators include, for example, immune modulators and lymphokines. Representative examples of immune modulators include CD3, ICAM-1, ICAM-2, LFA-1, LFA-3, $\beta$-2-microglobulin, chaperones, alpha interferon and gamma interferon, B7/BB1 and major histocompatibility complex (MHC). Representative examples of lymphokines include gamma-interferon tumor necrosis factor, IL-1, IL-2, IL-3, IL-4, IL-5, IL-6, IL-7, IL-8, IL-9, IL-10, IL-11, GM-CSF, CSF-1, and G-CSF. As noted above, within other embodiments of the invention, anti-tumor agents include tumor proliferation inhibitors such as, for example, toxins and antisense sequences. Representative examples of toxins include ricin, abrin, diphtheria toxin, cholera toxin, gelonin, pokeweed, antiviral protein, tritin, Shigella toxin, and Pseudomonas exotoxin Ph herpes simplex virus thyroidine kinase (HSVTK), and *E. coli* guanine phosphoribosyl transferase. Representative examples of antisense sequences include antisense thymidine kinase, antisense dihydrofolate reductase, antisense HER2, antisense ABL, antisense Myc, and antisense ras.

Within a particularly preferred embodiment of the invention, the anti-tumor agent is a membrane anchor—gamma interferon fusion protein. Within another embodiment, the anti-tumor agent is a gamma interferon—Interleukin-2 fusion protein.

Within additional aspects of the present invention, isolated DNA sequences are provided which encode membrane anchor—gamma interferon fusion proteins and membrane anchor—anti-tumor agent fusion proteins, as well as vector constructs which direct the expression of these sequences, and recombinant viral and retroviral vectors which carry the vector construct. Also provided are recombinant viral vectors and recombinant retroviral vectors carrying a vector construct which directs the expression of an Interleukin-2—gamma interferon fusion protein.

Also provided by the present invention are target cells infected with the recombinant retroviral vectors discussed above, as well as pharmaceutical compositions comprising the above described recombinant viral or retroviral vectors, in combination with a pharmaceutically acceptable carrier or diluent.

Within another aspect of the present invention, methods for inhibiting the growth of a selected tumor in a warm-blooded animal are provided, comprising the step of delivering to a warm-blooded animal a recombinant retroviral or viral vector as described above, such that the growth of the tumor is inhibited.

Within another aspect of the present invention, additional methods for inhibiting the growth of a selected tumor in a warm-blooded animal are provided, comprising the steps of (a) removing tumor cells associated with the selected tumor from a warm-blooded animal, (b) infecting the removed cells with a recombinant retroviral or viral vector as described above, and (c) delivering the infected cells to a warm-blooded animal, such that the growth of the selected tumor is inhibited. Within various embodiments of the invention, prior to the step of delivering, fibroblasts may be depleted from the removed cells. In addition, prior to delivering the infected cells to a warm-blooded animal, the infected cells may be inactivated.

Within yet another aspect of the present invention, a method for inhibiting the growth of a selected tumor in a warm-blooded animal is provided, comprising the steps of (a) removing tumor cells associated with the selected tumor from a warm-blooded animal, (b) contacting the cells with a vector construct which directs the expression of an anti-tumor agent such that the cells are capable of expressing said anti-tumor agent, and (c) delivering the cells from step (b) to an allogeneic warm-blooded animal, such that the growth of the selected tumor is inhibited.

These and other aspects of the present invention will become evident upon reference to the following detailed description and attached drawings.

BRIEF DESCRIPTION OF THE DRAWINGS

FIGS. 3A and 3B are Western blots which depict MHC Class I expression in L33 and B16F10 cells treated with recombinant murine gamma-interferon in vitro.

FIGS. 25A and 25B are high magnification photographs of melanoma cells transducer with vector.

DETAILED DESCRIPTION OF THE INVENTION

Figure 1A:
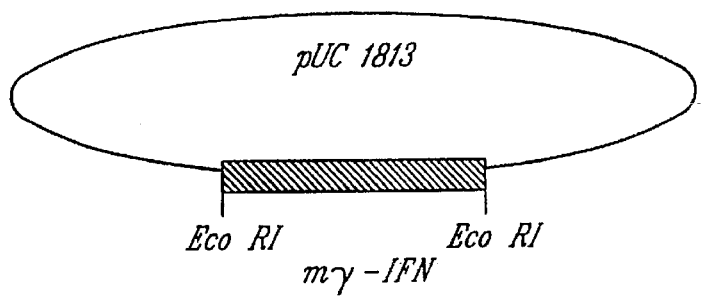
FIGS. 1A, 1B, and 1C schematically illustrate the cloning of murine gamma-interferon into a replication defective retroviral vector.

As noted above, the present invention is directed generally towards methods of inhibiting the growth of a selected tumor utilizing vector constructs which direct the expression of an anti-tumor agent. Briefly, the ability to recognize and defend against foreign pathogens such as tumor cells is central to the function of the immune system. This system, through immune recognition, is capable of distinguishing "self" from "nonself" (foreign), and is essential to ensure that defensive mechanisms are directed towards invading entities rather than against host tissues. The methods which are described in greater detail below provide an effective means of inducing MHC unrestricted response, potent Class I-restricted or Class II-restricted protective and therapeutic CTL responses, as well as humoral responses.

In particular, the present invention provides methods for inhibiting the growth of a selected tumor in a warm-blooded animal, comprising the step of directly administering to the tumor a vector construct which directs the expression of at least one anti-tumor agent, such that the growth of the tumor is inhibited. Within the context of the present invention, "inhibiting the growth of a selected tumor" refers to either (1) the direct inhibition of tumor cell division, or (2) immune cell mediated tumor cell lysis, or both, which leads to a suppression in the net expansion of tumor cells. Inhibition of tumor growth by either of these two mechanisms may be readily determined by one of ordinary skill in the an based upon a number of well known methods. For example, tumor inhibition may be determined by measuring the actual tumor size over a period of time. Alternatively, tumor inhibition may be determined by estimating the size of a tumor (over a period of time) utilizing methods well known to those of skill in the art. More specifically, a variety of radiologic imaging methods (e.g., single photon and positron emission computerized tomography; see generally, "Nuclear Medicine in Clinical Oncology," Winkler, C. (ed.) Springer-Verlag, New York, 1986), may be utilized to estimate tumor size. Such methods may also utilize a variety of imaging agents, including for example, conventional imaging agents (e.g., Gallium-67 citrate), as well as specialized reagents for metabolite imaging, receptor imaging, or immunologic imaging (e.g., radiolabeled monoclonal antibody specific tumor markers). In addition, non-radioactive methods such as ultrasound (see, "Ultrasonic Differential Diagnosis of Tumors", Kossoff and Fukuda, (eds.), Igaku-Shoin, New York, 1984), may also be utilized to estimate the size of a tumor.

In addition to the in vivo methods for determining tumor inhibition discussed above, a variety of in vitro methods may be utilized in order to predict in vivo tumor inhibition. Representative examples include lymphocyte mediated anti-tumor cytolytic activity determined for example, by a $^{51}Cr$ release assay, tumor dependent lymphocyte proliferation (Ioannides et al., *J. Immunol.* 146(5):1700–1707, 1991), in vitro generation of tumor specific antibodies (Herlyn et al., *J. Immunol. Meth.* 73:157–167, 1984), cell (e.g., CTL, helper T cell) or humoral (e.g., antibody) mediated inhibition of cell growth in vitro (Gazit et al., *Cancer Immunol. Immunother* 35:135–144, 1992), and, for any of these assays, determination of cell precursor frequency (Vose, *Int. J. Cancer* 30:135–142 (1982).

Alternatively, for other forms of cancer, inhibition of tumor growth may be determined based upon a change in the presence of a tumor marker. Examples include prostate specific antigen ("PSA") for the detection of prostate cancer (see, U.S. Pat. No. Re. 33,405), and Carcino-Embryonic Antigen ("CEA") for the detection of colorectal and certain breast cancers. For yet other types of cancers such as leukemia, inhibition of tumor growth may be determined based upon the decreased numbers of leukemic cells in a representative blood cell count.

A variety of tumors may be selected for treatment in accordance with the methods described herein. In general, solid tumors are preferred, although leukemias and lymphomas may also be treated if they have developed a solid mass, or if suitable tumor associated markers exist such that the tumor cells can be physically separated from nonpathogenic normal cells. For example, acute lymphocytic leukemia cells may be sorted from other lymphocytes with the leukemia specific marker "CALLA". Representative examples of suitable tumors include melanomas, colorectal carcinomas, lung carcinomas (including large cell, small cell, squamous and adeno-carcinomas), renal cell carcinomas and breast adeno-carcinomas.

As noted above, a variety of anti-tumor agents may be utilized in accordance with the present invention. Within the context of the present invention, "anti-tumor agents" are understood to refer to compounds or molecules which inhibit the growth of a selected tumor as discussed above. Representative examples of anti-tumor agents include immune activators and tumor proliferation inhibitors. Briefly, immune activators function by improving immune recognition of tumor-specific antigens such that the immune system becomes "primed." Priming may consist of lymphocyte proliferation, differentiation, or evolution to higher affinity interactions. The immune system thus primed will more effectively inhibit or kill tumor cells. Immune activation may be subcategorized into immune modulators (molecules which affect the interaction between lymphocyte and tumor cell) and lymphokines, that act to proliferate, activate, or differentiate immune effector cells. Representative examples of immune modulators include CD3, ICAM-1, ICAM-2, LFA-1, LFA-3, β-2-microglobulin, chaperones, alpha interferon and gamma interferon, B7/BB1 and major histocompatibility complex (MHC). Representative examples of lymphokines include gamma interferon, tumor necrosis factor, IL-1, IL-2, IL-3, IL4, IL-5, IL-6, IL-7, IL-8, IL-9, IL-10, IL-11, GM-CSF, CSF-1, and G-CSF.

Tumor proliferation inhibitors act by directly inhibiting cell growth, or by directly killing the tumor cell. Representative examples of tumor proliferation inhibitors include toxins such as ricin (Lamb et al., *Eur. J. Biochem.* 148:265–270, 1985), abrin (Wood et al., *Eur. J. Biochem.* 198:723–732, 1991; Evensen, et al., *J. of Biol. Chem.* 266:6848–6852, 1991: Collins et al., *J. of Biol. Chem.* 265:8665–8669, 1990; Chen et al, *Fed. of Eur. Biochem Soc.* 309:115–118, 1992), diphtheria toxin (Tweten et al., *J. Biol. Chem.* 260:10392–10394, 1985), cholera toxin (Mekalanos et al., *Nature* 306:551–557, 1983; Sanchez & Holmgren, *PNAS* 86:481–485, 1989), gelonin (Stirpe et al., *J. Biol. Chem.* 255:6947–6953, 1980), pokeweed (Irvin, *Pharmac. Ther.* 21:371–387, 1983), antiviral protein (Barbieri et al., *Biochem. J.* 203:55–59, 1982; Irvin et al., *Arch. Biochem. &*

Biophys. 200:418–425, 1980; Irvin, Arch. Biochem & Biophys. 169:522–528, 1975), tritin, Shigella toxin (Calderwood et al., PNAS 84:4364–4368, 1987; Jackson et al., Microb. Path. 2:147–153, 1987), and Pseudomonas exotoxin A (Carroll and Collier, J. Biol. Chem. 262:8707–8711, 1987), herpes simplex virus thymidine kinase (HSVTK) (Field et al., J. gen. Virol. 49:115–124, 1980), and E. coli. guanine phosphoribosyl transferase. Additional examples of tumor proliferation inhibitors include antisense sequences which inhibit tumor cell growth by preventing the cellular synthesis of critical proteins needed for cell growth. Examples of such antisense sequences include antisense thymidine kinase, antisense dihydrofolate reductase (Maher and Dolnick, Arch. Biochem. & Biophys. 253:214–220, 1987; Bzik et al., PNAS 84:8360–8364, 1987), antisense HER2 (Coussens et al., Science 230:1132–1139, 1985), antisense ABL (Fainstein, et al., Oncogene 4:1477–1481, 1989), antisense Myc (Stanton et al., Nature 310:423–425, 1984) and antisense ras, as well as antisense sequences which block any of the enzymes in the nucleotide biosynthetic pathway. Finally, tumor proliferation inhibitors also include tumor suppressors such as p53, retinoblastoma (Rb), and MCC and APC for colorectal carcinoma.

In addition, within a further embodiment of the invention antisense RNA may be utilized as an anti-tumor agent in order to induce a potent Class I restricted response. Briefly, in addition to binding RNA and thereby preventing translation of a specific mRNA, high levels of specific antisense sequences are believed to induce the increased expression of interferons (including gamma-interferon), due to the formation of large quantities of double-stranded RNA. The increased expression of gamma interferon, in turn, boosts the expression of MHC Class I antigens. Preferred antisense sequences for use in this regard include actin RNA, myosin RNA, and histone RNA. Antisense RNA which forms a mismatch with actin RNA is particularly preferred.

Sequences which encode the above-described anti-tumor agents may be obtained from a variety-of sources. For example, plasmids that contain sequences which encode anti-tumor agents may be obtained from a depository such as the American Type Culture Collection (ATCC, Rockville, Md.), or from commercial sources such as British Bio-Technology Limited (Cowley, Oxford England). Representative sources sequences which encode the above-noted anti-tumor agents include BBG 12 (containing the GM-CSF gene coding for the mature protein of 127 amino acids), BBG 6 (which contains sequences encoding gamma interferon), ATCC No. 39656 (which contains sequences encoding TNF), ATCC No. 20663 (which contains sequences encoding alpha interferon), ATCC Nos. 31902, 31902 and 39517 (which contains sequences encoding beta interferon), ATCC No 67024 (which contains a sequence which encodes Interleukin-1β), ATCC Nos. 39405, 39452, 39516, 39626 and 39673 (which contains sequences encoding Interleukin-2), ATCC Nos. 59399, 59398, and 67326 (which contain sequences encoding Interleukin-3), ATCC No. 57592 (which contains sequences encoding Interleukin-4), ATCC Nos. 59394 and 59395 (which contain sequences encoding Interleukin-5), and ATCC No. 67153 (which contains sequences encoding Interleukin-6).

Alternatively, known cDNA sequences which encode anti-tumor agents may be obtained from cells which express or contain the sequences. Briefly, within one embodiment mRNA from a cell which expresses the gene of interest is reverse transcribed with reverse transcriptase using oligo dT or random primers. The single stranded cDNA may then be amplified by PCR (see U.S. Pat. Nos. 4,683,202, 4,683,195 and 4,800,159. See also PCR Technology: Principles and Applications for DNA Amplification, Erlich (ed.), Stockton Press, 1989) utilizing oligonucleotide primers complementary to sequences on either side of desired sequences. In particular, a double stranded DNA is denatured by heating in the presence of heat stable Taq polymerase, sequence specific DNA primers, ATP, CTP, GTP and TTP. Double-stranded DNA is produced when synthesis is complete. This cycle may be repeated many times, resulting in a factorial amplification of the desired DNA.

Sequences which encode the above-described anti-tumor agents may also be synthesized, for example, on an Applied Biosystems Inc. DNA synthesizer (e.g., ABI DNA synthesizer model 392 (Foster City, Calif.)).

In addition to the anti-tumor agents described above, the present invention also provides anti-tumor agents which comprise a fusion protein of, for example, two or more cytokines, immune modulators, toxins or differentiation factors. Preferred anti-tumor agents in this regard include alpha interferon—Interleukin-2, GM-CSF-IL-4, GM-CSF-IL-2, GM-CSF-IL-3 (see U.S. Pat. Nos. 5,082,927 and 5,108,910), GM-CSF—gamma interferon, and gamma interferon—IL-4. Within a particularly preferred embodiment, the anti-tumor agent is a gamma interferon-Interleukin-2 fusion protein. The construction of these anti-tumor agent(s) may be readily accomplished given the disclosure provided herein. The construction of a particularly preferred anti-tumor agent, gamma interferon—Interleukin-2, is described in more detail below in Example 1F.

Within other embodiments of the invention, the anti-tumor agent may further comprise a membrane anchor, and may be constructed, for example, as an anti-tumor agent—membrane anchor fusion protein. Briefly, the membrane anchor aspect of the fusion protein may be selected from a variety of sequences, including, for example, the transmembrane domain of well known molecules. Generally, membrane anchor sequences are regions of a protein that bind the protein to a membrane. Customarily, there are two types of anchor Sequences that attach a protein to the outer surface of a cell membrane: (1) transmembrane regions that span the lipid bilayer of the cell membrane, and interact with the hydrophobic center region (proteins containing such regions are referred to integral membrane proteins), and (2) domains which interact with an integral membrane protein or with the polar surface of the membrane (such proteins are referred to as peripheral, or extrinsic, proteins).

Membrane anchors for use within the present invention may contain transmembrane domains which span the membrane one or more times. For example, in glycophorin and guanylyl cyclase, the membrane binding region spans the membrane once, whereas the transmembrane domain of rhodopsin spans the membrane seven times, and that of the photosynthetic reaction center of Rhodopseudomonas viridis spans the membrane eleven times (see Ross et al., J. Biol. Chem. 257:4152, 1982; Garbers, Pharmac. Ther. 50:337–345, 1991; Engelman et al., Proc. Natl. Acad. Sci. USA 77:2023, 1980; Heijne and Manoil, Prot. Eng. 4:109–112, 1990). Regardless of the number of times the protein crosses the membrane, the membrane spanning regions typically have a similar structure. More specifically, the 20 to 25 amino-acid residue portion of the domain that is located inside the membrane generally consists almost entirely of hydrophobic residues (see Eisenberg et al., Ann. Rev. Biochem. 53:595–623, 1984). For example, 28 of the 34 residues in the membrane spanning region of glycophorin are hydrophobic (see Ross et al.; Tomita et al., *Biochemistry* 17:4756–4770, 1978). In addition, although structures such as beta sheets and barrels do occur, the membrane spanning regions typically have an alpha helical structure, as determined by X-ray diffraction, crystallography and cross-linking studies (see Eisenberg et al. at 20; Heijne and Manoil at 109). The location of these transmembrane helices within a given sequence can often be predicted based on hydrophobicity plots. Stryer et al., *Biochemistry*, 3rd. ed. 304, 1988. Particularly preferred membrane anchors for use within the present invention include naturally occurring cellular proteins (that are non-immunogenic) which have been demonstrated to function as membrane signal anchors (such as glycophorin).

Within a preferred aspect of the present invention, a DNA sequence is provided which encodes a membrane anchor—gamma interferon fusion protein. Within one embodiment, this fusion protein may be constructed by genetically fusing the sequence which encodes the membrane anchor of the gamma-chain of the Fc receptor, to a sequence which encodes gamma-interferon. The construction of such an anti-tumor agent is set forth in more detail below in Example 1.

Once a sequence encoding at least one anti-tumor agent has been obtained, it is necessary to ensure that the sequence encodes a non-tumorigenic protein. Various assays are known and may easily be accomplished which assess the tumorigenicity of a particular cellular component. Representative assays include tumor formation in nude mice or rats, colony formation in soft agar, and preparation of transgenic animals, such as transgenic mice.

Tumor formation in nude mice or rats is a particularly important and sensitive method for determining the tumorigenicity of an anti-tumor agent. Nude mice lack a functional cellular immune system (i.e., do not possess CTLs), and therefore provide a useful in vivo model in which to test the tumorigenic potential of cells. Normal non-tumorigenic cells do not display uncontrolled growth properties if injected into nude mice. However, transformed cells will rapidly proliferate and generate tumors in nude mice. Briefly, in one embodiment the vector construct is delivered to syngeneic murine cells, followed by injection into nude mice. The mice are visually examined for a period of 2 to 8 weeks after injection in order to determine tumor growth. The mice may also be sacrificed and autopsied in order to determine whether tumors are present. (Giovanella et al., *J. Natl. Cancer Inst.* 48:1531–1533, 1972; Furesz et al., "Tumorigenicity testing of cell lines considered for production of biological drugs," *Abnormal Cells, New Products and Risk*, Hopps and Petricciani (eds.), Tissue Culture Association, 1985; and Levenbook et al., *J. Biol. Std.* 13:135–141, 1985).

Tumorigenicity may also be assessed by visualizing colony formation in soft agar (MacPherson and Montagnier, *Vir.* 23:291–294, 1964). Briefly, one property of normal non-tumorigenic cells is "contact inhibition" (i.e., cells will stop proliferating when they touch neighboring cells). If cells are plated in a semi-solid agar support medium, normal cells rapidly become contact inhibited and stop proliferating, whereas tumorigenic cells will continue to proliferate and form colonies in soft agar.

Transgenic animals, such as transgenic mice, may also be utilized to assess the tumorigenicity of an anti-tumor agent (e.g., Stewart et al., *Cell* 38:627–637, 1984; Quaife et al., *Cell* 48:1023–1034, 1987; and Koike et al., *Proc. Natl. Acad. Sci. USA* 86:5615–5619, 1989). In transgenic animals, the gene of interest may be expressed in all tissues of the animal. This unregulated expression of the transgene may serve as a model for the tumorigenic potential of the newly introduced gene.

In addition to tumorgenicity studies, it is generally preferable to determine the toxicity of the anti-tumor agent(s), prior to administration. A variety of methods well known to those of skill in the an may be utilized to measure such toxicity, including for example, clinical chemistry assays which measure the systemic levels of various proteins and enzymes, as well as blood cell volume and number.

Once an anti-tumor agent has been selected, it is placed into a vector construct which directs its expression. Within the context of the present invention, a "vector construct" is understood to refer to an assembly which is capable of directing the expression of the sequence(s) or gene(s) of interest. The vector construct must include transcriptional promoter element(s), and preferably includes a signal which directs polyadenylation. In addition, the vector construct must include a sequence which, when transcribed, is operably linked to the sequence(s) or gene(s) of interest and acts as a translation initiation sequence. Optionally, the vector construct may also include a selectable marker such as Neo, TK, hygromycin, phleomycin, histidinol, or DHFR, as well as one or more restriction sites and a translation termination sequence. In addition, if the vector construct is placed into a retrovirus, the vector construct must include a packaging signal, long terminal repeats (LTRs), and positive and negative strand primer binding sites appropriate to the retrovirus used (if these are not already present).

As noted above, within one aspect of the present invention recombinant retroviruses are provided which carry a vector construct capable of directing the expression of an anti-tumor agent. The construction of such recombinant retroviral vectors is described in greater detail in an application entitled "Recombinant Retroviruses" (U.S. Ser. No. 07/586,603, filed Sep. 21, 1990, which is hereby incorporated by reference in its entirety). These recombinant retroviral vectors may be used to generate transduction competent retroviral vector particles by introducing them into appropriate packaging cell lines (see U.S. Ser. No. 07/800,921). In addition, Examples 1, 3 and 4 describe the preparation of recombinant retroviral vectors, as well as vector constructs which direct the expression of several anti-tumor agents.

Vector constructs of the present invention may also be developed and utilized with other viral carriers including, for example, poliovirus (Evans et al., *Nature* 339:385–388, 1989, and Sabin, *J. of Biol. Standardization* 1:115–118, 1973); rhinovirus; pox viruses, such as canary pox virus or vaccinia virus (Fisher-Hoch et al., *PNAS* 86:317–321, 1989; Flexner et al., *Ann. N.Y. Acad. Sci.* 569:86–103, 1989; Flexner et al., *Vaccine* 8:17–21, 1990; U.S. Pat. Nos. 4,603, 112 and 4,769,330; WO 89/01973); SV40 (Mulligan et al., *Nature* 277:108–114, 1979); influenza virus (Luytjes et al., *Cell* 59:1107–1113, 1989; McMicheal et al., *The New England Journal of Medicine* 309:13–17, 1983; and Yap et al, *Nature* 273:238–239, 1978); adenovirus (Berkner, *Biotechniques* 6:616–627, 1988, and Rosenfeld et al, *Science* 252:431–434, 1991); parvovirus such as adeno-associated virus (Samulski et al., *Journal of Virology* 63:3822–3828, 1989, and Mendelson et al., *Virology* 166:154–165, 1988); herpes (Kit, *Adv. Exp. Med. Biol.* 215:219–236, 1989); SV40; HIV; measles (EP 0 440,219); and Sindbis virus (Xiong et al., *Science* 234:1188–1191, 1989), and corona virus. In addition, viral carriers may be homologous, non-pathogenic (defective), replication competent virus (e.g., Overbaugh et al., *Science* 239:906–910, 1988), and nevertheless induce cellular immune responses, including CTL.

As noted above, a vector construct which directs the expression of at least one anti-tumor agent is directly administered to the tumor. Various methods may be utilized within the context of the present invention in order to directly administer the vector construct to the tumor. For example, within one embodiment a small metastatic lesion may be located, and the vector injected several times in several different locations within the body of tumor. Alternatively, arteries which serve a tumor may be identified, and the vector injected into such an artery, in order to deliver the vector directly into the tumor. Within another embodiment, a tumor which has a necrotic center may be aspirated, and the vector injected directly into the now empty center of the tumor. Within yet another embodiment, the vector construct may be directly administered to the surface of the tumor, for example, by application of a topical pharmaceutical composition containing the vector construct, or preferably, a recombinant retroviral vector carrying the vector construct.

Within another aspect of the present invention, methods are provided for inhibiting the growth of a selected tumor, comprising the step of delivering to a warm-blooded animal a vector construct which directs the expression of at least one anti-tumor agent, such that the growth of the tumor is inhibited. Within preferred embodiments, the vector construct is carried by a recombinant viral or retroviral vector.

In addition to vector constructs, nucleic acids which encode anti-tumor agent(s) may also be administered to a patient by a variety of methods. Representative examples include transfection by various physical methods, such as lipofection (Felgner et al, *Proc. Natl. Acad. Sci. USA* 84:7413–7417, 1989), direct DNA injection (Acsadi et al., *Nature* 352:815–818, 1991); microprojectile bombardment (Williams et al., *PNAS* 88:2726–2730, 1991); liposomes (Wang et al., *PNAS* 84:7851–7855, 1987); $CaPO_4$ (Dubensky et al., *PNAS* 81:7529–7533, 1984); DNA ligand (Wu et al, *J. of Biol. Chem.* 264:16985–16987, 1989); or administration of DNA linked to killed adenovirus (Curiel et al., *Hum. Gene Ther.* 3: 147–154, 1992). A variety of methods for administering recombinant retroviral vectors may also be utilized within the context of the present invention, such methods are described in greater detail in an application entitled "Recombinant Retroviruses" (U.S. Ser. No. 07/586,603), which is herein expressly incorporated by reference.

In addition, a cellular response (including CTL) may also be generated by administration of a bacteria which expresses an anti-tumor agent such as those discussed above, on its cell surface. Representative examples include BCG (Stover, *Nature* 351:456–458, 1991) and Salmonella (Newton et al., *Science* 244:70–72, 1989).

Within another aspect of the present invention, a method is provided for inhibiting the growth of a selected tumor in a warm blooded animal, comprising the steps of (a) removing tumor cells associated with the selected tumor from a warm-blooded animal, (b) infecting the removed cells with a vector construct which directs the expression of at least one anti-tumor agent, and (c) delivering the infected cells to a warm-blooded animal, such that the growth of the selected tumor is inhibited by immune responses generated against the gene-modified tumor cell. Within one embodiment of the present invention, subsequent to removing tumor cells from a warm-blooded animal, a single cell suspension may be generated by, for example, physical disruption or proteolytic digestion. In addition, division of the cells may be increased by addition of various factors such as melanocyte stimulating factor for melanomas or epidermal growth factor for breast carcinomas, in order to enhance uptake, genomic integration and expression of the recombinant viral vector.

Within the context of the present invention, it should be understood that the removed cells may not only be returned to the same animal, but may also be utilized to inhibit the growth of selected tumor cells in another, allogeneic, animal. In such a case it is generally preferable to have histocompatibility matched animals (although not always, see, e.g., Yamamoto et al., "Efficacy of Experimental FIV Vaccines," 1st International Conference of FIV Researchers, University of California at Davis, September 1991). Therefore, within yet another aspect of the present invention, a method for inhibiting the growth of a selected tumor in a warm-blooded animal is provided, comprising the steps of (a) removing tumor cells associated with the selected tumor from a warm-blooded animal, (b) contacting the cells with a vector construct which directs the expression of an anti-tumor agent such that the cells are capable of expressing said anti-minor agent, and (c) delivering the cells from step (b) to an allogeneic warm-blooded animal, such that the growth of the selected tumor is inhibited.

In addition, it should be understood that a variety of cells (target cells) may be utilized within the context of the present invention, including for example, human, macaque, dog, rat, and mouse cells.

Cells may be removed from a variety of locations including, for example, from a selected tumor. In addition, within other embodiments of the invention, a vector construct may be inserted into non-tumorigenic cells, including for example, cells from the skin (dermal fibroblasts), or from the blood (e.g., peripheral blood leukocytes). If desired, particular fractions of cells such as a T cell subset or stem cells may also be specifically removed from the blood (see, for example, PCT WO 91/16116, an application entitled "Immunoselection Device and Method"). Vector constructs may then be contacted with the removed cells utilizing any of the above-described techniques, followed by the return of the cells to the warm-blooded animal; preferably to or within the vicinity of a tumor.

The above-described methods may additionally comprise the steps of depleting fibroblasts or other non-contaminating tumor cells subsequent to removing tumor cells from a warm-blooded animal, and/or the step of inactivating the cells, for example, by irradiation.

As noted above, within preferred embodiments of the present invention, pharmaceutical compositions are provided comprising a recombinant retrovirus or virus carrying one of the above-described vector constructs, in combination with a pharmaceutically acceptable carrier or diluent. The composition may be prepared either as a liquid solution, or as a solid form (e.g., lyophilized) which is suspended in a solution prior to administration. In addition, the composition may be prepared with suitable carriers or diluents for either surface administration, injection, oral, or rectal administration.

Pharmaceutically acceptable carriers or diluents are non-toxic to recipients at the dosages and concentrations employed. Representative examples of carriers or diluents for injectable solutions include water, isotonic saline solutions which are preferably buffered at a physiological pH (such as phosphate-buffered saline or Tris-buffered saline); mannitol, dextrose, glycerol, and ethanol, as well as polypeptides or proteins such as human serum albumin. A particularly preferred composition comprises a vector or recombinant virus in 10 mg/ml mannitol, 1 mg/ml HSA, 20 mM Tris, pH 7.2, and 150 mM NaCl. In this case, since the recombinant vector represents approximately 1 μg of material, it may be less than 1% of high molecular weight material, and less than 1/100,000 of the total material (including water). This composition is stable at −70° C. for at least six months.

Pharmaceutical compositions of the present invention may also additionally include factors which stimulate cell division, and hence, uptake and incorporation of a recombinant retroviral vector. Representative examples include Melanocyte Stimulating Hormone (MSH), for melanomas or epidermal growth factor for breast or other epithelial carcinomas. Pharmaceutical compositions of the present invention may be injected via a variety of routes (e.g., intravenously ("i.v."), or subcutaneously ("s.c."), intramuscularly ("i.m.") or preferably, directly into the tumor. The individual doses normally used are $10^7$ to $10^9$ c.f.u. (colony forming units of neomycin resistance titered on HT1080 cells). These are administered at one to four week intervals for three or four doses initially. Subsequent booster shots may be given as one or two doses after 6–12 months, and thereafter annually.

The following examples are offered by way of illustration and not by way of limitation.

EXAMPLES

Example 1

Preparation of Murine Retroviral Provector DNA

A. Preparation of the Retroviral Backbone KT-3

An EcoR I-EcoR I fragment containing a 5' long terminal repeat ("LTR") and gag sequences from a Moloney murine leukemia virus ("MoMLV") in an N2 vector (Armentano et. al., *J. Vir.* 61:1647–1650, 1987; Eglitis et. al., *Science* 230:1395–1398, 1985) contained in pUC31, is ligated into the plasmid SK⁺ (Stratagene, Calif.). (The plasmid pUC31 is derived from pUC19 (Stratagene, Calif.) in which additional restriction sites Xho I, Bgl II, BssH II and Nco I are inserted between the EcoR I and Sac I sites of the polylinker.) The resulting construct is designated N2R5. The N2R5 construct is mutated by in vitro site-directed mutagenesis to change the ATG start codon to ATT in order to prevent gag expression. This mutagenized fragment is 200 base pairs (bp) in length, and flanked by Pst I restriction sites. The Pst I-Pst I mutated fragment is purified from the SK⁺ plasmid and inserted into the Pst I site of N2 MoMLV 5' LTR in pUC31 in order to replace the non-mutated 200 bp fragment. This construct is designated pUC31/N2R5g$^M$.

The 1.0 kilobase (Kb) MoMLV Y LTR EcoR I-EcoR I fragment from N2 is cloned into plasmid SK⁺ resulting in a construct designated N2R3⁻. A 1.0 Kb Cla I-Hind III fragment is purified from this construct.

The Cla I-Cla I dominant selectable marker gene fragment from pAFVXM retroviral vector (Kriegler et. al., *Cell* 38:483, 1984; St. Louis et. al., *PNAS* 85:3150–3154, 1988), comprising a SV40 early promoter driving expression of the neomycin phosphotransferase gene, is cloned into plasmid SK⁺. A 1.3 Kb Cla I-BstB I neogene fragment is purified from this plasmid.

The expression vector is constructed by a three-part ligation in which the Xho I-Cla I fragment containing a gene of interest as described below, and the 1.0 Kb MoMLV 3' LTR Cla I-Hind III fragment are inserted into the Xho I-Hind III site of pUC31/N2R5g$^M$ plasmid. The 1.3 Kb Cla I-BstB I neogene fragment is then inserted into the Cla I site of this plasmid in the sense orientation.

B. Cloning of mγ-IFN Into KT-3

Figure 1B:
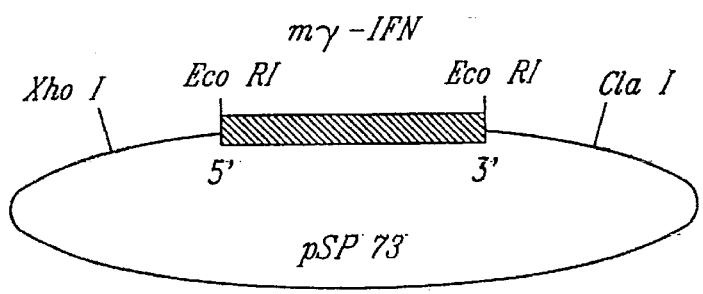
Figure 1C:
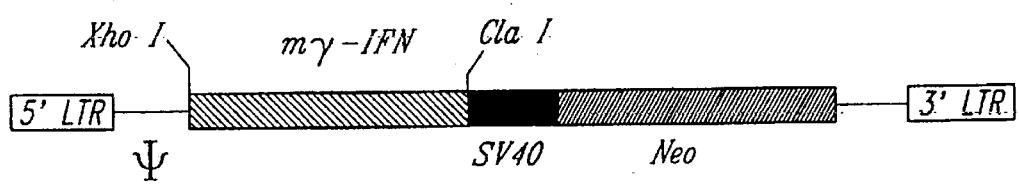

A mγ-IFN cDNA is cloned into the EcoR I site of pUC1813 essentially as set forth below. Briefly, pUC1813 (containing a sequence encoding γ-IFN) is prepared as essentially described by Kay et. al., *Nucleic Acids Research* 15:2778, 1987; and Gray et. al., *PNAS* 80:5842, 1983) (FIG. 1A). The mγ-IFN cDNA is retrieved by EcoR I digestion of pUC1813, and the isolated fragment is cloned into the EcoR I site of phosphatase-treated pSP73 (Promega; Madison, Wis.) (FIG. 1B). This construct is designated SP mγ-IFN. The orientation of the cDNA is verified by appropriate restriction enzyme digestion and DNA sequencing. In the sense orientation, the 5' end of the cDNA is adjacent to the Xho I site of the pSP73 polylinker and the 3' end adjacent to the Cla I site. The Xho I-Cla I fragment containing the mγ-IFN cDNA in either sense or antisense orientation is retrieved from SP mγ-IFN construct and cloned into the Xho I-Cla I site of the KT-3 retroviral backbone. This construct is designated KT mγ-IFN (FIG. 1).

C. Cloning of hγ-IFN Into KT-3

1. Preparation Of Sequences Encoding hγ-IFN Utilizing PCR (a) PHA Stimulation Of Jurkat Cells Jurkat cells (ATCC No. CRL 8163) are resuspended at a concentration of $1 \times 10^6$ cells/ml in RPMI growth media (Irvine Scientific; Santa Aria, Calif.) with 5% fetal bovine serum (FBS) to a final volume of 158.0 ml. Phytohemoagglutinin ("PHA") (Curtis Mathes Scientific, Houston, Tex.) is added to the suspension to a final concentration of 1%. The suspension is incubated at 37° C. in 5% $CO_2$ overnight. The cells are harvested on the following day and aliquoted into three. 50.0 ml centrifuge tubes. The three pellets are combined in 50 ml 1× phosphate buffered 'saline (PBS, 145 mM, pH 7.0.) and centrifuged at 1000 rpm for 5 minutes. The supernatant is decanted and the cells are washed with 50.0 ml PBS. The cells are collected for RNA isolation.

(b) RNA Isolation

The PHA stimulated Jurkat cells are resuspended in 22.0 ml guanidinium solution (4M guanidinium thiocyanate; 20 mM sodium acetate, pH 5.2; 0.1M dithiothreitol, 0.5% sarcosyl). This cell-guanidinium suspension is then passed through a 20 gauge needle six times in order to disrupt cell membranes. A CsCl solution (5.7M CsCl, 0.1M EDTA) is then overlaid with 11.0 ml of the disrupted cell-guanidinium solution. The solution is centrifuged for 24 hours at 28,000 rpm in a SW28.1 rotor (Beckman, Fullerton, Calif.) at 20° C. After centrifugation the supernatant is carefully aspirated and the tubes blotted dry. The pellet is resuspended in a guanidinium-HCl solution (7.4M guanidinium-HCl; 25 mM Tris-HCl, pH 7.5; 5 mM dithiothreitol) to a final volume of 500.0 μl. This solution is transferred to a microcentrifuge tube. Twelve and one-half microliters of concentrated Glacial acetic acid (HAc) and 250 μl of 100% EtOH are added to the microfuge tube. The solution is mixed and stored for several days at −20° C. to precipitate RNA.

After storage, the solution is centrifuged for 20 minutes at 14,000 rpm, 4° C. The pellet is then resuspended in 75% EtOH and centrifuged for 10 minutes in a microfuge at 14,000 rpm, 4° C. The pellet is dried by centrifugation under vacuum, and resuspended in 300 μl deionized (DI) $H_2O$. The concentration and purity of the RNA is determined by measuring optical densities at 260 and 280 nm.

(c) Reverse Transcription Reaction

Immediately before use, 5.0 μl (3.4 mg/ml) of purified Jurkat RNA is heat treated for 5 minutes at 90° C., and then placed on ice. A solution of 10.0 μl of 10× PCR buffer (500 mM KCl; 200 mM Tris HCl, pH 8.4; 25 mM $MgCl_2$; 1 mg/ml bovine serum albumin (BSA)); 10.0 μl of 10 mM dATP, 10.0 μl of 10 mM dGTP, 10.0 μl of 10 mM dCTP, 10.0 μl of 10 mM dTTP, 2.5 μl RNasin (40,000 U/ml, Promega; Madison, Wis.) and 33.0 μl DI $H_2O$, is added to the heat treated Jurkat cell RNA. To this solution 5.0 μl (108 nmol/ml) of V-OLI #56 (Sequence ID No. 1), and 5.0 μl (200,000 U/ml) MoMLV reverse transcriptase (Bethesda Research Laboratories, EC 3.1.27.5, Maryland) is mixed in a microfuge tube and incubated at room temperature for 10 minutes. Following the room temperature incubation, the reaction mixture is incubated for 1 hour at 37° C., and then incubated for 5 minutes at 95° C. The reverse transcription reaction mixture is then placed on ice in preparation for PCR.

(d) PCR Amplification

The PCR reaction mixture contains 100.0 μl reverse transcription reaction; 356.0 μl DI $H_2O$; 40.0 μl 10× PCR buffer; 1.0 μl (137 nmol/ml) V-OLI #5 (Sequence ID No. 2); 0.5 μl (320 nmol/ml) V-OLI #6 (Sequence ID No. 3), and 2.5 μl, 5,000 U/ml, Taq polymerase (EC 2.7.7.7, Perkin-Elmer Cetus, Calif.). One hundred microliters of this mixture is aliquoted into each of 5 tubes.

V-OLI #56 (Sequence ID No. 1)
5'-3': TAA TAA ATA GAT TTA GAT TTA

This primer is complementary to a sequence of the mγ-IFN cDNA 30 base pairs downstream of the stop codon.

V-OLI #5 (Sequence ID No. 2)
5'-3': GC CTC GAG ACG ATG AAA TAT ACA AGT TAT ATC TTG This primer is complementary to the 5' coding region of the mγ-IFN gene, beginning at the ATG start codon. The 5' end of the primer contains a Xho I restriction site.

V-OLI #6 (Sequence ID No. 3)
5'-3': GA ATC GAT CCA TTA CTG GGA TGC TCT TCG ACC TGG This primer is complementary to the 3' coding region of the mγ-IFN gene, ending at the TAA stop codon. The 5' end of the primer contains a Cla I restriction site.

Each tube was overlaid with 100.0 μl mineral oil, and placed into a PCR machine (Ericomp Twin Block System, Ericomp, Calif.). The PCR program regulates the temperature of the reaction vessel first at 95° C. for 1 minute, next at 67° C. for 2 minutes and finally at 72° C. for 2 minutes. This cycle is repeated 40 times. The last cycle regulates the temperature of the reaction vessel first at 95° C. for 1 minute, next at 67° C. for 2 minutes and finally at 72° C. for 7 minutes. The completed PCR amplification reactions are stored at 4° C. for 1 month in preparation for PCR DNA isolation.

(e) Isolation Of PCR DNA

The aqueous phase from the PCR amplification reactions are transferred into a single microfuge tube. Fifty microliters of 3M sodium acetate and 500.0 μl of chloroform:isoamyl alcohol (24:1) is added to the solution. The solution is vortexed and then centrifuged at 14,000 rpm at room temperature for 5 minutes. The upper aqueous phase is transferred to a fresh microfuge tube and 1.0 ml of 100% EtOH is added. This solution is incubated for 4.5 hours at −20° C. and then centrifuged at 14,000 rpm for 20 minutes. The supernatant is decanted, and the pellet is rinsed with 500.0 μl of 70% EtOH. The pellet is dried by centrifugation under a vacuum. The isolated hγ-IFN PCR DNA is resuspended in 10.0 μl DI $H_2O$.

2. Construction Of hγ-IFN Retroviral Vectors (a) Creation And Isolation. Of Blunt-Ended hγ-IFN PCR DNA Fragments The hγ-INF PCR DNA is blunt ended using T4 DNA polymerase. Specifically, 10.0 μl of PCR amplified DNA; 2.0 μl, 10×, T4 DNA polymerase buffer (0.33M Tris-acetate, pH 7.9, 0.66M potassium acetate, 0.10M magnesium acetate, 5 mM dithiothreitol, 1 mg/ml bovine serum albumin (BSA)); 1.0 μl, 2.5 mM dNTP (a mixture containing equal molar concentrations of dATP, dGTP, dTTP and dCTP); 7.0 μl DI H2O; 1.0 μl, 5000 U/ml, Klenow fragment (EC 2.7.7.7, New England Biolabs, Mass.); and 1.0 μl, 3000 U/ml, T4 DNA polymerase (EC 2.7.7.7, New England Biolabs, Mass.) are mixed together and incubated at 37° C. for 15 minutes. The reaction mixture is then incubated at room temperature for 40 minutes and followed by an incubation at 68° C. for 15 minutes.

The blunt ended hγ-INF is isolated by agarose gel electrophoresis. Specifically, 2.0 μl of loading dye (0.25% bromophenol blue; 0.25% xylene cyanol; and 50% glycerol) is added to reaction mixture and 4.0 μl is loaded into each of 5 lanes of a 1% agarose/Tris-borate-EDTA (TBE) gel containing ethidium bromide. Electrophoresis of the gel is performed for 1 hour at 100 volts. The desired DNA band containing hγ-INF, approximately 500 base pairs in length, is visualized under ultraviolet light.

This band is removed from the gel by electrophoretic transfer onto NA 45 paper (Schleicher and Schuell, Keene, New Hampshire). The paper is incubated at 68° C. for 40 minutes in 400.0 μl of high salt NET buffer (1M NaCl; 0.1 mM EDTA; and 20 mM Tris, pH 8.0) to elute the DNA. The NA 45 paper is removed from solution and 400.0 μl of phenol:chloroform:isoamyl alcohol (25:24:1) is added. The solution is vortexed and centrifuged at 14,000 for 5 minutes. The upper aqueous phase is transferred to a fresh tube and 400.0 μl of chloroform:isoamyl alcohol (24:1) is added. The mixture is vortexed and centrifuged for 5 minutes. The upper aqueous phase is transferred, a second time, to a fresh tube and 700.0 μl of 100% EtOH is added. The tube is incubated at −20° C. for 3 days. Following incubation, the DNA is precipitated from the tube by centrifugation for 20 minutes at 14,000 rpm. The supernatant is decanted and the pellet is rinsed with 500.0 μl of 70% EtOH. The pellet, containing blunt ended hγ-INF DNA, is dried by centrifugation under vacuum and resuspended in 50.0 μl of DI $H_2O$.

The isolated blunt ended hγ-IFN DNA is phosphorylated using polynucleotide kinase. Specifically, 25.0 μl of blunt-ended hγ-INF DNA, 3.0 μl of 10× kinase buffer (0.5M Tris-HCl, pH 7.6; 0.1M $MgCl_2$; 50 mM dithiothreitol; 1 mM spermidine; 1 mM EDTA), 3.0 μl of 10 mM ATP, and 1.0 μl of T4 polynucleotide kinase (10,000 U/ml, EC 2.7.1.78, New England Biolabs, Maryland) is mixed and incubated at 37° C. for 1 hour 45 minutes. The enzyme is then heat inactivated by incubating at 68° C. for 30 minutes.

(b) Ligation Of hγ-IFN PCR DNA Into The SK+ Vector

An SK+ plasmid is digested with Hinc II restriction endonuclease and purified by agarose gel electrophoresis as described below. Specifically, 5.9 μl (1.7 mg/ml) SK+ plasmid DNA (Stratagene; San Diego, Calif.); 4.0 μl 10× Universal buffer (Stratagene, Calif.); 30.1 μl DI $H_2O$, and 4.0 μl Hinc II, 10,000 U/ml, are mixed in a tube and incubated for 7 hours at 37° C. Following incubation, 4.0 μl of loading dye is added to the reaction mixture and 4.0 μl of this solution is added to each of 5 lanes of a 1% agarose/TBE gel containing ethidium bromide. Electrophoresis of the gel is performed for 2 hours at 105 volts. The Hinc II cut SK+ plasmid, 2958 base pairs in length, is visualized with ultraviolet light. The digested SK+ plasmid is isolated from the gel using the method described in Example 1C, Section 2(a).

Dephosphorylation of the Hinc II cleavage site of the plasmid is performed using calf intestine alkaline phosphatase. Specifically, 50.0 μl digested SK+ plasmid; 5.0 μl 1M Tris, pH 8.0; 2.0 μl 5 mM EDTA, pH 8.0; 43.0 μl H$_2$O and 2.0 μl, 1,000 U/ml, calf intestinal phosphatase ("CIP") (Boehringer Mannheim, Indianapolis, Ind.) are mixed in a tube and incubated at 37° C. for 15 minutes. Following incubation, 2.0 μl CIP is added and the solution is incubated at 55° C. for 90 minutes. Following this incubation, 2.5 μl 20% sodium dodecyl sulfate ("SDS"), 1.0 μl 0.5M EDTA, pH 8.0, and 0.5 μl, 20 mg/ml, proteinase K (EC 3.4.21.14, Boehringer Mannheim, Indianapolis, Ind.) are added, and the solution is incubated at 55° C. for 2 hours. This solution is cooled to room temperature, and 110.0 μl phenol:chloroform:isoamyl alcohol (25:24:1) is added. The mixture is vortexed and centrifuged at 14,000 rpm for 5 minutes. The upper aqueous phase is transferred to a fresh tube and 200.0 μl of 100% EtOH is added. This mixture is incubated at 70° C. for 15 minutes. The tube is centrifuged and the pellet is rinsed with 500.0 μl of 70% EtOH. The pellet was then dried by centrifugation under a vacuum. The dephosphorylated SK$^+$ plasmid is resuspended in 40 μl DI H$_2$O.

The hγ-INF PCR DNA is ligated into the SK$^+$ plasmid using T4 DNA ligase. Specifically, 30.0 μl blunt ended, phosphorylated, hγ-IFN PCR DNA reaction mixture, 2.0 μl dephosphorylated SK$^+$ plasmid and 1.0 μl T4 DNA ligase are combined in a tube and incubated overnight at 16° C. DNA was isolated using a minprep procedure. More specifically, the bacterial strain DH5α (Gibco BRL, Gaithersburg, Md.) is transformed with 15.0 μl of ligation reaction mixture, plated on Luria-Bertani agar plates (LB plates) containing ampicillin and 5-bromo-4-chloro-3-indolyl-β-D-galactoside (X-gal, Gold Biotechnology; St. Louis, Mo.), and incubated overnight at 37° C. DNA is isolated from white bacterial colonies using the procedure described by Sambrook et al. (*Molecular Cloning*, Cold Springs Harbor Press, 1989). The presence of the hγ-IFN gene is determined by restriction endonuclease cleavage with Xho I, Cla I, Ava II, Dra I, and Ssp I. The expected endonuclease restriction cleavage fragment sizes for plasmids containing the hγ-IFN gene are presented in Table 1. The isolated DNA plasmid is designated SK hγ-IFN and used in constructing the retroviral vectors.

TABLE 1

| Enzyme | Fragment Size (bp) |
| --- | --- |
| Xho I and Cla I | 500, 2958 |
| Ava II | 222, 1307, 1937 |
| Dra I | 700, 1149, 1500 |
| Ssp I | 750, 1296, 2600 |

(c) Ligation Of hγ-IFN Gene Into Retroviral Vector

The interferon gene is removed from SK hγ-IFN vector by digestion with Xho I and Cla I restriction endonucleases. The resulting fragment containing the hγ-IFN gene is approximately 500 bp in length, and is isolated in a 1% agarose/TBE gel electrophoresis as described in Example 1C, 2(b). The Xho I-Cla I hγ-IFN fragment is then ligated into the KT-3 retroviral backbone. This construct is designated KT hγ-IFN. The structure and presence expression of hγ-IFN is determined by transforming DH5a bacterial strain with the KT hγ-IFN construct. Specifically, the bacteria is transformed with 15.0 μl of ligation reaction mixture. The transformed bacterial cells are plated on LB plates containing ampicillin. The plates are incubated overnight at 37° C. and bacterial colonies are selected. The DNA is isolated as described in (b) above, and digested with Xho I, Cla I, Dra I, Nde I, and Ssp I. The expected endonuclease restriction cleavage fragment sizes for plasmids containing the hγ-IFN gene are presented in Table 2.

TABLE 2

| Enzyme | Fragment Size (bp) |
| --- | --- |
| Xho I and Cla I | 500, 6500 |
| Nde I | 1900, 5100 |
| Dra I | 692, 2700, 3600 |
| Ssp 1 | 541, 1700, 4700 |

D. Cloning of hIL-2 Into KT-3

The method for cloning hIL-2 into KT-3 retroviral vector is essentially identical to the procedure for cloning hγ-IFN into KT-3, with the exception that different primers are required for amplification of the hIL-2 DNA sequence. The following hIL-2 PCR primer sequences are used:

V-OLI #55 (Sequence ID No. 4)

5'-3': ATA AAT AGA AGG CCT GAT ATG

This primer is complimentary to a sequence of the hIL-2 cDNA downstream of the stop codon.

V-OLI #1 (Sequence ID No. 5)

5'-3': GC CTC GAG ACA ATG TAC AGG ATG CAA CTC CTG TCT

This primer is the sense sequence of the hIL-2 gene complimentary to the 5' coding region beginning at the ATG start codon. The 5' end of the primer contains a Xho I restriction site.

V-OLI #2 (Sequence ID No. 6)

5'-3': GA ATC GAT TTA TCA AGT CAG TGT TGA GAT GAT GCT

The primer is the anti-sense sequence of the hIL-2 gene complimentary to the 3' coding region ending at the TAA stop codon. The 5' end of the primer contains the Cla I restriction site.

E. Cloning Of Membrane-Bound human γ-IFN Into KT-3

1. Methods For Constructing Membrane-Bound Human γ-IFN (a) Sequence Selection For Membrane-Bound hγ-IFN The cell surface membrane-bound hγ-IFN protein is a chimeric protein comprising the complete cDNA of hγ-IFN, the transmembrane region of human Fc receptor γ-chain and a modified cytoplasmic region of Fc receptor γ-chain. The modification of the cytoplasmic region consists of an internal deletion and is intended to block any signal transduction associated with an Fc receptor.

Modification and splicing of DNA is achieved by the overlap extension PCR method of Horton et al. (*Gene* 77:61–68, 1978). The carboxyl terminus of hγ-IFN is joined to the Fc receptor γ-chain at the amino end of the transmembrane region. The underlined amino acids identify the transmembrane region sequence.

| Human γ-IFN (Sequence ID No. 7) | ...G R R A S Q COOH |
| --- | --- |
| Human Fc receptor γ-chain (Sequence ID No. 8) | NH$_2$ ...L G E P Q <u>L C Y I L D A</u> COOH |

| | | |
|---|---|---|
| Hybrid (Sequence ID No. 9) | NH$_2$ | ...G R R A S Q <u>L C Y I L D A</u> COOH |

The addition, of several hydrophilic amino acids between hγ-IFN and the transmembrane region may be employed to extend the active region away from the cell surface (Kuster, et. al., *J. Bio. Chem.* 265:6448, 1990). The sequence modification of the transmembrane region of the human Fc receptor γ-chain involves the deletion of amino acids $S^{57}$-$Y^{76}$. The underlined amino adds identify the deleted sequence.

Human Fc receptor γ-chain intracellular region
(Sequence ID Nos. 10 and 36)
...K A A I T $S^{57}$ <u>Y E K ... Q E T Y$^{76}$</u> E T L K ... COOH
Modified intracellular region
(Sequence ID No. 11)
...K A A I T E T L K ...$_{COOH}$ (b) PCR Amplification A polymerase chain reaction (PCR) mixture is prepared according to procedures specified by Perkin-Elmer-Cetus, Calif. More specifically, the reaction mixture contains 0.5 µg purified plasmid, 5.0 µl of 10× PCR reaction buffer, 5.0 µl 2.5 mM of each dATP, dCTP, dGTP, and dTTP, 1;0 µl; 0.5 µg of each primer, 0.5 µl of 2.5 units/100.0 µl Taq polymerase and 8.0 µl of 10 mM MgCl$_2$. The reaction mixture is then brought to 50.0 µl with DI H$_2$O.

Each reaction mixture is overlaid with 100.0 µl mineral oil, and placed into a PCR machine (Ericomp Twin Block System). The PCR program regulates the temperature of the reaction vessel first at 95° C. for 1 minute, next at 67° C. for 2 minutes and finally at 72° C. for 2 minutes. This cycle is repeated 40 times. The last cycle regulates the temperature of the reaction vessel first at 95° C. for 1 minute, next at 67° C. for 2 minutes and finally at 72° C. for 7 minutes. The completed PCR reactions are stored at 4° C. for about 1 month.

(c) Construction Of Hybrid γ-IFN/Fc Receptor Retroviral Vector

The following hγ-IFN PCR primer sequences are used:
(Sequence ID No. 12)
5'-3': CAG GAC CCA TAT GTA AAA GAA GCA GAA AAC C
This primer is the sense sequence of hγ-IFN corresponding to a region at the carboxy terminus of the protein, and is designated hγ-IFN/P1.

(Sequence ID No. 13)

5'-3': GCA GAG CTG GGA TGC TCT TCG ACC TCG

This primer is the anti-sense sequence of hγ-IFN corresponding to a region at the carboxy terminus of the protein, and is designated hγ-IFN/P2.

The following γ-chain Fc receptor primer sequences are used:

(Sequence ID No. 14)

5'-3': GCA TCC CAG CTC TGC TAT ATC CTG GAT GCC

This primer is the sense sequence of Fc receptor γ-chain, and is designated γ-chain Fc/P3.

(Sequence ID No. 15)

5'-3': GGC ATG CAG GCA TAT GTG ATG CCA ACC

This primer is the anti-sense sequence of Fc receptor γ-chain, and is designated chain Fc/P4.

The hγ-IFN template DNA from Example 1C. 1(e), hγ-IFN/P1 primer DNA, hγ-IFN/P2 primer DNA, 7-chain Fc receptor template DNA, γ-chain Fc/P3 primer DNA and γ-chain Fc/P4 primer DNA are combined, denatured at 95° C. for 1 minute, and extended in the presence of PCR reaction mix without additional primers. The 3' end of the template-primer hγ-IFN DNA will anneal to the 5' end of the template-primer γ-chain Fc DNA and extension will produce the hybrid product designated hγ-IFN/Fc-Rec. The primers hγ-IFN/P1 and γ-chain Fc/P4 are then added and 40 cycles of PCR are performed to amplify the hγ-IFN/Fc-Rec product.

The hγ-IFN/Fc. Rec product contains only a short fragment of the hγ-IFN gene. This fragment extends from the Nde I restriction endonuclease site within the gene to the end of the gene sequence. hγ-IFN/Fc-Rec is digested with Nde I and cloned into KT hγ-IFN containing the leader portion of hγ-IFN. This vector is designated KT hγ-IFN/Fc-Rec.

(d) Construction Of Hybrid hγ-IFN/Modified Fc Receptor Intracellular Region Retroviral Vector The γ-chain of the Fc receptor is modified to eliminate the biological activity of the protein. The following modified Fc receptor intracellular region PCR primer sequences are utilized:

(Sequence ID No. 16)

5'-3': CAG AGT CTC GGT TAT AGC TGC CTT TCG CAC

This primer is the sense sequence of the modified Fc receptor intracellular region, and is designated mFc/P5.

(Sequence ID No. 17)

5'-3': GCT ATA ACC GAG ACT CTG AAG CAT GAG

This primer is the anti-sense sequence of the modified Fc receptor intracellular region, and is designated mFc/P6.

The hγ-IFN/Fc-Rec template DNA from Example 1C 3(a), hγ-IFN/P1 primer DNA, mFc/P5 primer DNA, mFc/P6 primer DNA and γ-chain Fc/P4 primer DNA are combined, denatured at 95° C. for 1 minute and extended in the presence of PCR reaction mix without additional primers. The 3' end of the template-primer (hγ-IFN/Fc-Rec template DNA bound hγ-IFN primer DNA and mFc/P5 primer DNA) will anneal to the 5' end of the template-primer (hγ-IFN/Fc-Rec template DNA bound mFc/P6 primer DNA and γ-chain Fc/P4 primer DNA) and extension will produce a modified Fc receptor γ-chain omitting 20 amino acid codons. Primers mFc/P6 and γ-chain Fc/P4 are then added and 40 cycles of PCR are performed to amplify the modified product. The PCR product is designated mFcIR.

The KT hγ-IFN/Fc-Rec vector is digested with Nde I. The Nde I-Nde I fragment removed from this vector is replaced with the Nde I-Nde I mFcIR PCR DNA fragment. This vector is designated KT hγ-IFN/mFc-Rec.

F. Cloning of Human Gamma IFN/Human IL-2 Into KT-3

1. Method For Constructing hγ-IFN/hIL-2 Hybrid (a) Sequence Selection for hγ-IFN/hIL-2 Hybrid Two methods are described below for the construction of IFN/hIL-2 hybrid proteins. The first method describes the construction of a hybrid protein having γ-IFN at the carboxyl terminus and the second method describes a hybrid protein having human interleukin-2 (hIL-2) at the carboxyl terminus.

Modification and splicing of DNA is achieved by the overlap extension PCR method of Horton et al. (*Gene* 77:61–68, 1989). In the first method of construction the complete hγ-IFN coding sequence, including the hγ-IFN signal sequence, is linked to the complete hIL-2 coding sequence except for the hIL-2 signal sequence. DNA sequences are obtained from Genebank, Washington D.C., hγ-IFN (HUMIFNINI). The underlined sequence indicates the signal peptide sequence that was excluded.

Human γ-IFN$_{NH_2}$ ...G R R A S Q COOH
(Sequence ID No. 18)
Human IL-2   NH$_2$...L V T N S A P T S S S ...COOH
(Sequence ID No. 19)
Hybrid amino   NH$_2$...G R R A S Q A P T S S S ...COOH
acid sequence
(Sequence ID No. 20)

In the second method the complete hIL-2 coding sequence, including the hIL-2 signal sequence is linked to the complete hγ-IFN coding sequence excluding the hγ-IFN signal sequence. DNA sequences are obtained from Genebank; hIL-2 (HUMIL2S1, HUMIL2S2 and HUMIL2S3). The underlined sequence indicates the signal peptide sequence.

Human IL-2   NH$_2$...I I S T L T COOH
(Sequence ID No. 21)
Human γ-IFN$_{NH_2}$ ...V L G S L G C Y C Q D ...COOH
(Sequence ID No. 22)
Hybrid amino   NH$_2$...I I S T L T C Y C Q D ...COOH
acid sequence
(Sequence ID No. 23)

(b) Construction of Hybrid hγ-IFN/hIL-2 Retroviral Vector

The following hγ-IFN primer sequences are used:
(Sequence ID No. 24)
5'-3': CAG GAC CCA TAT GTA AAA GAA GCA GAA G
This primer is the sense sequence of the hγ-IFN corresponding to a region at the carboxy terminus of the hγ-IFN protein, and is designated hγ-IFN/P7.
(Sequence ID No. 25)
5'-3': GG TGC ACT CTG GGA TGC TCT TCG ACC TCG
This primer is the anti-sense sequence of the hγ-IFN corresponding to a region at the carboxy terminus of the hγ-IFN protein, and is designated hγ-IFN/P8.
The following hIL-2 primer sequences are used:
(Sequence ID No. 26)
5'-3': CC CAG GCA CCT ACT TCA AGT TCT ACA AAG
This primer is the sense sequence of the hIL-2 corresponding to a region at the amino terminus of the hIL-2 protein, and is designated hIL-2/P9.
(Sequence ID No. 27)
5'-3': GGG TCT TAA GTG AAA GTT TTT GCT TTG AGC
This primer is the anti-sense sequence of the hIL-2 corresponding to a region at the amino terminus of the hIL-2 protein, and is designated hIL-2/P10.

The hγ-IFN template DNA from Example 1C 1(e), hγ-IFN/P7 primer DNA, hγ-IFN/P8 primer DNA, hIL-2 template DNA from hIL-2/P9 primer DNA and hIL-2/P10 primer DNA are combined, denatured at 95° C. for 1 minute, and extended in the presence of PCR reaction mix without additional primers. The 3' end of the template-primer hγ-IFN DNA will anneal to the 5' end of the template-primer hIL-2 DNA and extension will produce a 673 bp fragment designated hγ-IFN/hIL-2. The primers hγ-IFN/P7 and hIL-2/P10 are then added and 40 cycles of PCR are performed to amplify the hγ-IFN/hIL-2 product.

The hybrid hγ-IFN/hIL-2 vector is constructed by a three part ligation. The 5' end of KT hγ-IFN retroviral vector is isolated from Nde I restriction endonuclease digestion. This hγ-IFN/hIL-2 product is digested with Nde 1 and Afl II to yield a 656 base pair fragment. This fragment is ligated to the Nde I site of the isolated 5' end of KT hγ-IFN. The 3' end of KT hIL2 retroviral vector is isolated from Afl II restriction endonuclease digestion. The Afl II restriction site of the 3' KT hIL-2 is ligated to the Afl II restriction site of the construct. This retroviral construct is designated KT hγ-IFN/hIL-2.

(c) Construction of Hybrid hIL-2/hγ-IFN Retroviral Vector

The following hIL-2 primer sequences are used:
(Sequence ID No. 28)
5'-3': CAT CTT CAG TGT CTA GAA GAA GAA CTC
This primer is the sense sequence of hIL-2 corresponding to a region at the carboxy terminus of the hIL-2 protein, and is designated hIL-2/P11.
(Sequence ID No. 29)
5'-3': G GCA GTA ACA AGT CAG TGT TGA GATV-GAT GC
This primer is the anti-sense sequence hIL-2 corresponding to a region of the carboxy terminus of the hIL-2 protein, and is designated hIL-2/P12.
The following hγ-IFN primer sequences are used:
(Sequence ID No. 30)
5'-3': GT GAC TGA TGT TAC TGC CAG GAC CCA TAT G
This primer is the sense sequence corresponding to a region of the amino terminus of the hγ-IFN protein, and is designated hγ-IFN/P13.
(Sequence ID No. 31)
5'-3': CGA ATA AFT AGT CAG CTT FTC GAA GTC
This primer is the anti-sense sequence corresponding to a region of the amino terminus of the hγ-IFN protein, and is designated hγ-IFN/P14.

The hIL-2 template DNA from hIL-2/P11 primer DNA, hIL-2/P12 primer DNA, hγ-IFN/P13 template DNA from Example 1C 1(e), hγ-IFN/P13 primer DNA and hγ-IFN/P14 primer DNA are combined, denatured at 95° C. for 1 minute and extended in the presence of PCR reaction mix without additional primers. The 3' end of the template-primer hIL-2 DNA will anneal to the 5' end of the template-primer hγ-IFN DNA and extension will produce a 541 bp fragment designated hIL-2/hγ-IFN. The primers hIL-2/P11 and hγ-IFN/P14 are then added, and 40 cycles of PCR are performed to amplify the hIL-2/hγ-IFN product.

The hybrid hIL-2/hγ-IFN vector is constructed by a three part ligation. The 5' end of KT hIL-2 retroviral vector is isolated from Xba I restriction endonuclease digestion. This hγ-IFN/hIL-2 product is digested with Xba I and BstB I to yield a 507 base pair fragment. This fragment is ligated to the Xba I site of the isolated 5' end of KT hIL-2. The 3' end of KT hγ-IFN retroviral vector is isolated from BstB I restriction endonuclease digestion. The BstB I restriction site of the 3' KT hγ-IFN is ligated to the BstB I restriction site, of the construct. This retroviral construct is designated KT hIL-2/hγ-IFN.

Example 2

The Repair of the hγ-IFN Gene

Subsequent sequencing of KT hγ-IFN, the retroviral vector, revealed the presence of a one base pair deletion within the hγ-IFN gene. This deletion is reversed using multi-step PCR procedure.

A. Sequence Selection

Sequences are obtained from IBI Pustell sequence analysis program (Int. Biotech, Inc., New Haven, Conn.).

The following hγ-IFN primer sequences are used:
(Sequence ID No. 32)

5'-3': G CCT CGA GCT CGA GCG ATG AAA TAT ACA AGT TAT ATC TTG

This primer is the sense sequence complimentary to the start codon ATG region extending seven codons upstream of hγ-IFN gene, and is designated hγ-IFN 1b.
(Sequence ID No. 33)

5'-3': GTC ATC TCG TTT CTT TTT GTT GCT ATT

This primer is the anti-sense sequence complimentary to codons 106 to 120 of the hγ-IFN gene, and is designated hγ-IFN Rep B.
(Sequence ID No. 34)

5'-3': AAT AGC AAC AAA AAG AAA CGA GAT GAC

This primer is the sense sequence complimentary to codons 106 to 120 of the γ-IFN gene, and is designated hγ-IFN Rep A.
(Sequence ID No. 35)

5'-3': G CAT CGA TAT CGA TCA TTA CTG GGA TGC TCT TCG ACC TCG

This primer is the anti-sense sequence complimentary to the stop codon ATT region and extending seven codons upstream of the hγ-IFN gene, and is designated hγ-IFN 3b.

B. Initial PCR

A solution of $1\times10^6$ KT hγ-IFN plasmid molecules in 398.0 µl, DI $H_2O$; 50 µl, 10× PCR buffer (500 mM KCl and 200 mM Tris-HCl, pH 8.4; 25 mM $MgCl_2$; 1.0 mg/ml BSA); 5.0 µl, 2.5 mM dATP; 5.0 µl, 2.5 mM dGTP; 5.0 µl, 2.5 mM dCTP; 5.0 µl, 2.5 mM dTTP; 12.0 µl, 18.6 nmol/ml, oligonucleotide hγ-IFN 1b; 15.0 µl, 24.6 nmol/ml, oligonucleotide hγ-IFN Rep B; and 2.5 µl, Taq polymerase is mixed in a microfuge tube and 50 µl is aliquoted into 10 tubes. Similarly, a solution of $1\times10^6$ KT hγ-IFN plasmid molecules in 395.0 µl, DI $H_2O$; 50.0 µl, 10× PCR buffer (500 mM KCl; 200 mM Tris-HCl, pH 8.4; 25 mM $MgCl_2$; 1 mg/ml BSA); 5.0 µl, 2.5 mM dATP; 5.0 µl, 2.5 .mM dGTP; 5.0 µl, 2.5 mM dCTP; 5.0 µl, 2.5 mM dTTP; 13 µl, 23.4 nmol/ml, oligonucleotide hγ-IFN Rep A; 17.0 µl, 18.0 nmol/ml, oligonucleotide hγ-IFN 3b; and 2.5 µl Taq polymerase is mixed in a microfuge tube and 50.0 µl is aliquoted into 10 tubes. The 20 tubes are placed in a PCR machine (Model 9600, Perkin Elmer Cetus; Los Angeles, Calif.). The PCR program regulates the temperature of the reaction vessel in the first cycle at 94° C. for 2 minutes. The next 35 cycles are regulated at 94° C. for 0.5 minutes, then at 55° C. for 0.5 minutes and finally at 72° C. for 1 minute. The final cycle is regulated at 72° C. for 10 minutes. This cycling program is designated Program 10.

Following PCR amplification, 225.0 µl of each reaction tube is mixed with 25.0 µl loading dye (0.25% bromophenol blue, 0.25% xylene cyanol and 50% glycerol, agarose gel loading dye) and loaded into the wells of a 2% agarose gel containing ethidium bromide. The gel is electrophoresed at approximately 90 volts for 1 hour. Ultraviolet light is used to visualize the DNA band separation. Two bands are isolated, one fragment of 250 bp in size and the other of 150 bp in size by electrophoretic transfer onto NA 45 paper as previously described in Example 1C 2(a). Following precipitation, each of the two DNA pellets is resuspended in 20.0 µl. DI $H_2O$ and prepared for further PCR amplification.

C. Annealing and Second Round PCR

A solution of 20.0 µl of the 150 bp PCR DNA; 20.0 µl of the 350 bp PCR DNA: 161.5 µl, DI $H_2O$; 25.0 µl, 10× PCR buffer (500 mM KCl; 200 mM Tris-HCl, pH 8.4; 25 mM $MgCl_2$; and 1 mg/ml BSA); 2.5 µl, 2.5 mM dATP; 2.5 µl, 2.5 mM dGTP; 2.5 µl, 2.5 mM dCTP; 2.5, µl, 2.5 mM dTFP; and 1.25 µl Taq polymerase is mixed in a microfuge tube and 47.3 µl aliquoted into each of 5 tubes. Each tube is placed in a PCR machine (Model 9600, Perkin-Elmer-Cetus, Calif.). The PCR program regulates the temperature of the reaction vessel for 5 cycles at 94° C. for 0.5 minutes. The next cycle is regulated at 55° C. for 1 minute. Following this cycle, 1.2 µl hγ-IFN 1b and 1.5 µl hγ-IFN 3b are added to the reaction mixture. The tubes are then PCR amplified using program 10. The product is designated rhγ-IFN.

D. Creation and Isolation of Blunt-Ended rhγ-IFN PCR DNA Fragment

The PCR amplified rhγ-IFN DNA is blunt ended using T4 polymerase. Specifically, 120.0 µl rhγ-IFN PCR solution is mixed with 1.25 µl, 2.5 mM dATP; 1.25 µl, 2.5 mM dGTP; 1.25 µl, 2.5 mM dCTP; 1.25 µl, 2.5 mM dTTP; 1 µl, T4 DNA polymerase; and 1.0 µl Klenow fragment. This mixture is incubated at room temperature for 10 minutes. Following incubation, 13.0 µl of agarose gel loading dye is added to the mixture and this solution is loaded into a 1% agarose gel. The gel is electrophoresed at approximately 90 volts for 1 hour. Ultraviolet light is used to visualize the DNA banding. A 500 bp band is isolated by electrophoretic transfer onto NA45 paper as described in Example 1C 2(a). Following precipitation, the DNA pellet is resuspended in 12.0 µl DI $H_2O$.

The isolated 500 bp fragment is blunt ended using T4 polynucleotide kinase. Specifically, 1.0 mg of this fragment is mixed with 1.5 µl 10× kinase buffer (0.5 mM Tris-HCl, pH 7.6; 0.1 mM $MgCl_2$; 50 mM dithiothreitrol; 1 mM spermidine; 1 mM EDTA); 1.5 µl, 10 mM ATP; and 1.0 µl, T4 polynucleotide kinase, and incubated at 37° C. for 30 minutes.

E. Ligation of rhγ-IFN PCR DNA Into the $SK^+$ Vector

The rhγ-IFN PCR DNA is ligated into the $SK^+$ vector as described in Example 1C 2(b). A solution of 2.0 µl rhγ-IFN PCR DNA-kinase reaction mixture; 2.0 µl CIP treated $SK^+$ vector; and 1.0 µl, T4 DNA ligase is incubated at 16° C. for 4 hours. DH5α bacteria is transformed as described in Example 1C 2(c).

F. Ligation of rhγ-IFN Gene Into Retroviral Vector

Ligation of rhγ-IFN gene into retroviral vector is performed described in Example 1C 2(c). The new vector is designated KT rhγ-IFN.

Example 3

Transduction of Packaging Cell Lines (CA and DA) and Murine Tumor Cell Lines (B16F10 and L33) With mγ IFN Retroviral Vector A. Plasmid DNA Transfection 293 2-3 cells (a cell line derived from 293 cells ATCC No. CRL 1573, WO 92/05266) $5\times10^5$ cells are seeded at approximately 50% confluence on a 6 cm tissue culture dish. The following day, the media is replaced with 4 ml fresh media 4 hours prior to transfection. A standard calcium phosphate-DNA coprecipitation is performed by mixing 10.0 µg of KT mγ-IFN plasmid and 10.0 µg MLP G plasmid with a 2M CaCl solution, adding a 1× Hepes buffered saline solution, pH 6.9, and incubating for 15 minutes at room temperature. The calcium phosphate-DNA coprecipitate is transferred to the 293 2-3 cells, which are then incubated overnight at 37° C., 5% $CO_2$. The following morning, the cells are rinsed 3 times in 1× PBS, pH 7.0. Fresh media is added to the cells, followed by overnight incubation at 37° C., 10% $CO_2$. The following day, the media is collected off the cells and passed through a 0.45 µm filter. This supernatant is used to transduce packaging and tumor cell lines.

B. Packaging Cell Line Transduction

CA cells (an amphotropic cell line derived from CF-2 cells, ATCC No. 6574, WO 92/05266) are seeded at 1×10$^5$ cells/6 cm dish. One-half milliliter of the freshly collected 293 2–3 supernatant is added to the CA cells; The following day, G418 is added to these cells and a drug resistant pool is generated over a period of a week. This pool of cells is dilution cloned by adding 0.8–1.0 cells to each well of 96 well plates. Twenty-four clones were expanded to 24 well plates, then to 6 well plates, at which time cell supernatants are collected for titering. CA clones are selected for vector production. A CA clone having a titer of approximately 5×10$^6$ cfu/ml is selected, and designated mγ-IFN #23.

DA cells (referred to as DA2 in WO 92/05266), an amphotropic cell line derived from D 17 cells ATCC No. CCL-183, are seeded at 5×10$^5$ cells/10 cm dish. 0.5 ml of the 293 2–3 supernatant stored at –70° C. is added to the DA cells. The following day, G418 is added to these cells and a drug resistant pool is generated over the period of a week. DA clones are selected for vector production.

C. Murine Tumor Cell Line Transductions

1. L33

L33 cells (Dennert, USC Comprehensive Cancer Center, Los Angeles, Calif., Patek, et. al., *Int. J. of Cancer* 24:624–628, 1979) are seeded at 1×10$^5$ cells/6 cm dish. 1.0 ml of the 293 2–3 supernatant stored at –70° C. is added to the L33 cells. The following day, G418 is added to these cells and a drug resistant pool is generated over a period of a week. This pool of cells is dilution cloned by adding 1.0 cell to each well of 96 well plates, followed by the expansion of clones to 24 well plates, and then 6 well plates, after which cell lysates are prepared for analysis of major histocompatability complex (MHC) expression. A clone, L33/mγ-IFN #15, which had significantly increased levels of MHC expression is used in subsequent mouse studies.

2. B16F10

B16F10 cells (Dennert, USC Comprehensive Cancer Center, Los Angeles, Calif.; Warner, et. al., *Nature* 300:113–121, 1982) are seeded at 2×10$^5$ cell/10 cm dish with a 10 µg/ml polybrene (1,5-dimethyl-1,5-diazaundecamethylene polymethobromide, Sigma, St. Louis, Mo.). 0.1 ml of supernatant from the CA mγ-IFN pool is added to the cells and incubated for 6 hours at 37° C., 10% CO2. G418 is added after incubation and a drug resistant pool is generated. This pool is dilution cloned by adding 1.0 cells to each well of 96 well plates. Twenty-four clones are expanded to 24 well plates, then to 6 well plates, at which time cell lysates are made for analysis of MHC expression. A clone, B16F10/mγ-IFN #4, having significantly increased levels of MHC expression is used in subsequent mouse studies.

3. CT 26 And Lewis Lung Tumor Cells

Colon tumor 26 (CT 26) (Brattain, Baylor College of Medicine, Houston Tex.) and Lewis lung tumor (LLT) (Waude, Southern Research Institute, Birmingham, Ala., ATCC No. CRL 1642) cells are seeded 1×10$^5$ cells/6 cm plate for each cell line in DMEM with 10% FBS and 4 g/ml polybrene and incubated for 24 hours at 37° C., 10% CO$_2$. After incubation, 1.0 ml of KT mγ-IFN retroviral vector (9×10$^6$ cfu/ml) is added to each respective cell line and incubated for 24 hours at 37° C., 10% CO$_2$. Following incubation, the medium is changed and replaced with DMEM with 10%, FBS and 400 µg/ml G418. These cell lines are kept under G418 selection for approximately two weeks. Selected CT 26 and LLT resistant pools are dilution cloned by adding 1.0 cell to each well of 96 well plates. Two 96 well plates are seeded for each G418-selected pool. CT 26 and LLT mγ-IFN expressing clones are expanded into 24 well plates and then to 6 well plates. Lysates are prepared of each clone and analyzed for up-regulated MHC protein expression by Western blot analysis. A clone, CT 26/mγ-IFN #10, having up-regulated MHC protein expression is selected. All LLT studies are conducted using the non-clonal pool of the mγ-IFN expressing LLT cells.

Example 4

Transduction of Packaging Cell Line and Human Melanoma Cell Lines With hγ-IFN Retroviral Vector A. Plasmid DNA Transfection 5×10$^5$ $^{293}$ $^{2-3}$ cells (described in patent application WO 92/05266) are seeded at approximately 50% confluence on a 6 cm tissue culture dish. The following day, the media is replaced with 3 ml fresh media 4 hours prior to transfection. At the time of transfection, 5.0 µl of KT hγ-IFN plasmid is mixed with 2.0 µl MLP G plasmid in 0.1× Tris-EDTA, 150 mM, pH 7.4. A standard calcium phosphate-DNA coprecipitation is performed mixing the DNA with a 2M CaCl solution, adding a 1× Hepes buffered saline solution, 2M, pH 6.9, and incubating for 15 minutes at room temperature. The calcium phosphate-DNA coprecipitate is transferred to the 293 2–3 cells, which are then incubated overnight at 37° C., 5% CO$_2$. The following morning, the cells are rinsed 3 times in 1× PBS, pH 7.0. Fresh media is added to the cells, followed by overnight incubation at 37° C. in 10% CO$_2$. The following day, media is collected off the cells and passed through a 0.45 µm filter. The filtered supernatant is stored at –70° C. for use in packaging cell transductions.

B. Packaging Cell Transduction

CA 6BM cells (CA cells described in patent application WO 92/05266 cured of mycoplasma by 6 cycles of BM cycline) are seeded at 1× 10$^5$ cells/6 cm dish with 4 µg/ml polybrene. The following day, 0.2 ml of the supernatant collected off the 293 2–3 transiently transfected cells in Example 4A is added to the media of the CA cells. These cells are then incubated overnight at 37° C., 5% CO$_2$. The following day, the media is replaced with fresh media containing 800 µg/ml G418. Cells are grown to confluence and expanded under G418 selection. Upon subsequent confluence, a majority of the cells are frozen while a culture is maintained free of G418. When cells once again reached confluence, the supernatant is collected for analysis of the presence of hγ-IFN by viral inhibition assay. The pool of cells is dilution cloned by adding 1.0 cell to each well of 96 plates. G418 is included in the culture media. Twenty-four clones are expanded and analyzed for titer, the presence of helper virus, expression, and functional transfer of expression.

C. Second Generation Transfection/Transduction

1. CA 6BM Transduction 5.0×10$^5$ DX cells (a cell line derived from D 17 cells ATCC No. 183, WO 92/05266) are seeded at approximately 50% confluence on a 6 cm tissue culture dish. The following day, the media is replaced with 4 ml fresh media 3.5 hours prior to transfection. A standard calcium phosphate-DNA coprecipitation is performed by mixing 10.0 µg of KT hγ-IFN plasmid with a 120 ml 2M CaCl solution, adding a 240 ml of a 2M 1× Hepes buffered saline solution, pH 6.9, and incubating for 15 minutes at room temperature. The calcium phosphate-DNA coprecipitate is transferred to the DX cells, which are then incubated overnight at 37° C., 5% CO$_2$. The following morning, the cells are rinsed 3 times with 3 ml of 145 mM 1× PBS, pH 7.0. Fresh media is added to the cells, followed by overnight incubation at 37° C., 10%

$CO_2$. The following day, the media is collected off the cells, passed through a 0.45 μm filter, and stored at −70° C.

Three days later, CA 6BM cells are seeded with 4 g/ml polybrene at $1\times10^5$ cells/6 cm dish. The following day, 5.0 and 1.0 ml of the supernatant collected from the DX transfected cells is added to the CA 6BM cells. These mixtures are incubated for 4 hours at 37° C., 10% $CO_2$. Following the incubation, the cells are dilution cloned in the presence of 800 g/ml G418 at 10 and 30 cells/well of 96 well plates. Forty clones are expanded to 24 well plates and then to 6 well plates. The cell supernatants are collected and titered. Clones with titers of at least $1\times10^6$ cfu/ml are placed in roller bottles and monitored for the generation of helper virus. This packaging cell line is designated CA/hγ-IFN.

2. DA Transduction $5.0\times10^5$ DX cells are seeded at approximately 50% confluence on a 6 cm tissue culture dish. The following day, the media is replaced with 4 ml fresh media 4 hours prior to transfection. A standard calcium phosphate-DNA coprecipitation is performed by mixing 2.0 μl, 6.0 μg, of KT hγ-IFN plasmid with a 120 ml 2M CaCl solution, adding 240 ml of a 2M 1× Hepes buffered saline solution, pH 6.9, and incubating for 15 minutes at room temperature. The calcium phosphate-DNA coprecipitate is transferred to the DX cells, which are then incubated overnight at 37° C., 5% $CO_2$. The following morning, the cells are rinsed 3 times with 3 ml of 145 mM 1× PBS, pH 7.0. Fresh media is added to the cells and followed by overnight incubation at 37° C., 10% $CO_2$. The following day, the media is collected off the cells and passed through a 0.45 μm filter.

The previous day, DA cells (previously described in patent application WO 92/05266 as DA2) are seeded at $1\times10^5$ cells/6 cm dish. 1.0 ml of the freshly collected DX supernatant is added to the DA cells. The following day, G418 is added to these cells and a drug resistant pool is generated over a 2-week period. The pool of cells is dilution cloned by adding 1.0 cell to each well of 96 well plates. Twenty-four clones are expanded to 24 well plates, then to 6 well plates. The cell supernatants are collected for titering and clones with titers of at least $5\times10^5$ cfu/ml are selected. A DA clone hIFNr #15 is selected and designated DA/hγ-IFN.

D. Human Melanoma Transductions

Melanoma cell lines DM6, DM92, DM252, DM265, DM262 and DM259 were established from human tumor biopsies (Dr. Hilliard Seigler, Duke University and Viagene, Inc.) by mincing the tumor into 1 mm chunks or grinding the tumor through a Cellector mesh and plating them on a tissue culture flask. Cells were repeatedly passaged by differential trypsinization, where the cells are trypsinized and the tumor cells are removed before the fibroblasts lift off the flask. The cells were carried until constant growth was observed and sufficient cell numbers were generated and frozen.

After establishment, each cell line was seeded at $10^6$ cells/10 cm dish with 4 μ/ml polybrene. The following day, 5–10 mls of filtered supernatant from the DA/hγ-IFN pool was added to each of the cell cultures. This corresponds to a multiplicity of infection (MOI) of 5–10. The next day, the cells were selected with 800 μg/ml of G418. Samples of the supernatants of all transduced cell lines were saved twice weekly. The supernatants were filtered through a 0.45 μm filter and stored at −70° C. until assayed for γ-IFN expression as described in Example 6. The cultures were maintained until selection was complete and sufficient cell numbers were generated and frozen.

Example 5

MHC Class I Expression

A. Determination of Mouse MHC Class I Expression by Western Blot Analysis

RIPA lysates are prepared from confluent plates of cells. Specifically, the media is first aspirated off the cells. Depending upon the size of the culture plate containing the cells, a volume of 100.0 to 500.0 μl ice cold RIPA lysis buffer (10 mM Tris, pH 7.4; 1% Nonidet P40 (Calbiochem, Calif); 0.1% SDS; 150 mM NaCl) is added to the cells. Cells are scrapped from plates using a micropipet and the mixture is transferred to a microfuge tube. The tube is centrifuged for 5 minutes to precipitate cellular debris and the lysate supernatant is transferred to another tube. The lysates are electrophoresed on a 10% SDS-PAGE gel and the protein bands are transferred to an Immobilon membrane in CAPS buffer (10 mM CAPS, pH 11.0; 10% methanol) at 10 to 60 volts for 2 to 18 hours. The membrane is transferred from the CAPS buffer to 5% Blotto (5% nonfat dry milk; 50 mM Tris, pH 7.4; 150 mM NaCl; 0.02% sodium azide, and 0.05% Tween 20) and probed with a rat IgM antibody, 72.14S (Richard Dutton, UCSD, San Diego, Calif.). This antibody probe is directed against a conserved intracellular region of the mouse MHC Class I molecule. Antibody binding to the membrane is detected by the use of $^{125}$I-Protein A.

Figure 2:
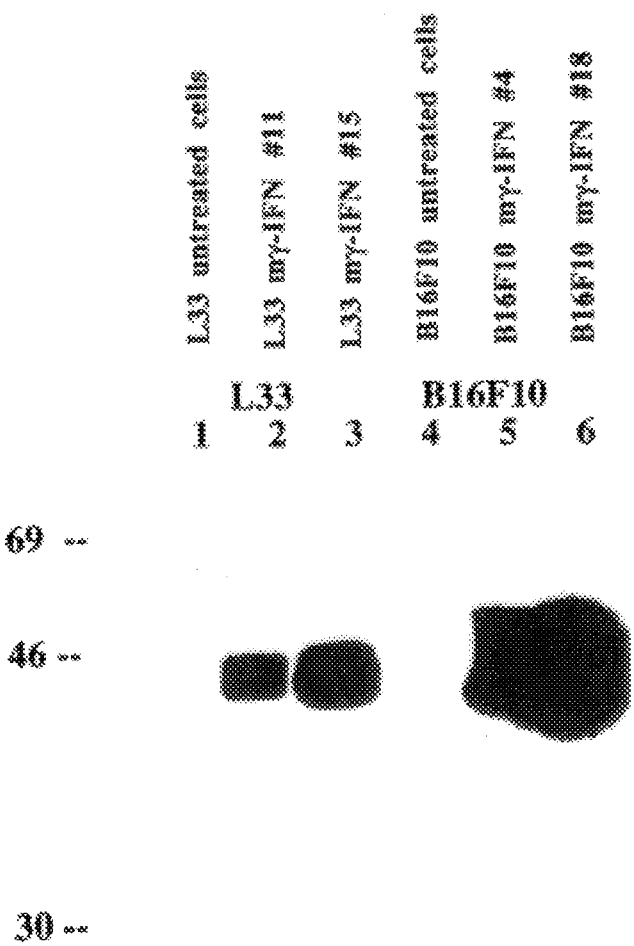
FIG. 2 is a Western blot which depicts MHC Class I protein expression in L33 and B16F10 cell lines.

B. Analysis of MHC Expression in Murine Tumor Cell Lines With and Without mγ-IFN Retroviral Vector MHC expression is confirmed by Western blot and FACS analysis. Specifically, L33, CT 26, and LLT parent cell lines express relatively normal levels of MHC Class I protein and the B16F10 parent cell line has down-regulated levels of MHC Class I protein. The mγ-IFN-transduced pools and clones of these cell lines express greater levels of MHC Class I than their corresponding parent cell lines which is demonstrated by Western blot and FACS analysis. Western blot of lysates of various CT 26 mγ-IFN, LLT mγ-IFN subclones and the parent CT 26 and LLT cell lines show up-regulated MHC Class I expression. A Western blot analysis of two L33 mγ-IFN subclones, two B16F10 mγ-IFN subclones, parent 1.33 cell line, and parent B16F10 cell line illustrates the up-regulated MHC Class I expression of the mγ-IFN clones as compared to the parent cells, FIG. 2. FACS analysis of L33 and two L33 mγ-IFN subclones illustrates that the subclones have considerable more MHC Class I expressed on the surface as compared to the parent cells. FACS analysis is performed on harvested cells. Specifically, cells are incubated with an MHC Class I specific antibody 34.4 anti-$D^d$ antibody (Dutton, UCSD; San Diego, Calif.). This bound antibody is detected by incubating the 34.4 anti-$D^d$ bound cells with fluoroscene conjugated rabbit anti-mouse IgG antibody (Capell, N.C.). Fluorescent emission from the cell bound antibody-fluoroscene conjugate is detected and quantitated by FACS, FIG. 21.

C. MHC Expression in Tumor Cells Treated With Recombinant mγ-IFN In Vitro $1.0\times10^6$ cells treated with recombinant mγ-IFN in vitro are plated the day before treatment so that 50% confluency is reached by the next day. Recombinant mγ-IFN (Genzyme, Cambridge, Mass.) is added at concentrations ranging from 0 to 500 U/ml to duplicate plates of the cells under study. The plates are incubated for 48 hours at 37° C. and cells are lysed and analyzed by Western blot to determine an increase in MHC Class I expression. The data is presented in FIG. 3.

In order to study the effects of recombinant mγ-IFN on MHC expression levels of exogenously treated cells following removal of the IFN, multiple plates of L33 cells are seeded the day before treatment so that 50% confluency is reached the next day. Recombinant mγ-IFN is added at a final concentration of 200 U/ml, and the cells are incubated for 48 hours. The cells are then washed with PBS, fresh media is added, and the cells are lysed 0, 24, 48, and 72 hours following the PBS wash. The cell extracts are analyzed by Western blot for MHC Class I expression. Results indicate that by 48 hours after removal of the IFN there is a significant decrease in cellular MHC Class I expression and this decrease continues with time (FIG. 3A).

Example 6

Determination of γIFN Activity

A. mγ-IFN Assay

The activity of γ-IFN is quantified by Lee Biomolecular, San Diego, Calif., as the measurement of the protective effect against cytocidal infection with encephalomyocarditis (EMC) virus. A mouse cell line L929, ATCC CCL 1, is used to assay for mγ-IFN. The filtered supernatants are added to the cells at different concentrations and then the cells are challenged with the EMC virus. Mouse γ-IFN samples are co-assayed with the appropriate NIH, reference reagents and the results are normalized to NIH reference units (U/ml) (Brennan et al., Biotechniques 1:78, 1983).

Samples of the supernatants of all transduced cell lines are saved when the cells are fed twice weekly. The supernatant is filtered through a 0.45 μm filter and stored at -70° C. until testing. Activities are recorded for the cell types CT 26, BC10ME, LLT, and B16F10. This data is presented in Tables 3 and 4.

TABLE 3

γ-IFN PRODUCTION IN VARIOUS BALB/C CELL LINES

| Cell Type | U/ml |
|---|---|
| rCT26 | 3.5 |
| CT26 IFN pool | 3400 |
| CT26 IFN clone #10 | 4500 |
| BC10ME | 22 |
| BC10ME IFN pool | 110 |
| L33 | <0.3 |
| L33 α-IFN | 7.7 |

ND = Not Done

TABLE 4

γ-IFN PRODUCTION IN VARIOUS C57BL/6 CELL LINES

| Cell Type | U/ml |
|---|---|
| LLT | <0.69 |
| LLT IFN pool | 82 |
| LLT IFN #21 | 40 |
| LLT IFN #28 | 2.1 |
| LLT IFN pool tumor | 21 |
| LLT IFN pool lg met | 11 |
| B16F10 | <2.6 |
| B16F10 IFN #4 | 90 |

Example 7

Tumorigenicity of B16F10 and B16F10mγ-IFN #4 Cells

Parental B16F10 and B16F10/mγ-IFN#4 cells are harvested, counted, and resuspended to a concentration of $8 \times 10^5$ cells/ml in Hanks buffered salt solution (HBSS, Irvine Scientific, Calif.). Two Black 6 mice (Harlan Sprague-Dawley, Indianapolis, Ind.) are injected intravenously (i.v.) with 0.5 ml of the B16F10 cell suspension ($3 \times 10^5$ cells). Five C57 B1/6 mice are injected i.v. with 0.5 ml of the B16F10 IFN#4 cell suspension. Fourteen days after injection the lungs are removed from the mice, stained and preserved in Bouin's Solution (Sigma, St. Louis, Mo.). The 4 lobes of the lungs are separated, examined under 10× magnification, and the number of black tumors present on each is determined.

Figure 6:
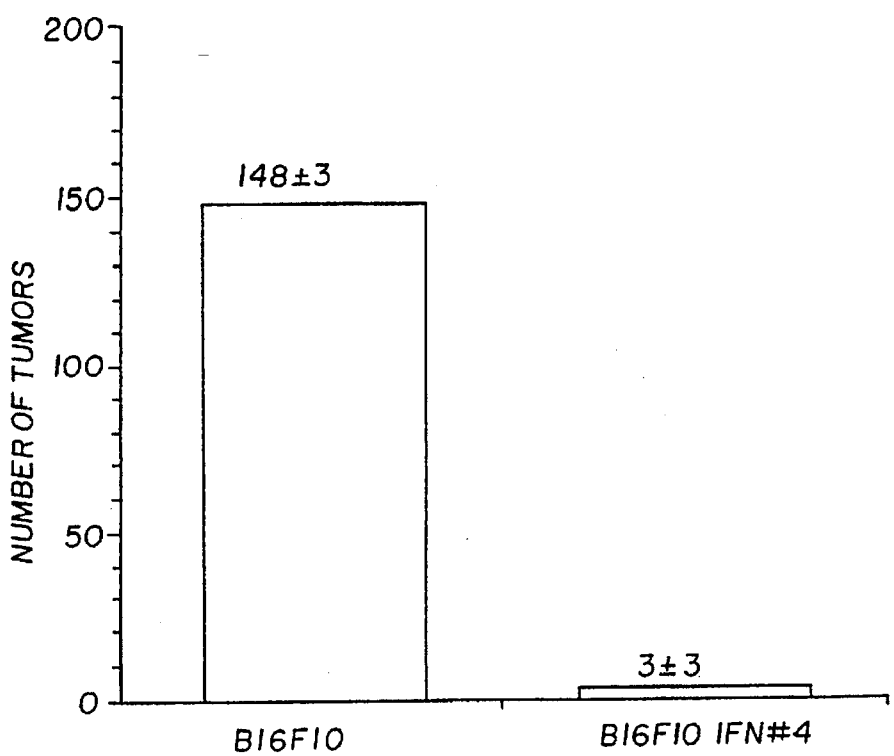
FIG. 6 is a bar graph which illustrates tumor growth in Black 6 mice which were injected with either B16F10, or B16F10 mγ-IFN #4 cells.

The average number of tumors per lung for each group and the standard deviation is shown in FIG. 6.

Example 8

B16F10 CTL Assays

A. Experiment 1

Figure 4A:
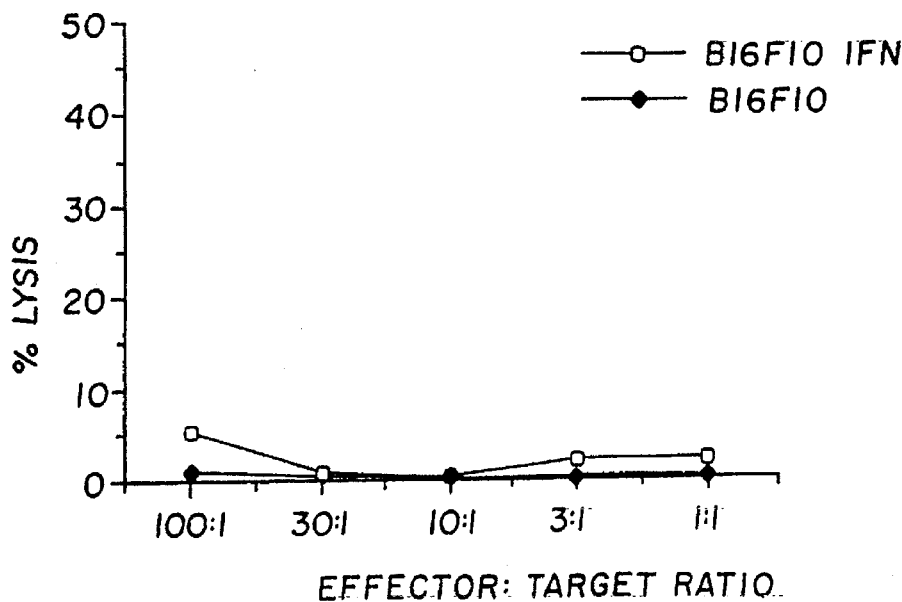
FIG. 4A is a graph which illustrates the induction of anti-B16F10 CTL response in Black 6 mice.
Figure 4B:
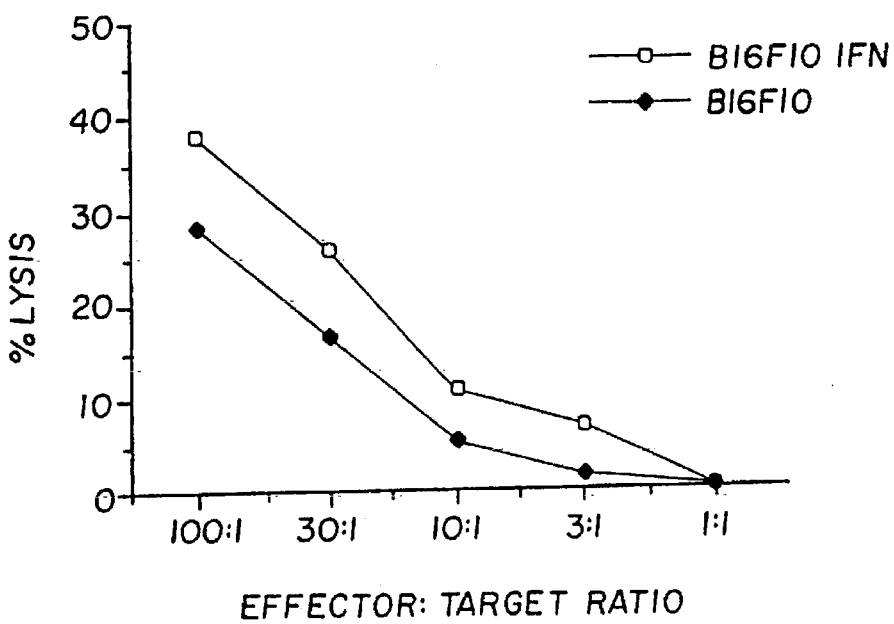
FIG. 4B is a graph which illustrates the induction of anti-B16F10 murine gamma interferon #4 CTL response in Black 6 mice.

B16F10/mγ-IFN #4 cells are irradiated with 10,000 rad of $^{60}$Co at the Salk Institute. Two Black 6 mice are injected intraperitoneally (i.p.) with $1 \times 10^7$ irradiated cells in 1.0 ml HBSS. Three weeks later, the mice are injected i.v. with $3 \times 10^5$ live B16F10 cells in 0.5 ml HBSS. Two Black 6 control mice are also injected with the same dose. Fourteen days later, the lungs and spleens are removed from the mice. The lungs are stained and preserved in Bouin's Solution. The 4 lobes of the lungs are separated, examined under 10× magnification and the number of black tumors present in each is determined. No tumors were visible on any of the lungs. Splenocytes are removed from the spleens, washed three times in HBSS, and resuspended in CTL media containing RPMI and 5% heat inactivated FBS at $3 \times 10^7$ cells/10ml in T-25 flasks. Sixty thousand B16F10 cells irradiated with 10,000 rad of $^{60}$Co at the Salk Institute are added to the flasks. The cells are incubated for 6 days at 37° C., 5% $CO_2$. After incubation, a standard 5-hour CTL assay is performed using both B16F10 and B16F10/hγ-MFN #4 cells as targets. The data is presented in FIG. 4.

Six- to eight-week-old female Balb/C mice (Harlan Sprague-Dawley, Indianapolis, Ind.) are injected twice i.p. with $1 \times 10^7$ vector transduced cells irradiated with 10,000 rads at room temperature. Animals are sacrificed 7 days later and $3 \times 10^6$ splenocytes/ml are cultured/n vitro with $6 \times 10^4$ irradiated syngeneic transduced cells/ml in T-25 flasks. Culture medium consists of RPMI 1640; 5% FBS, heat-inactivated; 1 mM pyruvate; 50 μg/ml gentamycin and $10^{-5}$M 2-mercaptoethanol. Effector cells are harvested 4–7 days later and tested using various effector:target cell ratios in 96 well microtiter plates in a standard 4–6 hour assay. The assay employs $Na_2$ $^{51}CrO_4$-labeled, 100 uCi, 1 hr at 37° C. (Amersham, Arlington Heights, Ill.), target cells at $1 \times 10^4$ cells/well in a final volume of 200.0 μl. Following incubation, 100.0 μl of culture medium is removed and analyzed in a Beckman gamma spectrometer (Beckman; Dallas Tex.). Spontaneous release (SR) is determined as CPM from targets plus medium and maximum release (MR) is determined as CPM from targets plus 1M HCl. Percent target cell lysis is calculated as: [(Effector cell+target CPM) −(SR)/(MR)−(SR)]×100. Spontaneous release values of targets are typically 10%–20% of the MR.

B. Experiment 2

B16F10/mγ-IFN#4 cells are harvested, resuspended in HBSS, and irradiated with 20,000 rad of $^{60}$Co at the Salk Institute. Cells are aliquoted at 2 different concentrations: $1 \times 10^7$ cells/ml and $1 \times 10^7$ cells/0.1 ml. Three groups consisting of 4 Black 6 mice are injected. The first group of three mice receives no cells, the second group receives 1.0 ml i.p., $1.0 \times 10^7$ total cells and the third group receives 0.1 ml i.m., $1 \times 10^7$ total cells.

Figure 5:
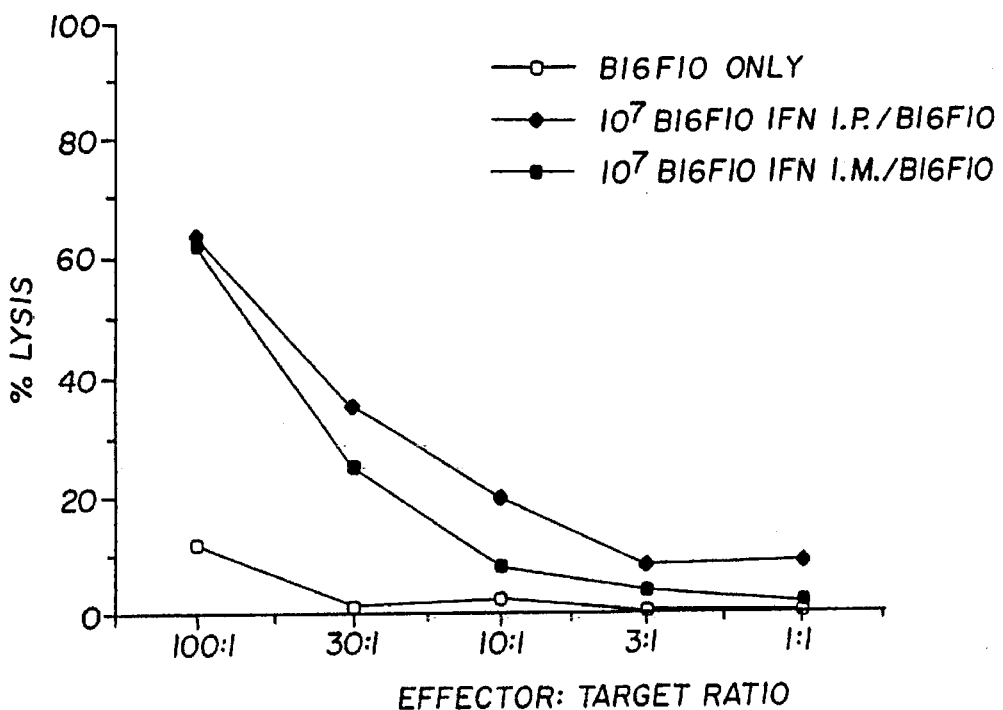
FIG. 5 is a graph which illustrates the induction of anti-B16F10 murine gamma interferon #4 CTL response in mice, following either i.p. or i.m. injection.

Seven days after injection, all mice are i.v. injected with. 0.5 ml live B16F10-cells at $8 \times 10^5$ cells/ml HBSS. Fourteen days after i.v. injection, the spleens are removed from the mice. The splenocytes are isolated from the spleens, washed three times in HBSS, and resuspended in CTL media at 3×10⁷ cells/10 ml in T-251 flasks. Sixty thousand B16F10 cells irradiated with 20,000 rad of $^{60}$Co at the Salk Institute are added to the flasks. The cells are incubated for 5 days at 37° C. 5% $CO_2$. After incubation, at which time a standard 6.5 hour CTL assay is performed using B16F10 cells as targets. The data is presented in FIG. 5.

Example 9

B16F10 Vaccine Studies

A. Experiment 1

B16F10 and B16F10/mγ-IFN#4 cells are harvested and resuspended in HBSS. The cells are irradiated with 10,000 rad of $^{60}$Co. The cell concentration for both cell suspensions is adjusted to 8×10⁵ cells/ml. Three groups of three Black 6 mice are injected. The first group is injected i.v. with 0.5 ml, 4.0×10⁵ irradiated B16F10 cells. The second group is injected i.v. with 0.5 ml of the irradiated B16F10/mγ-IFN#4 cells and the final group did not receive cells. Ten days after injection, all 9 mice are injected i.v. with 0.5 ml live B16F10 cells at 6.0×10⁵ cells/ml HBSS. Fourteen days after i.v. injection, the lungs are removed from the mice and stained and preserved in Bouin's Solution. The 4 lobes of the lungs are separated, examined under 10× magnification, and the number of black tumors present in each is determined.

Figure 7:
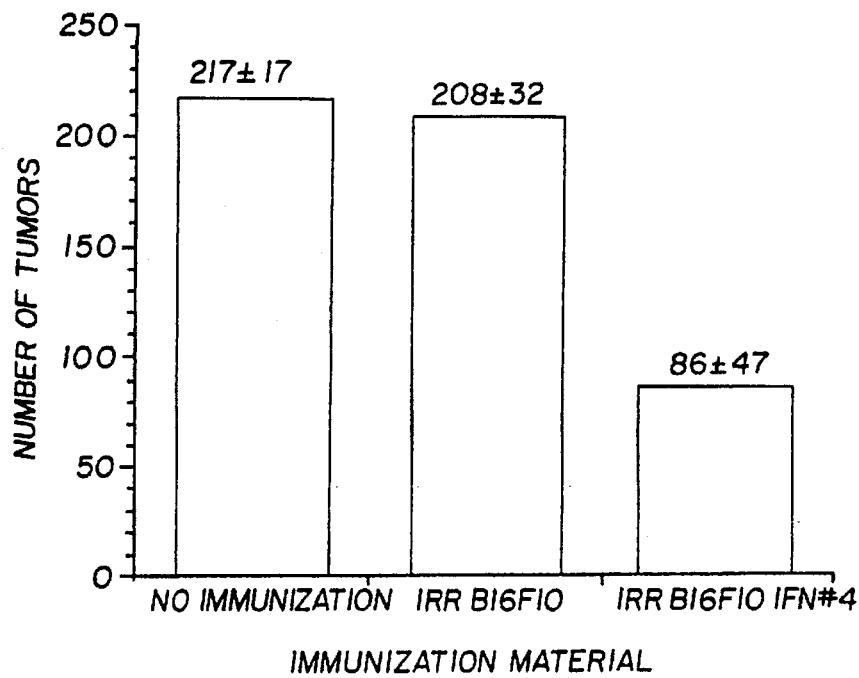
FIG. 7 is a bar graph which illustrates tumor growth in Black 6 mice challenged with B16F10 cells, after vaccination with either irradiated B16F10 cells or irradiated B16F10 murine gamma-interferon #4 cells.

The average number of tumors per lung for each group and the standard deviation is shown in FIG. 7.

B. Experiment 2

B16F10/hγ-IFN#4 cells are harvested, resuspended in HBSS, and irradiated with 10,000 rad of $^{60}$Co. Cells are aliquoted at 5 different concentrations: 4×10⁵ cells/0.5 ml, 5×10⁵ cells/ml, 1×10⁷ cells/ml, 5×10⁶ cells/0.1 ml, and 1×10⁷ cells/0.1 ml. Six groups of 4 Black 6 mice are injected. Group one is not injected with cells. Group two is injected with 0.5 ml i.v., 4×10⁵ B16F10/mγ-IFN#4 cells. The third group is injected with 1.0 ml i.p., 5×10⁶ B16F10/mγ-IFN#4 cells. The fourth group is injected with 1.0 ml i.p., 1×10⁷ B16F10/mγ-IFN#4 cells. The fifth group is injected with 0.1 ml intramuscularly (i.m.), 5×10⁶ B16F10/mγ-IFN#4 cells and the final group is injected with 0.1 ml i.m., 1.0×10⁷ B16F10/mγ-IFN#4 cells. Seven days after injection all mice are injected i.v. with 0.5 ml live B16F10 cells at 6.0×10⁵ cells/ml HBSS. Fourteen days after i.v. injection the lungs are removed from the mice, stained and preserved in Bouin's Solution. The 4 lobes of the lungs are separated, examined under 10× magnification, and the number of black tumors in each lung is determined.

Figure 8:
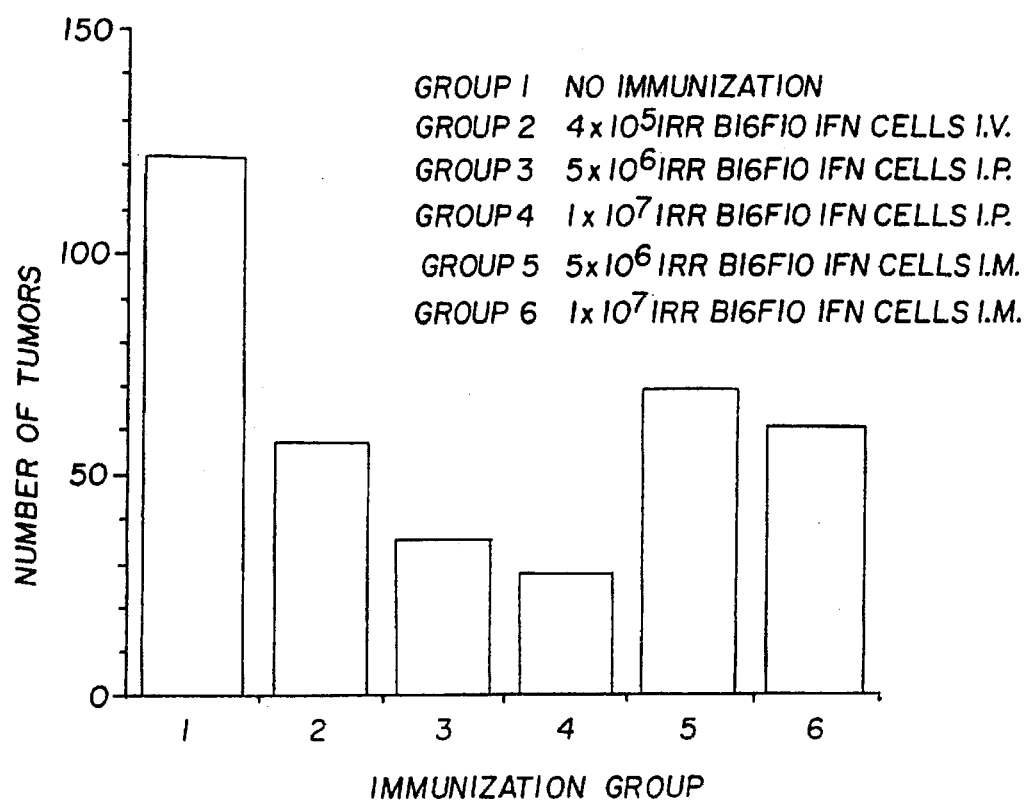
FIG. 8 is a bar graph which illustrates tumor growth following general different vaccination regimens with either irradiated B16F10 cells or irradiated B16F10 murine gamma interferon #4 cells.

The average number of tumors per lung for each group and the standard deviation, is shown in FIG. 8.

Example 10

Comparison of Tumorigenicity Properties of Cells Treated with mγ-IFN and Recombinant mγ-IFN Protein A. Experiment 1

The following experiment is performed to determine whether tumor cells treated with mγ-IFN would grow differently in vivo as compared with tumor cells that continually express mγ-IFN. Three separate groups of ten Balb/C mice are subcutaneously injected with either 3×10⁶ L33 cells, 3×10⁶ L33 cells treated with 400 units of recombinant mγ-IFN for three days in vitro prior to injection, or 3×10⁶ cells of a clone of mγ-IFN vector-modified L33 tumor cells, L33/mγ-IFN #15. Prior to injection, these cells are grown in 10 cm Falcon tissue culture dishes using DMEM with 10% FBS. The cells are harvested with Versene (Irvine Scientific, California) and resuspended in HBSS at a concentration of 1.5×10⁷ per ml. Three million cells of each 1 of the L33 subtypes stated above are injected subcutaneously near the sternum of each animal in a total volume of 0.2 ml. Tumor growth is recorded weekly. The volume of each tumor is determined by measuring the length, width and height of the tumor using a Castroviejo Caliper from Roboz Instruments, Germany. The average tumor size is compared with the average of tumor growth in the other two groups.

Figure 9:
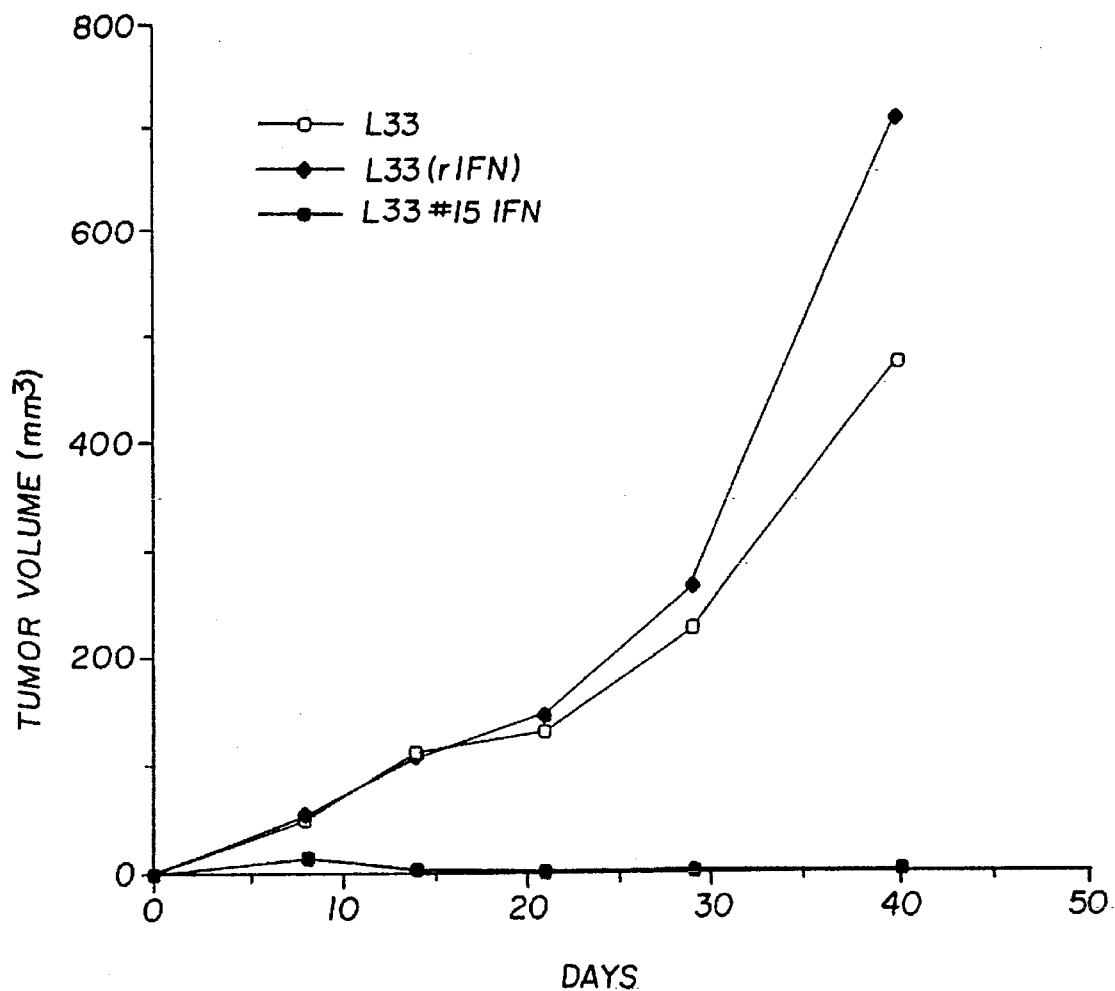
FIG. 9 is a graph which illustrates tumor growth in Balb/C mice which were injected with either $6 \times 10^6$ L33 cells, L33 cells treated with recombinant murine gamma-interferon, or L33 murine gamma-interferon #15 cells.

The data indicate that the L33 cells treated with recombinant mγ-IFN grow similarly to the L33 parent tumor line. In contrast, the L33/mγ-IFN #15 clone that consistently expresses mγ-IFN is rejected, FIGS. 9 and 21. In summary, the tumor cells expressing mγ-IFN can induce a more potent and complete immune response than the tumor cells treated in vitro with mγ-IFN.

B. Experiment 2

Figure 10:
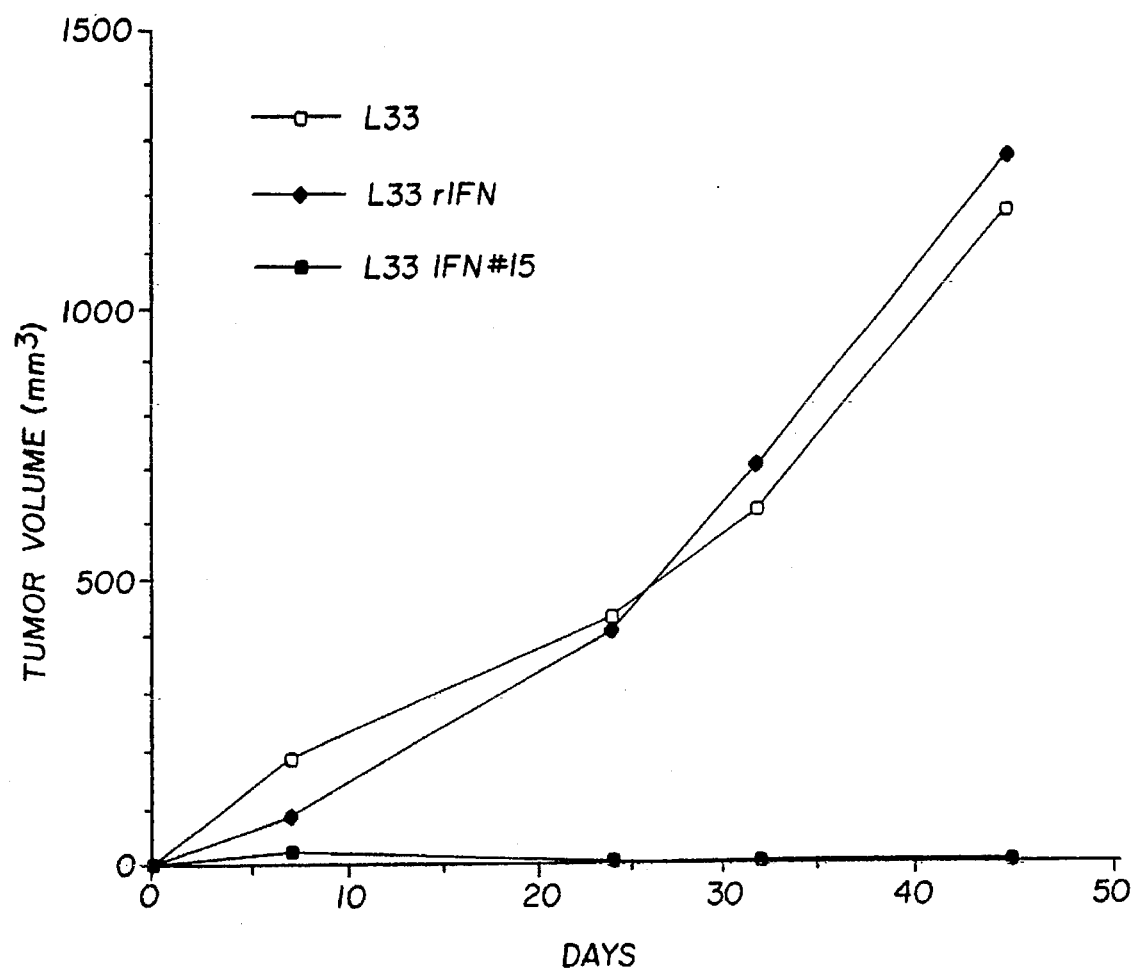
FIG. 10 is a graph which illustrates tumor growth in Balb/C mice which were injected with either $6 \times 10^6$ L33 cells, L33 cells treated with recombinant murine gamma-interferon, or L33 murine gamma-interferon #15 cells.

This experiment is identical to Experiment 1, with the following exception. Instead of injecting 3×10⁶ cells of either L33, L33 treated in vitro with recombinant mγ-IFN or L33/mγ-IFN #15, 6×10⁶ cells of each type are used as the inoculum in the animals. The data indicates that when twice the number of cells are injected, tumor cells expressing mγ-IFN, induce a more potent and complete immune response than the cells treated in vitro with mγ-IFN, FIG. 10.

C. Tumorgenicity of L33 Cells Expressing mγ-IFN in Nude Mice

Tumorgenicity is determined by monitoring L33/mγ-IFN #15 cell growth in mice with impaired T-cell mediated immunity. Two groups of 7 Balb/C nude mice are injected with either 6×10⁶ L33 or 6×10⁶ L33/mγ-IFN #15. Tumor growth is monitored and average measurements are compared between the two groups.

Figure 11:
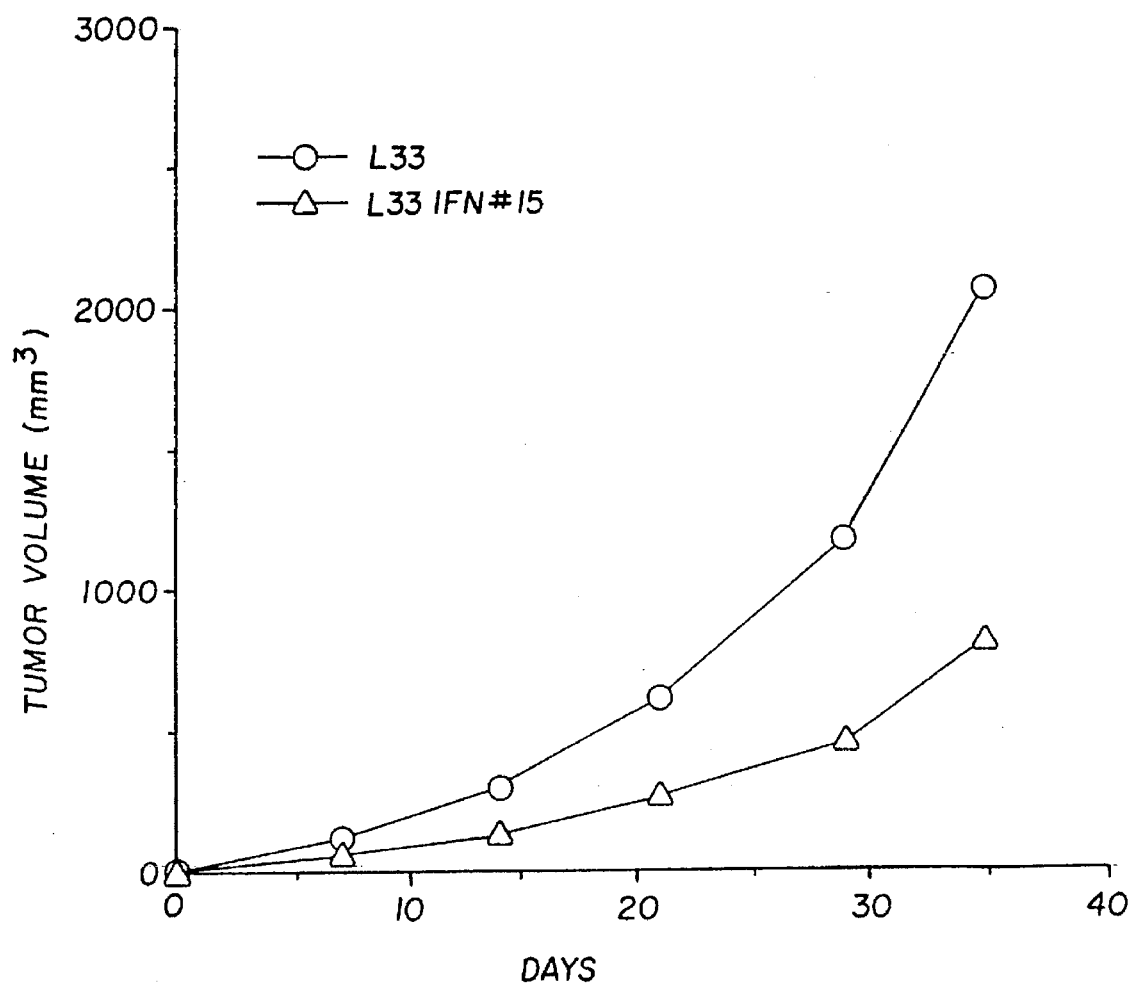
FIG. 11 is a graph which illustrates tumor growth in Balb/C nude mice which were injected with either L33 cells or L33 murine gamma-interferon #15 cells.

The data indicate that the L33 mγ-IFN #15 cells are not rejected in nude mice, FIG. 11. In addition, the mγ-IFN-expressing cells grow approximately 40% slower than do the parent L33 cells. Apparently a T-cell mediated component in the murine immune system is needed for the rejection of the L33 tumor cells. This response is induced in mice with a normal immune system but not in mice with impaired T-cell mediated immunity.

Example 11

Figure 12:
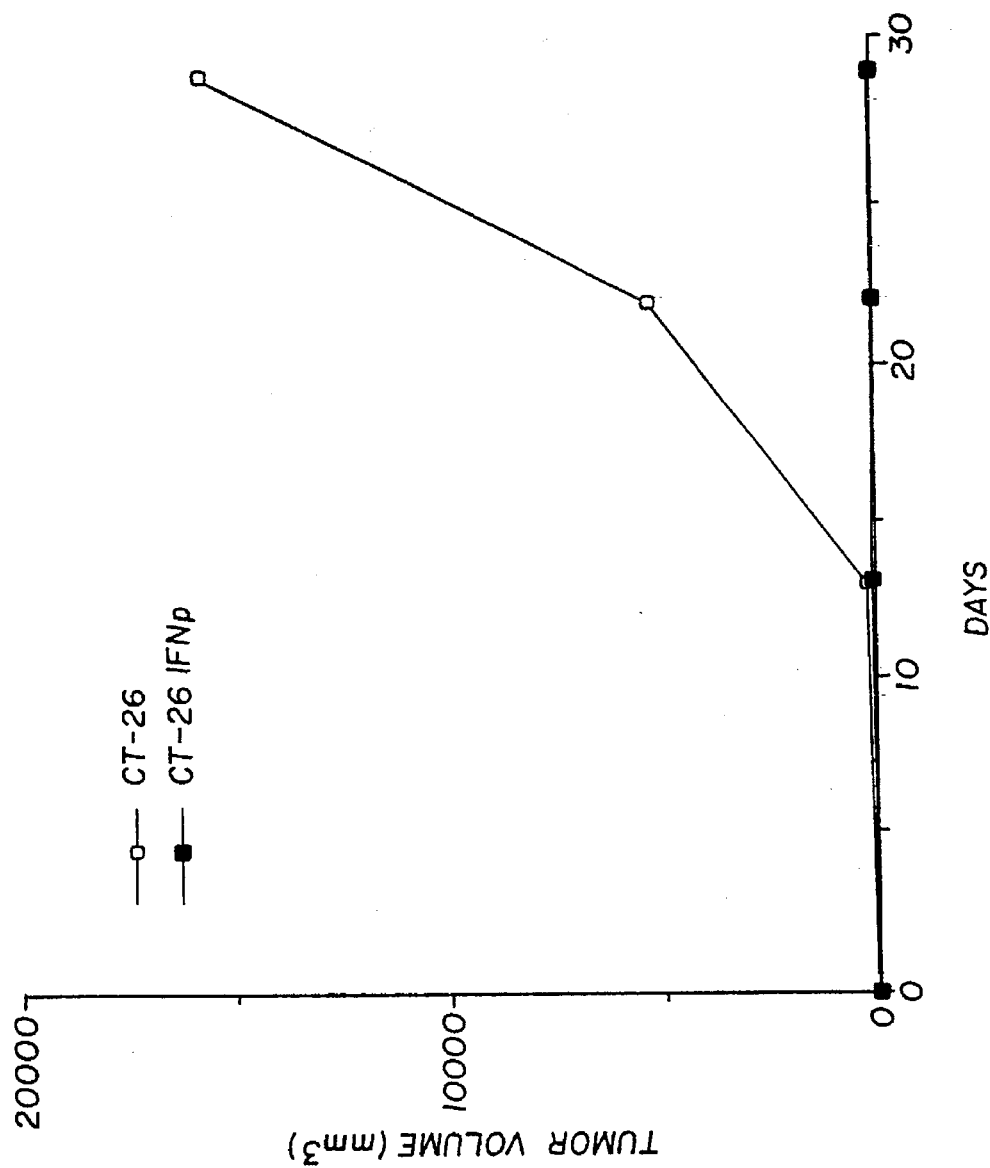
FIG. 12 is a graph which illustrates tumor growth in Balb/C mice injected which were with either CT 26 cells, or pooled CT 26 murine gamma-interferon expressing cells.

Determination of Enhanced Immunity in Balb/C Mice By mγ-IFN Expressing CT 26 Tumor Cells A. Tumorgenicity of mγ-IFN Expressing CT 26 Tumor Cells Tumorgenicity is determined by observing tumor growth in normal Balb/C mice injected with CT 26/mγ-IFN. Two groups of 10 mice are subcutaneously injected with either parent CT 26 or mγ-IFN expressing CT 26 pool. This pool is a non-clonal population of G418 selected transduced cells. These cell types are grown in 10 cm Falcon tissue culture dishes using DMEM and 10% FBS. The cells are harvested using Versene and resuspended in HBSS at a concentration of 2.5×10⁶ cells/ml. A total of 0.1 ml of cell suspension is subcutaneously injected near the sternum in each mouse. Tumor measurements of each animal are recorded weekly. The average tumor measurements are compared between the three groups. FIG. 12 presents tumor growths over a 30-day period.

The data indicate that mγ-IFN expressing CT 26 cells are rejected whereas no rejection is observed in unmodified CT 26 cells. In summary, an immune response is induced by lymphokine-expressing cells that is not induced by parent tumor cells.

B. Splenocyte Cytolytic Activity in CT 26 AND CT 26/mγ-IFN Expressing Tumor-Bearing Animals Mice that have rejected their respective mγ-IFN expressing CT 26 tumors are used to determine whether the observed rejection is due to an augmented immune response. Specifically, splenocytes are harvested from animals who had rejected their respective mγ-IFN expressing CT 26 tumor. These tumors are induced by a single subcutaneous injection of each tumor cell type of $2.0 \times 10^5$ cells near the sternum of each animal. The process of splenocyte recovery is briefly described. The spleen of a mouse is removed by making a longitudinal incision through the outer fur coat and inner abdominal wall using a pair of scissors. The spleen is then aseptically dissected away from the adjoining connective tissue and placed in HBSS. The spleen is then placed in a 10 cm plate with 2 ml of fresh HBSS. The splenocytes are removed from the spleen by creating a small tear at one end followed by a gentle stroking of the spleen using the flattened surface of a 23 gauge needle. The splenocytes are collected by adding 7 mls of HBSS to the plate. The cell suspension is collected with a piper and passed through a Nytex screen (Tetco, Elmsford, N.Y.) to break up lumps. Seven milliliters of additional medium is used to rinse the plate of remaining splenocytes and the mixture is passed through the Nytex screen. The resulting splenocytes are centrifuged in a 15 ml polypropylene tube at 1600 RPM for 5 minutes at room temperature. The pelleted splenocytes are resuspended in 14 ml of HBSS and centrifuged at 1600 rpm for 5 minutes at room temperature. The pelleted splenocytes are resuspended in 10 ml of HBSS and centrifuged at 1600 rpm for 5 minutes at room temperature. Prior to centrifugation, a dilution of an aliquot of the resuspended splenocytes is removed and counted in Trypan Blue (Irvine Scientific; Santa Ana, Calif.). The concentration of non-blue cells is determined. The splenocytes are then resuspended in RPMI and 5% heat-inactivated FBS at a concentration of $3 \times 10^7$ splenocytes/ml. The splenocytes are then restimulated in vitro. Specifically, $3 \times 10^7$ splenocytes are mixed with $6 \times 10^5$ irradiated CT 26, or other appropriate restimulator, in a T-25 cm flask with 10 ml RPMI and 5% FBS at an effector:restimulator cell ratio of 50:1 and incubated at 37° C., 5% $CO_2$, for 5–7 days. After incubation, these effectors are removed from the flask, counted and incubated with various ratios with $^{51}$chromium ($^{51}$Cr)-labeled target cells in a 96 well plate for 4 hours at 37° C. After incubation, 100 ul of supernatant from each well of each effector:target cell ratio is placed in a tube and the release of $^{51}$Cr is determined using a gamma counter. The percentage of lysis is determined using the following formula.

% Lysis =

$$\frac{(\text{Experimental Release, } CPM) - (\text{Spontaneous Release, } CPM)}{(\text{Maximum Release, } CPM) - (\text{Spontaneous Release, } CPM)} \times 100$$

Figure 13:
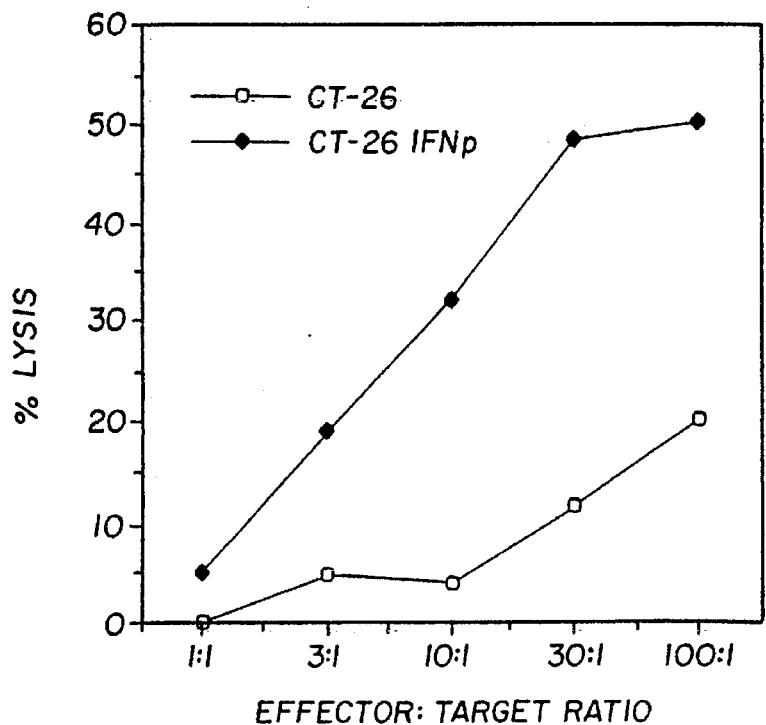
FIG. 13 is a graph which illustrates CTL induction by pooled CT 26 murine gamma-interferon expressing cells (a non-clonal pool) in non-tumor bearing animals.

The data indicates that a potent immune response is induced in animals that rejected their mγ-IFN expressing CT 26 cells, FIG. 13. In summary, the mγ-IFN expressing CT 26 cells can induce an immune response that the parent tumor cannot induce.

Example 12

Figure 14:
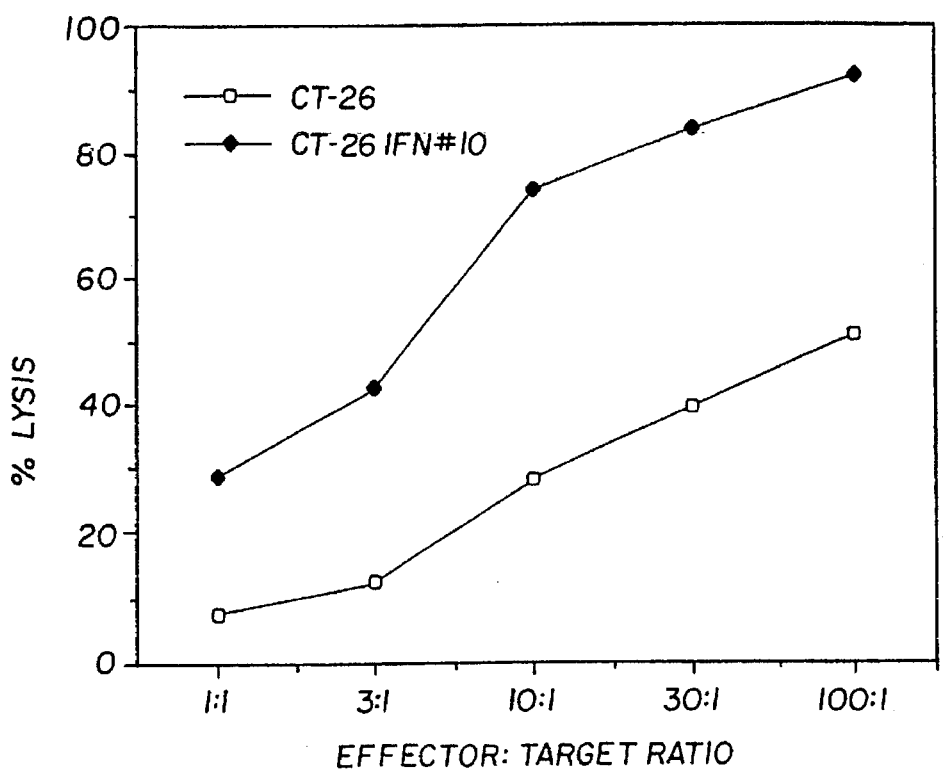
FIG. 14 is a graph which illustrates CTL induction by irradiated CT 26 murine gamma-interferon #10 expressing cells.

Induction of Splenocyte Cytolytic Activity in Balb/C Mice Using Irradiated CT 26 or CT 26/mγ-IFN Expressing Tumor Cells A. Generation of Splenocyte Cytolytic Activity Using Two Injections of CT 26 or CT 26/mγ-IFN Expressing Cells A series of injections are performed to determine whether irradiated mγ-IFN CT 26 cells could enhance immune activation against CT 26 more than irradiated unmodified CT 26. Two mice are injected with two weekly doses of $1.0 \times 10^7$ irradiated CT 26 or CT 26/mγ-IFN #10 cells per dose. After two weeks, the spleens are removed, stimulated/n vitro with their respective inducers and used against chromium labeled CT 26 targets in a $^{51}$Cr release assay. The data indicates that the cytotoxicity of the CT 26/mγ-IFN effectors are more potent against CT 26 than CT 26 effectors, FIG. 14.

Figure 15:
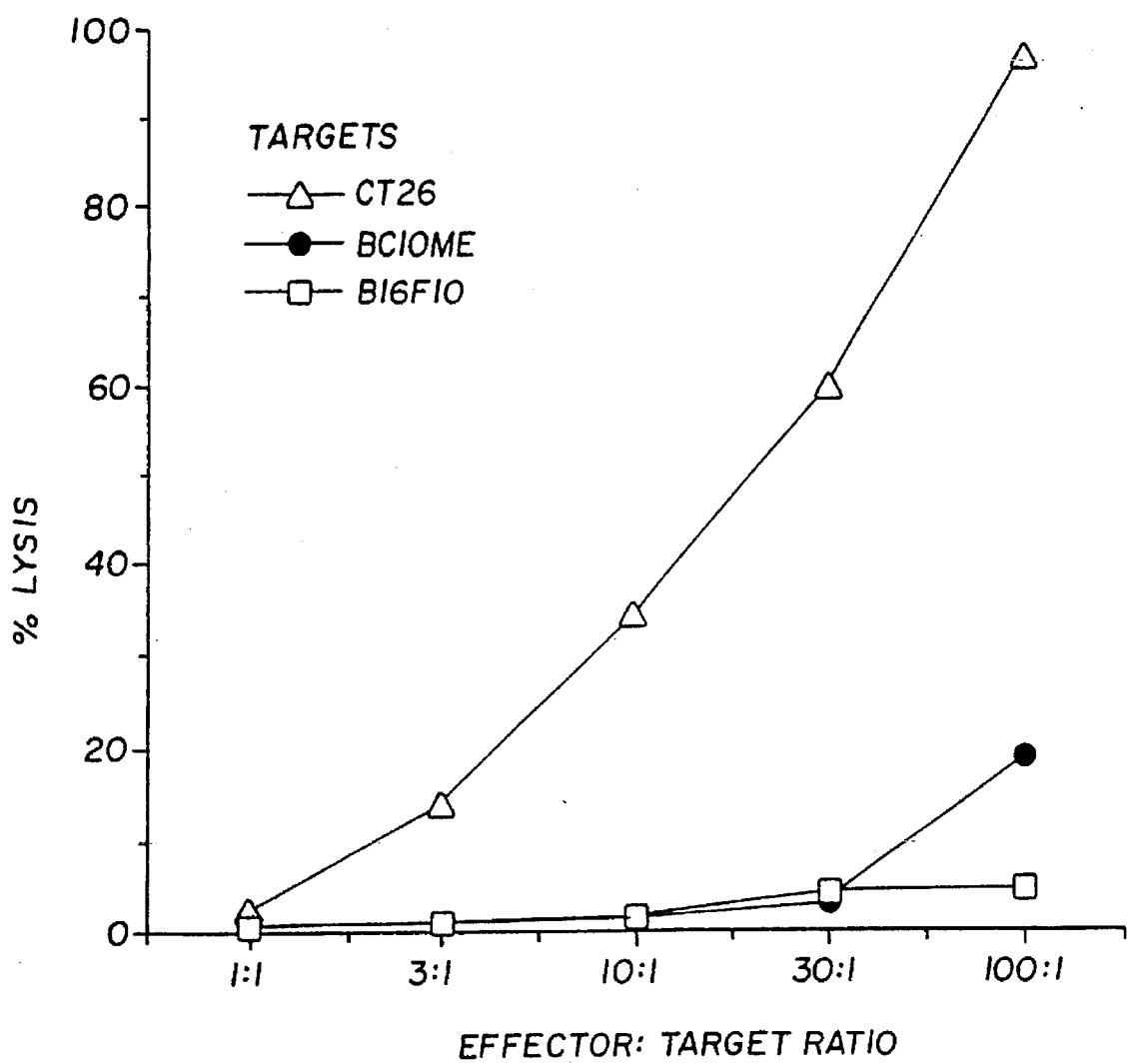
FIG. 15 is a graph which illustrates CTL specificity of CT 26 murine gamma-interferon #10 for CT 26target cells.

B. Specificity of Splenocytes Induced by the Two Injections of CT 26 or CT 26/mγ-IFN Expressing Tumor Cells The splenocyte effectors generated by a two dose regimen of $1 \times 10^7$ CT 26/mγ-IFN #10 cells are used in a $^{51}$Cr release assay against several non-CT 26 targets to demonstrate specificity for CT 26. BC10ME, a syngeneic line in Balb/C mice, and B16F10, a tumor cell line obtained from a different strain of mice C57B1/6 (Harlan Sprague-Dawley, Indianapolis, Ind.) and not Bath/C, are selected. The data indicate that, when CT 26 cells expressing mγ-IFN are used as stimulators, the response induced is specific to CT 26 and not against other cell types of either the same strain of mouse or of an unrelated strain, FIG. 15.

Figure 16:
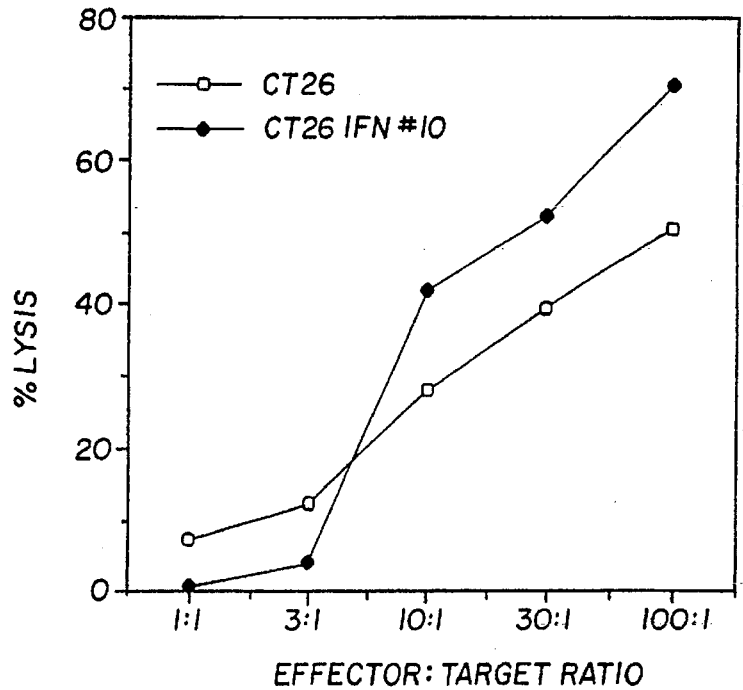
FIG. 16 is a graph which illustrates the effect of murine gamma-interferon expression by CT 26 murine gamma-interferon #10 cells, on CT 26 CTL lysis.

C. Enhanced Cytolysis of CT 26γ-IFN Expressing Tumor Cells mγ-IFN expressing $^{51}$Cr labeled CT 26 target cells show enhanced lysis in chromium release assays when using effector splenocytes generated by the two dose regimen of $1 \times 10^7$ irradiated CT 26 cells. The data in FIG. 16 indicates that CT 26 expressing mγ-IFN cells serve as better targets than unmodified CT 26 cells. It is possible that the mγ-IFN expressed by these modified CT 26 targets may induce greater affinity for the CT 26 effectors which results in more efficient cytolysis by these effectors. The enhanced level of MHC molecules on the surface of these cells may also contribute to the enhanced lysis.

Example 13

Figure 17:
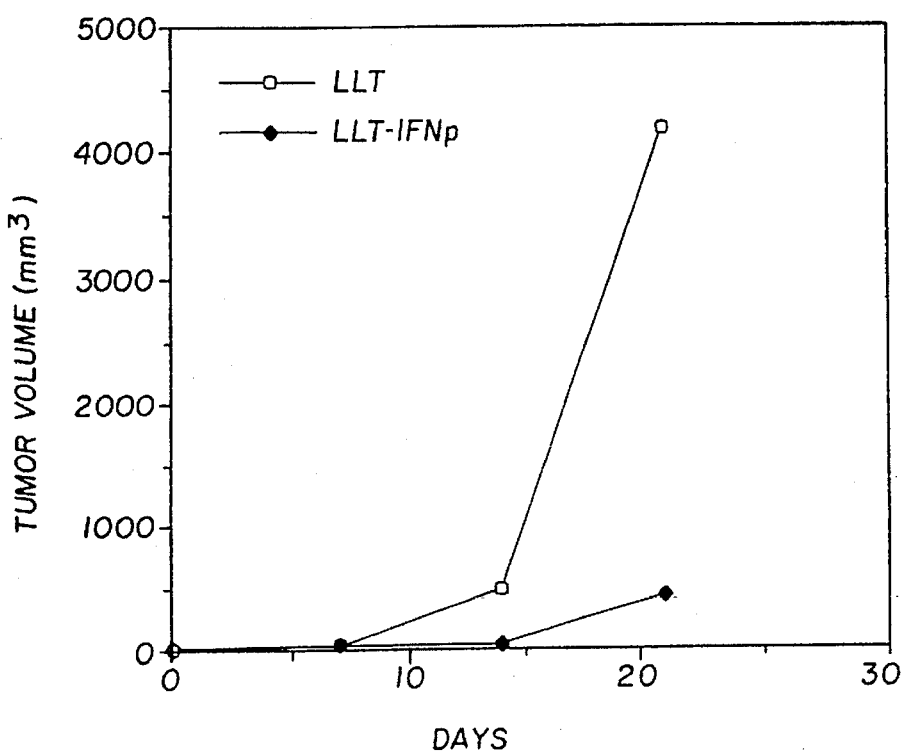
FIG. 17 is a graph which illustrates tumor growth in C57B1/6 mice which were injected with either LLT cells or LLT murine gamma-interferon expressing cells.

Determination of Enhanced Immunity in C57BL/6 Mice by mγ-IFN Expressing LLT Cells A. Tumorigenicity of mγ-IFN Expressing LLT Cells Tumorgenicity of mγ-IFN expressing LLT cells is determined by injection into normal C57B1/6 mice. Two groups of ten mice are subcutaneously injected with either parent LLT or mγ-IFN-expressing LLT pool. These cells are grown as described in Example 3 C 3.The cells are harvested, as described in Example 13 A, and resuspended in HBSS at a concentration of $2.5 \times 10^6$ cells/ml. One tenth of a milliliter of cell suspension is subcutaneously injected near the sternum of each mouse. Tumor measurements are recorded weekly and the average tumor sizes are compared between the two groups. FIG. 17 represents tumor growth over a period of 21 days.

The data indicate that both the mγ-IFN expressing LLT cells grow significantly slower than the unmodified LLT cells. In summary, the data implies that a partial immune response is induced by mγ-IFN-expressing cells that is not induced by parent LLT cells.

Figure 18:
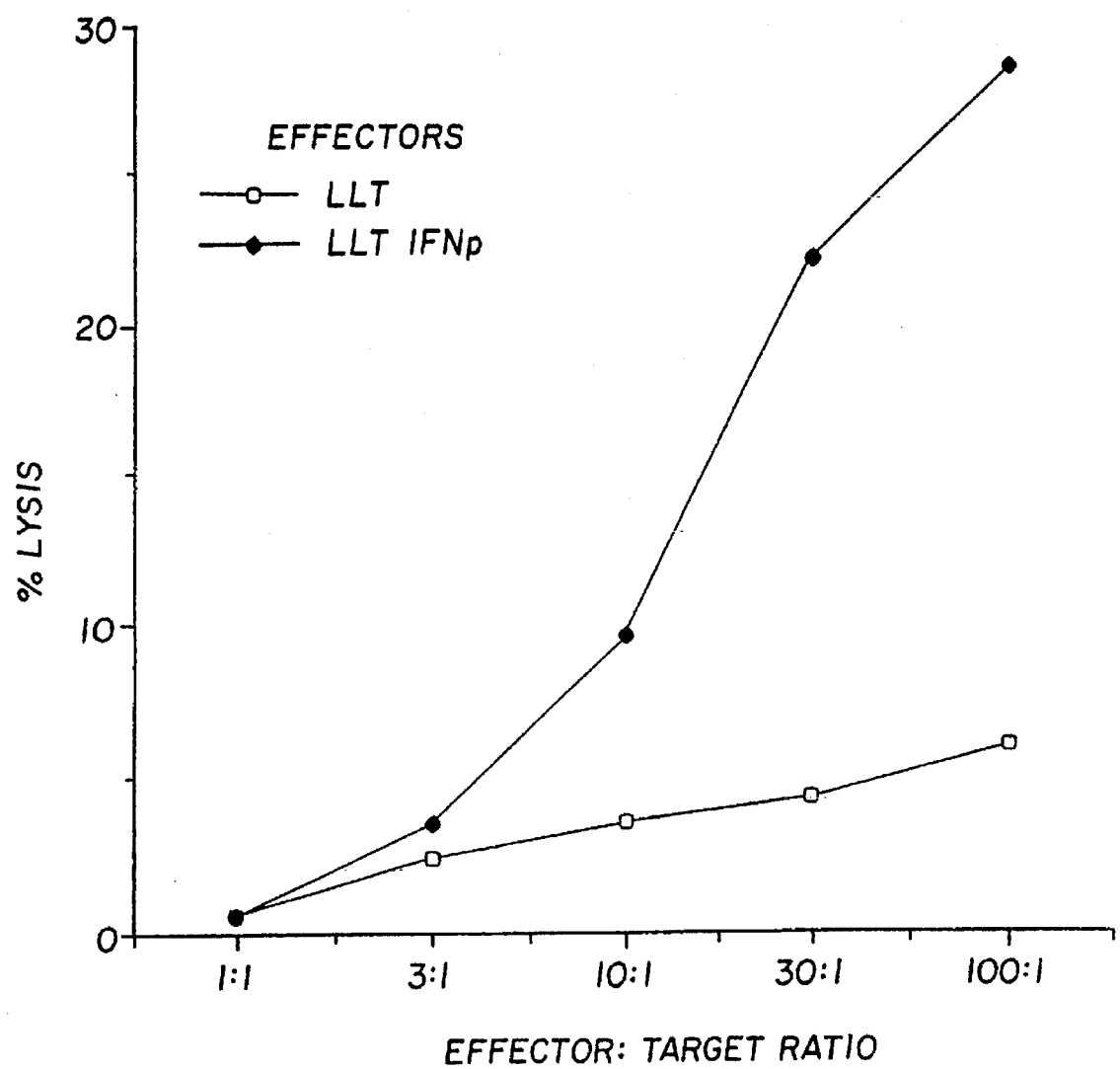
FIG. 18 is a graph which illustrates CTL induction by irradiated LLT murine gamma-interferon expressing cells.

B. Generation of Splenocyte Cytolytic Activity Using Two Injections of mγ-IFN Expressing LLT Cells A series of injections in C57B1/6 mice are performed in order to determine whether irradiated mγ-IFN modified LLT cells enhance a greater immune activation against LLT cells than irradiated LLT cells. Mice are injected with two weekly doses of $1 \times 10^7$ irradiated LLT or LLT/mγ-IFN pool. Two weeks following the last injection, spleens are removed, stimulated in vitro with their respective inducer, and used against $^{51}$Cr-labeled LLT targets in a chromium release assay. The data indicates that the cytotoxicity of the LLT/mγ-IFN effectors are more potent against LLT than LLT effectors or unmodified stimulators demonstrating the greater effectiveness of mγ-IFN expressing stimulator cells, FIG. 18.

Figure 19:
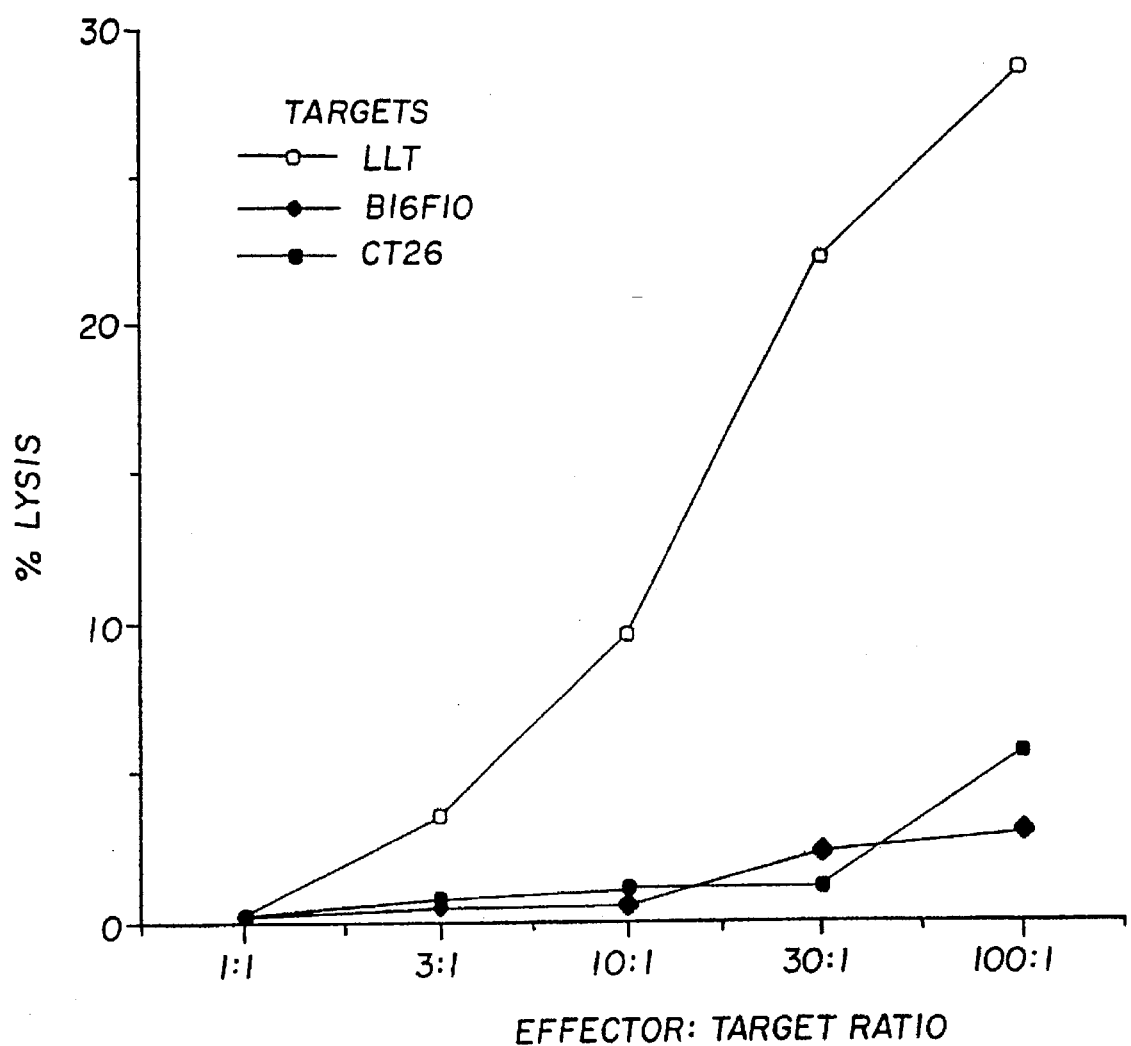
FIG. 19 is a graph which illustrates CTL specificity of LLT murine gamma-interferon effector T-cells for LLT target cells.

C. Specificity of Splenocytes Induced by Two Injections of γ-IFN Expressing LLT Cells The splenocyte effectors generated by a two dose regimen of 1×10⁷ LLT mγ-IFN pool cells are used in a chromium release assay against several non-LLT targets to demonstrate specificity for LLT. B16F10, a syngeneic tumor line in C57B1/6 mice, and CT 26, a tumor cell line in Balb/C mice but not C57B1/6, are selected. The data indicates that, by using LLT cells expressing mγ-IFN as stimulators, the response induced is specific to LLT and not against other cell types of either the same strain of mouse or of an unrelated strain, FIG. 19.

Figure 20:
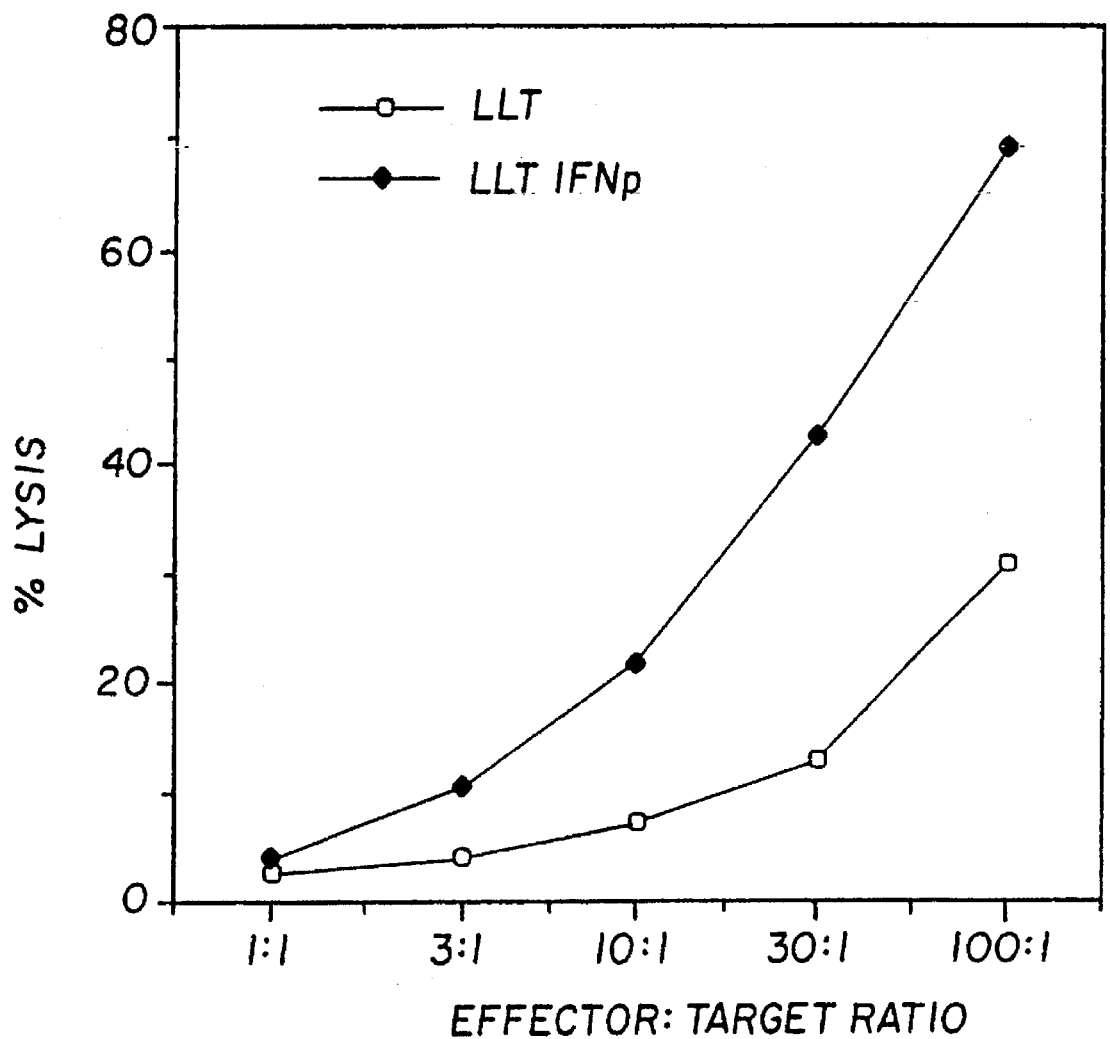
FIG. 20 is a graph which illustrates the effect of murine gamma-interferon expression by LLT murine gamma-interferon cells on LLT CTL lysis.
Figure 21A:
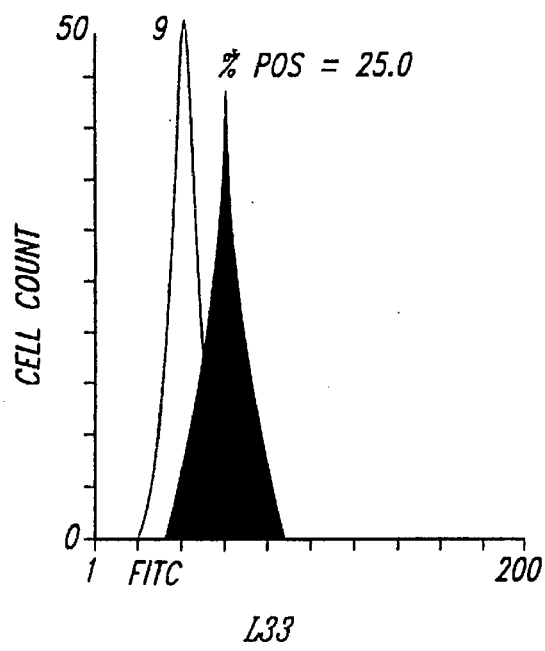
FIGS. 21A, 21B, 21C, and 21D are a series of graphs which depict the FACS analysis of MHC levels in L33 cells, L33 murine gamma-interferon #13 cells, L33 murine gamma-interferon #15 cells, and L33 murine gamma-interferon expressing cells (a non-clonal pool).
Figure 21B:
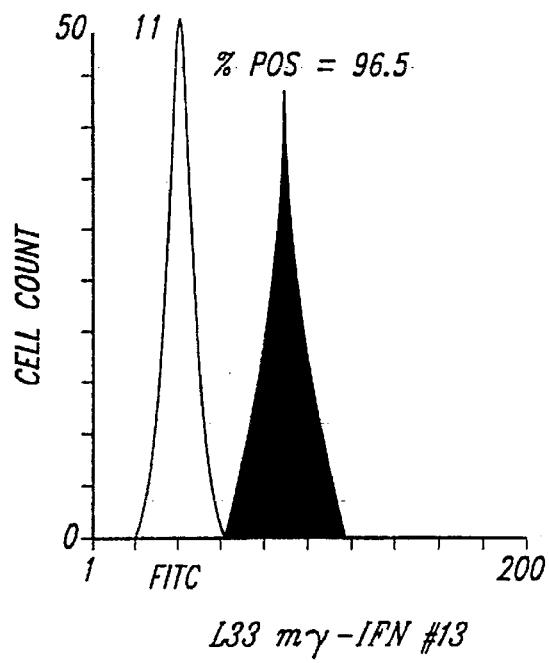
Figure 21C:
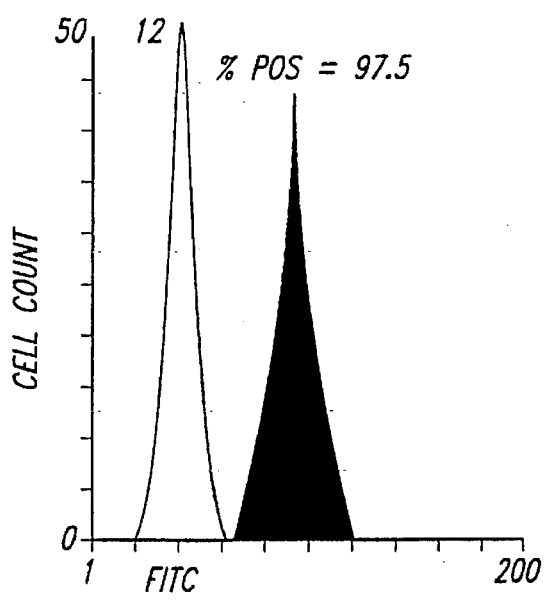
Figure 21D:
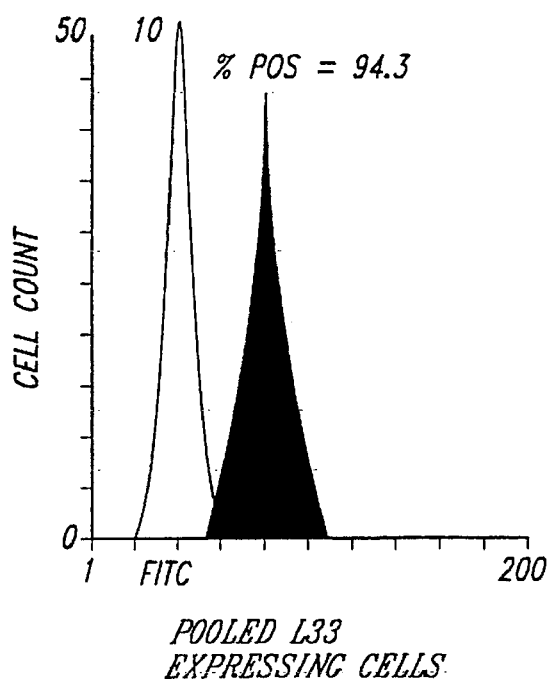

D. Enhanced Cytolysis of LLT mγ-IFN Expressing Tumor Cells mγ-IFN expressing $^{51}$Cr-labeled LLT target cells show enhanced lysis in chromium release assays when using effector splenocytes generated by the two dose regimen of 1×10⁷ irradiated LLT cells, FIG. 20. The data indicates that LLT expressing mγ-IFN cells serve as better targets than unmodified LLT cells. It is possible that the mγ-IFN that are expressed by these modified LLT targets induce greater affinity for the LLT effectors which result in more efficient cytolysis by these effectors.

Example 14

HLA Class I and hγ-IFN Expression in Transduced Human Melanomas

A. Determination of Human MHC (HLA) Class 1 Expression by Western Blot Analysis.

HLA expression is determined essentially as described in Example 5A for murine MHC except that the. HLA Class I specific antibody W6/32 is used.

Figure 22:
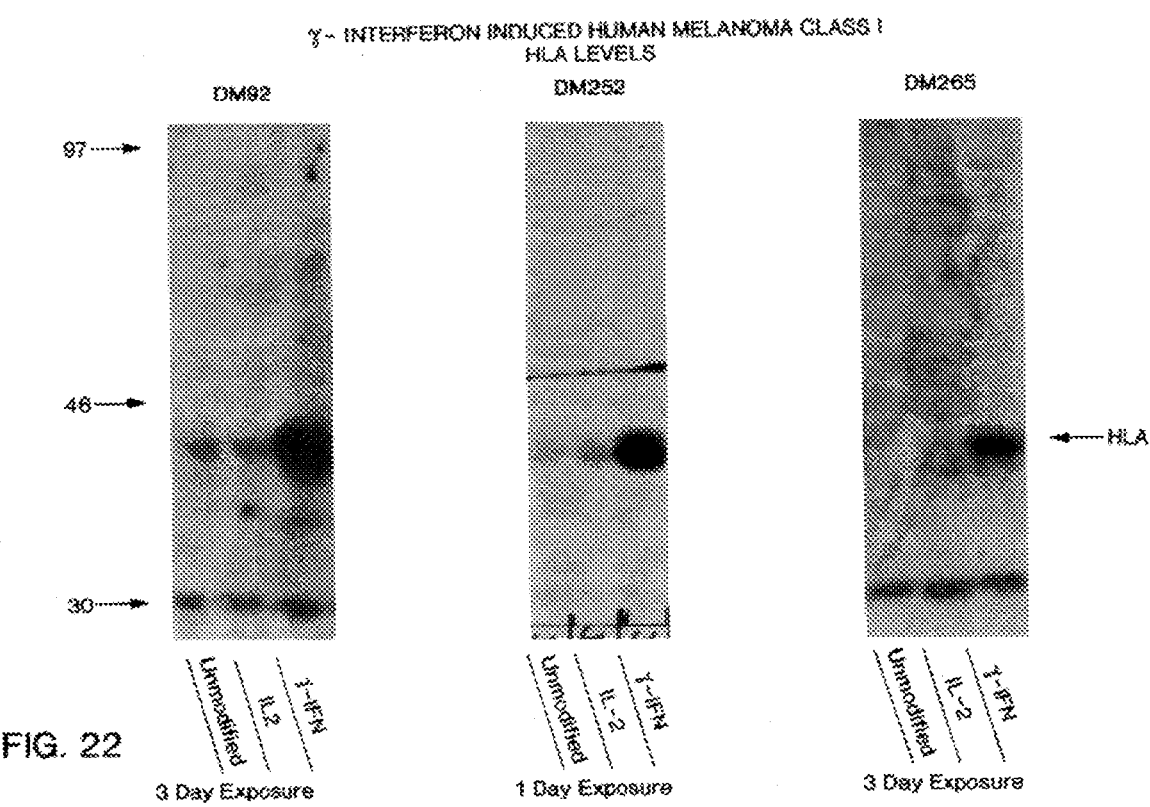
FIG. 22 is a series of Western Blots which shows the increase in HLA Class I in γ-IFN-expressing human melanomas.
Figure 23:
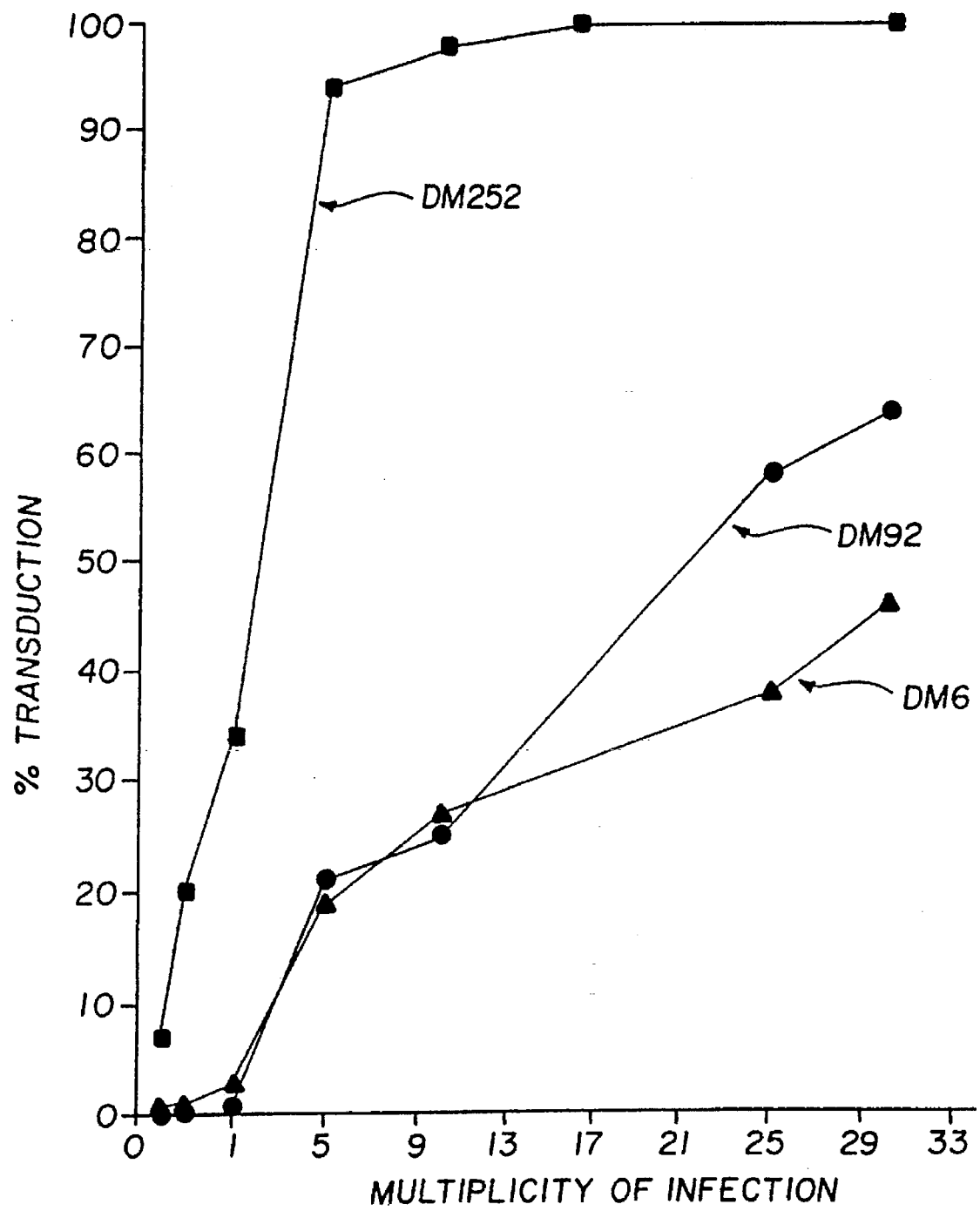
FIG. 23 is a graph which depicts the percent transduction vs. Multiplicity of Infection ("MOI") for melanomas DM252, DM6, and DM92.

B. Analysis and HLA Expression in Human Melanomas With and Without hγ-IFN Retroviral Vector DM92, DM252, or DM265 are treated with hγ-IFN vector or hIL-2 as a control for vector transduction. The data in FIG. 22 indicates that hγ-IFN vector increases the level of HLA compared with the non-transduced cells whereas, those transduced with IL-2 did not. Transduction of DM265 results in increased HLA even though there is little or no hγ-IFN secreted into the medium. (Table 4).

hγ-IFN is quantified by viral inhibition of encephalomyocarditis virus on a chimpanzee cell line A549, ATCC CCL 185. Activity is determined by comparison with authentic NIH reference reagents and normalized to NIH reference units (U/mL) (Brennan et al., Biotechniques 1:78, 1983). The data for several human melanoma cell lines are reported in Table 4. These data indicate that all human melanomas transduced with the hγ-IFN retroviral vector express readily detectable levels of biologically active hγ-IFN. This expression is often stable with time (Table 5, DM252 and DM92) but sometimes decreases with time in culture (Table 4, DM6 and DM265). This time dependent decrease in hγ-IFN may indicate that expression of the gene is somewhat toxic thus resulting in a selective advantage for cells expressing low levels of hγ-IFN.

TABLE 5 mγ-IFN ACTIVITY IN HUMAN MELANOMA CELL LINES

| hγ-IFN Production | Day | U/ml |
|---|---|---|
| DM262 | | <1.1 |
| DM262/Dhγ-IFN | 20 | 20 |
| DM252 | | <6.6 |
| DM252/Dhγ-IFN | 2 | 710 |
| | 15 | 890 |
| | 20 | 1700 |
| | 27 | 400 |
| | 34 | 470 |
| | 73 | 370 |
| | 84 | 240 |
| DM6 | | <5.0 |
| DM6/Dhγ-IFN | 6 | 54 |
| | 13 | 63 |
| | 20 | 37 |
| | 34 | <7.7 |
| | 73 | <1.1 |
| DM92 | | <5.0 |
| DM92/Dhγ-IFN | 6 | 83 |
| | 13 | 54 |
| | 20 | 83 |
| | 30 | 45 |
| | 34 | 56 |
| DM265 | | <4.4 |
| DM265/Dhγ-IFN | 13 | 45 |
| | 16 | 45 |
| | 20 | <7.7 |
| | 37 | <1.1 |
| | 58 | 4.6 |
| | 70 | <1.1 |
| DM259 | | <1.1 |
| DM259/Dhγ-IFN | 30 | 8.1 |

Example 15

Transducibility of Human Melanoma Cell Lines by Retroviral Vectors

A. Transduction of Human Melanoma Cell Lines with Unconcentrated VectorSupernatants Human melanoma cell lines, DM6, DM92 and DM252 were transduced at different MOI with retroviral vector which expresses E. coli β-galactosidase gene (CBβgal). CBβgal is a vector made by replacing the HIV IIIB gag/prot gene of KT-3 with the E. coli β-galactosidase gene. Producer cell lines were generated in a manner analogous to that described in Examples 1, 3 and 4. Three days after transduction with CBβgal the cells were stained with X-gal (Gold Biotechnology, St. Louis, Mo.), the number of blue cells were enumerated and the percent transduction was calculated (Norton, et al., Molec. and Cell. Biol. 5:218–290, 1985). The results indicate that the three human melanoma cell lines were all easily transducible, approaching 100% transduction.

B. Transduction Efficiencies of Human Melanomas Using Concentrated Vector

Figure 24:
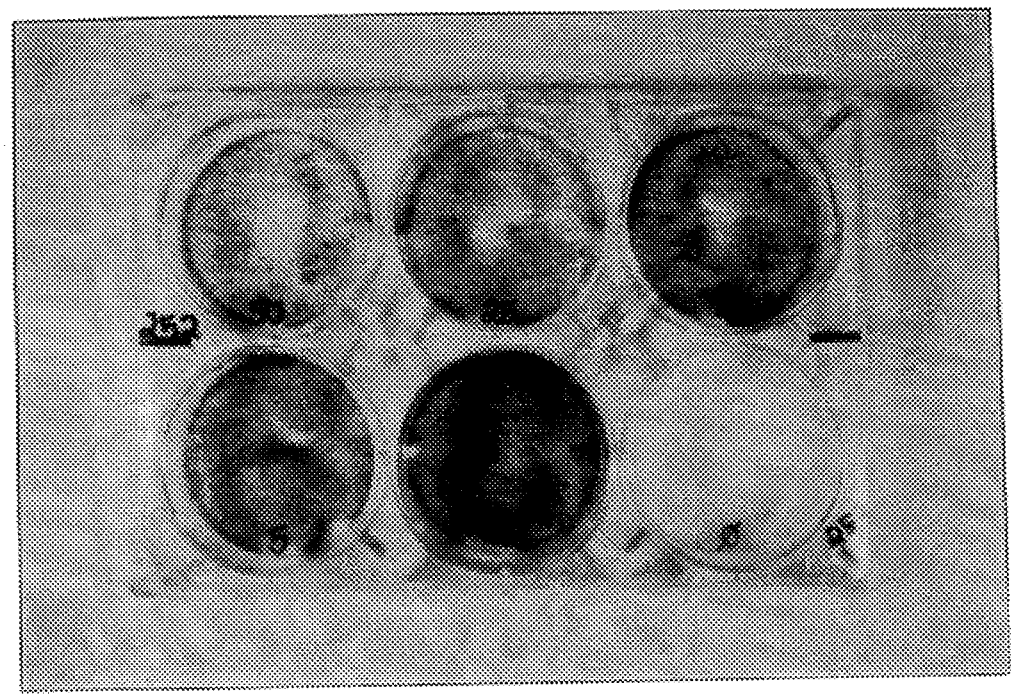
FIG. 24 is a photograph of a 6-well plate containing melanoma cells, which shows the transduction of human melanomas with concentrated unpurified vector.

Amphotropic CBβ3gal vector was harvested from CA producer cell lines and concentrated 40-fold by tangential flow concentration. Six well plates of DM252, DM6 and DM92 are set up at 4×10⁴ cells/well. The next day, day 0, each melanoma cell line is transduced at an MOI of 50, 25, 10, 5, 1.and 0 with CBβ gal vector that is concentrated but not purified. The next day, (day 1) the vector is removed from the cells and the cells are rinsed with media. On day 5, cells are stained with X-gal. These cells are not selected with G418. The transduction efficiency of human melanomas decreased with increasing MOIs when concentrated vector is used (FIG. 24) suggesting the presence of an inhibitor to transduction. Therefore, purification of vector may be crucial for direct injection of vector into tumors which will require concentrated vector. Purification methods may include methods typically used by those skilled in the art for protein purification such as gel filtration or ion exchange chromatography. Microscopic inspection of samples, MOI= 1.0 for the above experiment indicated that even under these conditions 25–90% of the cell population can be transduced without the aid of G418 selection (FIG. 25).

C. Transduction Time Experiment After Culture Initiation

Figure 26:
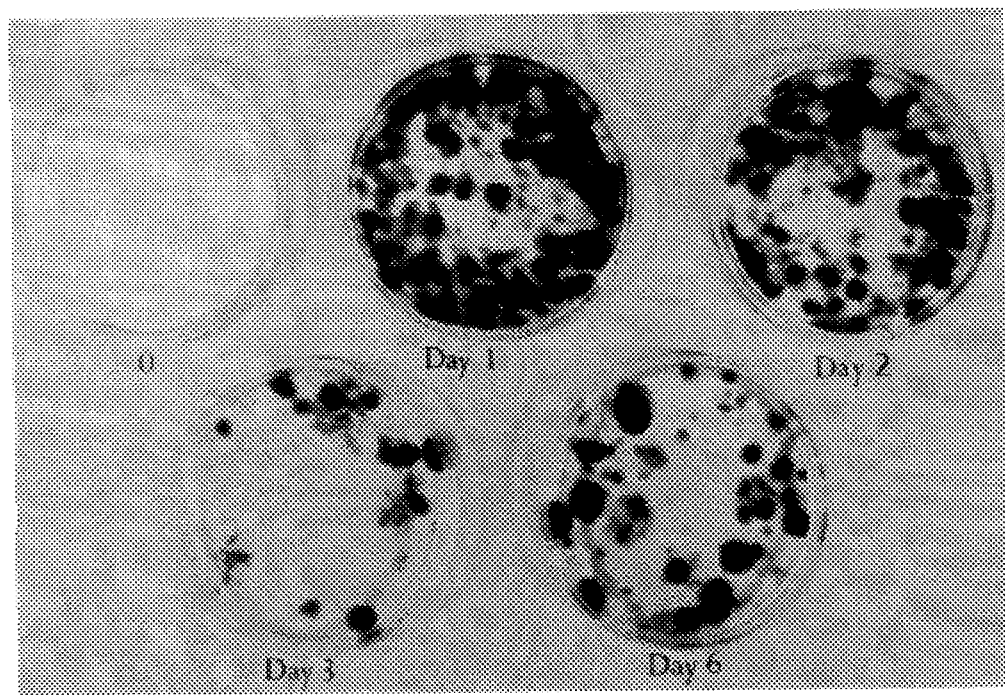
FIG. 26 is a photograph of 4 tissue culture plates which shows that human melanoma is easily transfected within 24 hours after induction into tissue culture.

Chunks from human tumor biopsy DM262 which had been frozen, are thawed, minced with scalpels, ground through a mesh and plated in ten 6.0 cm tissue culture plates. On days 1, 2, 3, 6, 7, 8, 9, 10 and 13 after culture initiation, one plate is transduced with $1.0 \times 10^6$ cfu of unpurified CBβgal vector. On day 20, all of the plates are stained with X-gal. These cells are not selected with G418. The data indicate, FIG. 26, that the tumor is rapidly transducible with a high efficiency as soon as one day after culture initiation. Transduction immediately after culture initiation will allow the melanomas to be returned to patients rapidly and with minimum effects due to hy-IFN toxicity or antigenic drift while in culture. The high efficiency of transduction so soon after plating suggests that in vivo transduction by direct injection of vector into tumors may be effective.

Example 16

Direct Administration of Vector into Tumor Bearing Animals

A. Direct Administration of Vector into Mice

Mouse tumor systems may be utilized to show that cell mediated immune responses can be enhanced by direct administration of a vector construct which expresses at least one anti-tumor agent. For example, six to eight week old female Balb/C or C57B1/6 mice are injected subcutaneously with $1 \times 10^5$ to $2 \times 10^5$ tumor cells which are allowed to grow within the mice for one to two weeks. The resulting tumors can be of variable size (usually 1–4 $mm^3$ in volume) as long as the graft is not compromised by either infection or ulceration. One-tenth to two-tenths of a milliliter of a vector construct which expresses an anti-tumor agent such as γ-IFN, (minimum titer $10^6$ cfu/ml) is then injected intratumorally (with or without polybrene or promarine sulfate to increase efficiency of transduction). Multiple injections of the vector are given to the tumor every two to three days.

Depending on the parameters of the particular experiment, the nature of the vector preparations can be variable as well. The vector can be from filtered or unfiltered supernatant from vector producing cell lines (VCL), or may be processed further by filtration, concentration or dialysis and formulation. Other standard purification techniques, such as gel filtration and ion exchange chromatography, may also be utilized to purify the vector. For example, dialysis can be used to eliminate γ-interferon that has been produced by the VCL itself (and which, if administered, may effect tumor growth). Dialysis may also be used to remove possible inhibitors of transduction. Another option is to perform intratumor injections of the γ-interferon VCL itself, in order to more extensively introduce the vector. Briefly, cells are injected after being spun down from culture fluid and resuspended in a pharmaceutically acceptable medium (e.g., PBS plus 1 mg/ml HSA). As few as $10^5$ cells may be used within this aspect of the invention.

Efficacy of the vector construct may be determined by measuring the reduction in primary tumor growth, the reduction in tumor burden (as determined by decreased tumor volume), or by the induction of increased T-cell activity against tumor target cells (as measured in an in vitro assay system using lymphocytes isolated from the spleens of these tumor bearing cells). In a metastatic murine tumor model, efficacy may also be determined by first injecting tumor cells that are metastatic, and, when the tumor is 1–4 $mm^3$ in volume, injecting vector several times into that tumor. The primary tumor graft may then be surgically removed after 2–3 weeks, and the reduction in metastases to the established target organ (lung, kidney, liver, etc.) counted. To measure the change in metastases in a target organ, the organ can be removed, weighed, and compared to a non-tumor bearing organ. In addition, the amount of metastases in the target organ can be measured by counting the number of visible metastatic nodules by using a low powered dissecting microscope.

B. Direct Administration of Vector into Humans

For humans, the preferred location for direct administration of a vector construct depends on the location of the tumor or tumors. The human γ-interferon gene or other sequences which encode anti-tumor agents can be introduced directly into solid tumors by vector administration (the vectors may be purified as previously described). They may also be delivered to leukemias, lymphomas or ascites tumors. For skin lesions such as melanomas, the vector may be directly injected into or around the lesion. At least $10^5$ cfu of vector particles should be administered, preferably more than $10^6$ cfu in a pharmaceutically acceptable formulation (e.g., 10 mg/ml mannitol, 1 mg/ml HSA, 25 mM Tris pH 7.2 and 105 mM NaCl). For internal tumor lesions, the effected tumor can be localized by X-ray, CT scan, antibody imaging or other methods known to those skilled in the art of tumor localization. Vector injection can be through the skin into internal lesions, or by adaptations of bronchoscopy (for lungs), sigmoidoscopy (for colorectal or esophageal tumors) or intra-arterial or intra-blood vessel catheter (for many types of vascularized solid tumors). The injection can be into or around the tumor lesion. The efficiency of induction of a biological response may be measured by CTL assay or by delayed type hypersensitivity (DTH) reactions to the tumor. Efficacy and clinical responses may be determined by measuring the tumor burden using X-ray, CT scan or antibody imaging or other methods known to those skilled in the art of tumor localization.

From the foregoing, it will be appreciated that, although specific embodiments of the invention have been described herein for purposes of illustration, various modifications may be made without deviating from the spirit and scope of the invention. Accordingly, the invention is not limited except as by the appended claim.

We claim:

1. A method for inhibiting the growth of a selected solid tumor in a warm-blooded animal, comprising directly administering to said tumor a recombinant retroviral vector which directs the expression of gamma-interferon, such that the growth of said tumor is inhibited.

2. The method according to claim 1 to wherein said solid tumor is a melanoma.

3. The method according to claim 1 wherein said warm-blooded animal is a human.

4. The method according to claim 1, further comprising the step of directly administering to said solid-tumor a recombinant retroviral vector which directs the expression of interleukin-2.

* * * * *